US012653699B2

(12) United States Patent
Haque

(10) Patent No.: US 12,653,699 B2
(45) Date of Patent: Jun. 16, 2026

(54) SYSTEMS AND METHODS FOR PRONE LATERAL SPINE SURGERY

(71) Applicant: PERSPECTIVE TECHNOLOGIES, LLC, Orlando, FL (US)

(72) Inventor: Maahir Haque, Orlando, FL (US)

(73) Assignee: PERSPECTIVE TECHNOLOGIES, LLC, Orlando, FL (US)

( * ) Notice: Subject to any disclaimer, the term of this patent is extended or adjusted under 35 U.S.C. 154(b) by 122 days.

(21) Appl. No.: 18/797,386

(22) Filed: Aug. 7, 2024

(65) Prior Publication Data

US 2025/0032274 A1 Jan. 30, 2025

Related U.S. Application Data

(63) Continuation of application No. 18/555,208, filed as application No. PCT/US2023/060571 on Jan. 12, 2023, now Pat. No. 12,042,405.
(Continued)

(51) Int. Cl.
*A61F 2/46* (2006.01)
*A61B 17/70* (2006.01)
(Continued)

(52) U.S. Cl.
CPC .......... *A61F 2/4611* (2013.01); *A61B 17/708* (2013.01); *A61F 2/4455* (2013.01); *A61B 2017/0256* (2013.01); *A61B 2017/681* (2013.01)

(58) Field of Classification Search
CPC ....... A61B 17/70; A61B 17/708; A61B 17/02; A61B 17/0206; A61B 17/00; A61F 2/44; A61F 2/4455; A61F 2/46; A61F 2/4611
See application file for complete search history.

(56) References Cited

U.S. PATENT DOCUMENTS

2008/0021285 A1 1/2008 Drzyzga et al.
2009/0222045 A1 9/2009 Gorek
(Continued)

FOREIGN PATENT DOCUMENTS

CN 2619600 Y 6/2004
CN 1889889 A 1/2007
CN 103690205 A 4/2014

OTHER PUBLICATIONS

International Search Report and Written Opinion for PCT Patent Application No. PCT/US2023/060571, mailed on Jul. 20, 2023, 2011, 17 pages.
(Continued)

*Primary Examiner* — Christopher J Beccia
(74) *Attorney, Agent, or Firm* — Adler Pollock & Sheehan P.C.

(57) ABSTRACT

Internal fixation systems and methods for prone lateral spine surgery on a patient. The system comprises a lateral lumbar interbody fusion (LLIF) retractor and a posterior compressor/distractor including a posterior distractor rack assembly having a rack and a posterior distractor carriage assembly configured to operably engage the posterior distractor rack assembly. The posterior distractor rack assembly includes a first swivel tube subassembly having a first swivel tube, and the posterior distractor carriage assembly includes a second swivel tube subassembly having a second swivel tube. The first and second swivel tubes are each configured to receive a pedicle screw and screw tower therein. The first and second swivel tube subassemblies are configured to be moved and positioned with respect to each other, such that a surgeon can access the patient's disc space from the left and right sides, and without the need for a bolster.

26 Claims, 58 Drawing Sheets

Related U.S. Application Data

(60) Provisional application No. 63/306,785, filed on Feb. 4, 2022, provisional application No. 63/299,279, filed on Jan. 13, 2022.

(51) Int. Cl.
    *A61F 2/44*         (2006.01)
    *A61B 17/02*       (2006.01)
    *A61B 17/68*       (2006.01)

(56)                References Cited

U.S. PATENT DOCUMENTS

| | | |
|---|---|---|
| 2009/0227845 A1 | 9/2009 | Lo et al. |
| 2010/0298885 A1 | 11/2010 | Tribus |
| 2011/0263945 A1 | 10/2011 | Peterson et al. |
| 2012/0041272 A1 | 2/2012 | Dietze et al. |
| 2015/0018623 A1 | 1/2015 | Friedrich et al. |
| 2017/0049428 A1 | 2/2017 | Cryder et al. |
| 2021/0353277 A1 | 11/2021 | Gregersen et al. |

OTHER PUBLICATIONS

U.S. Appl. No. 18/555,208, filed Jul. 23, 2024, Haque.

BOLSTER

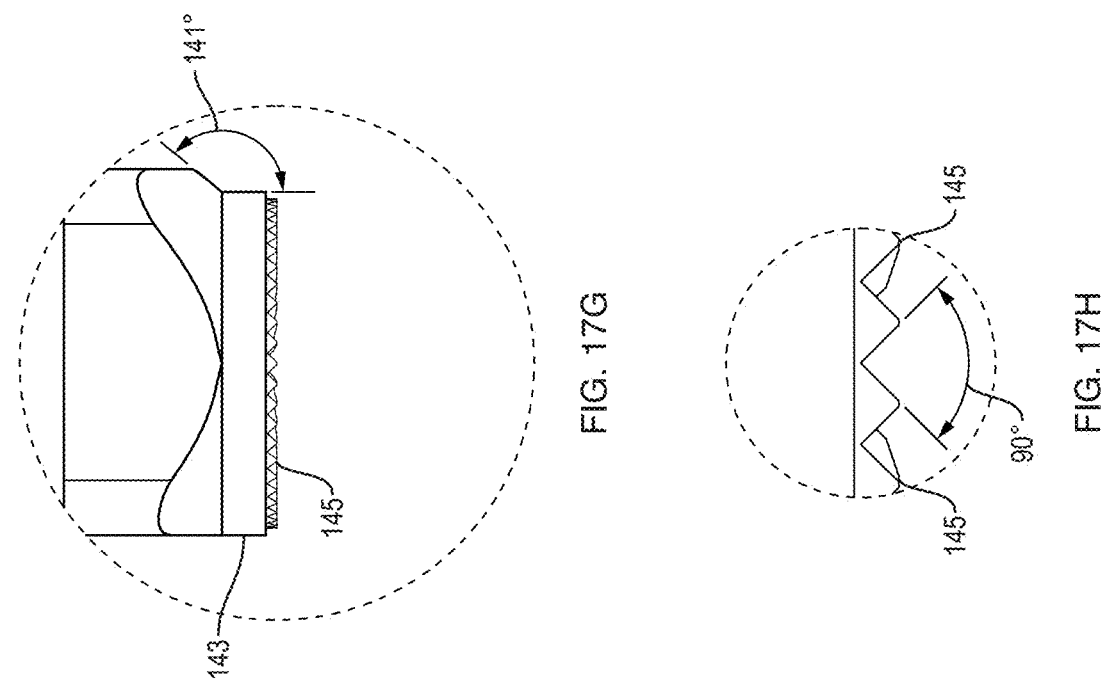
FIG. 17G
FIG. 17H
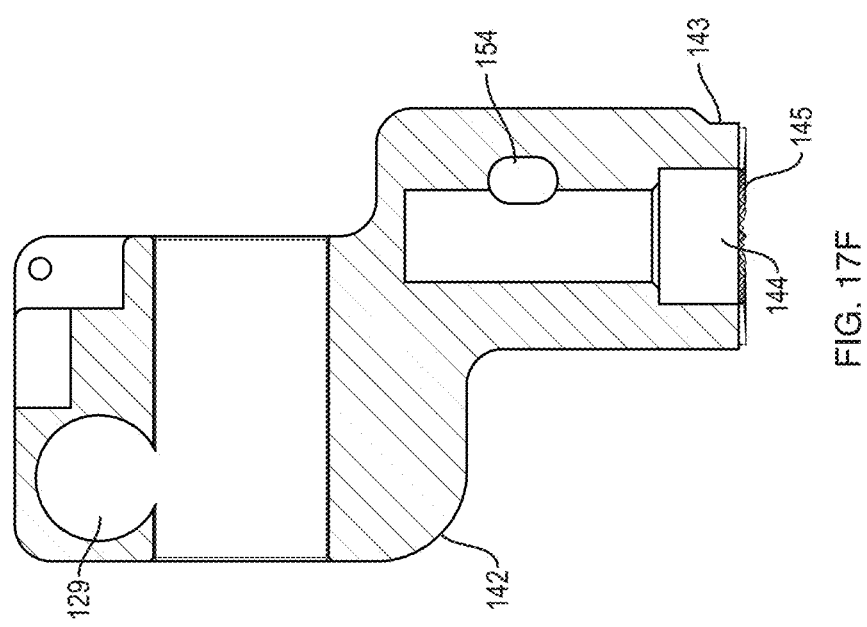
FIG. 17F

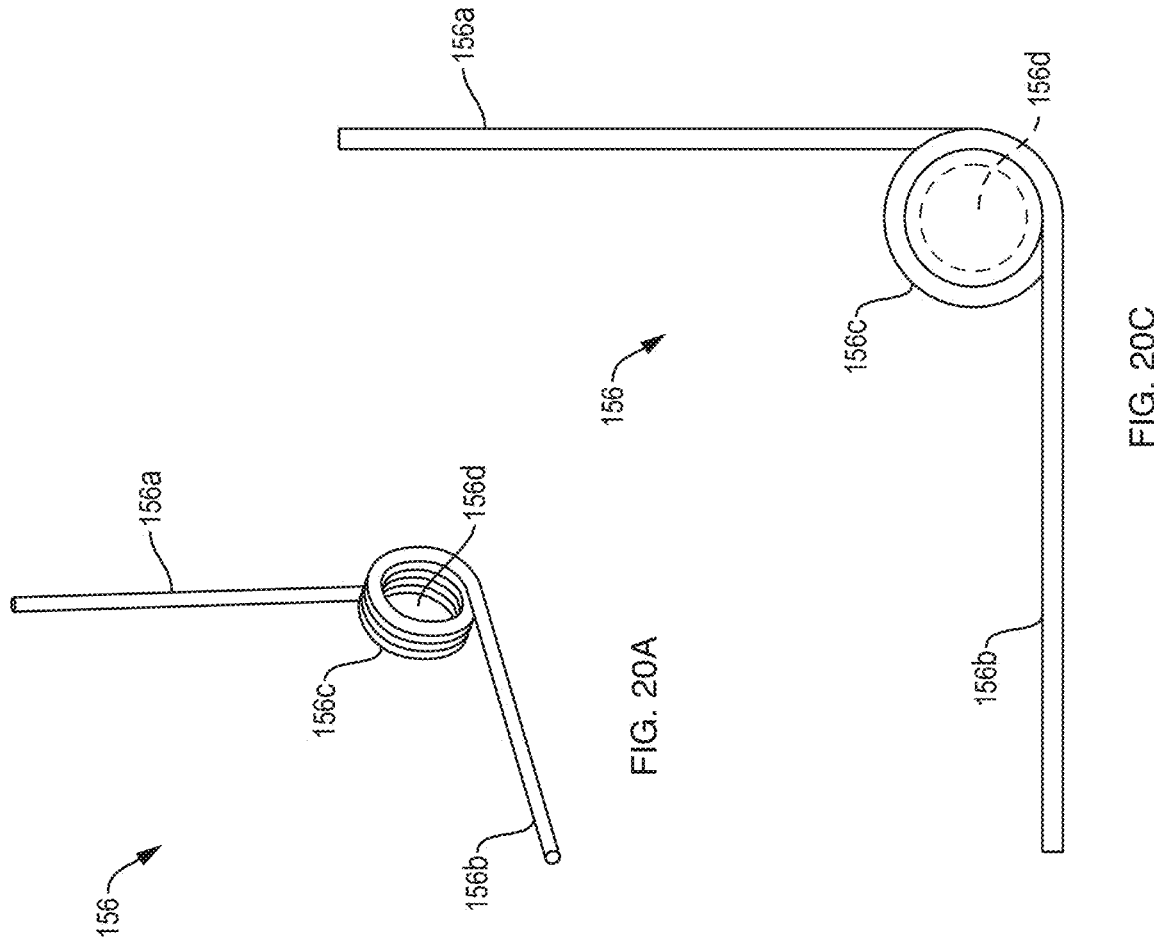
FIG. 20A
FIG. 20C
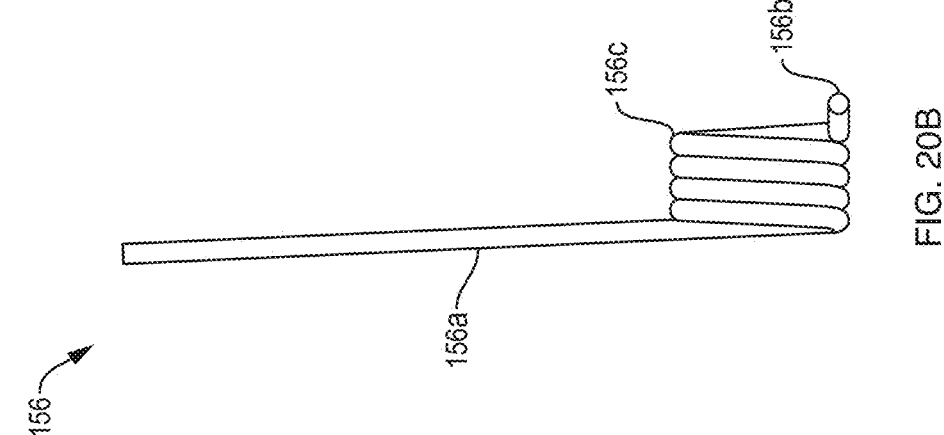
FIG. 20B

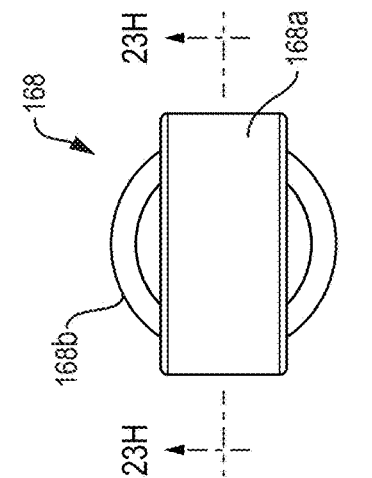
FIG. 23C
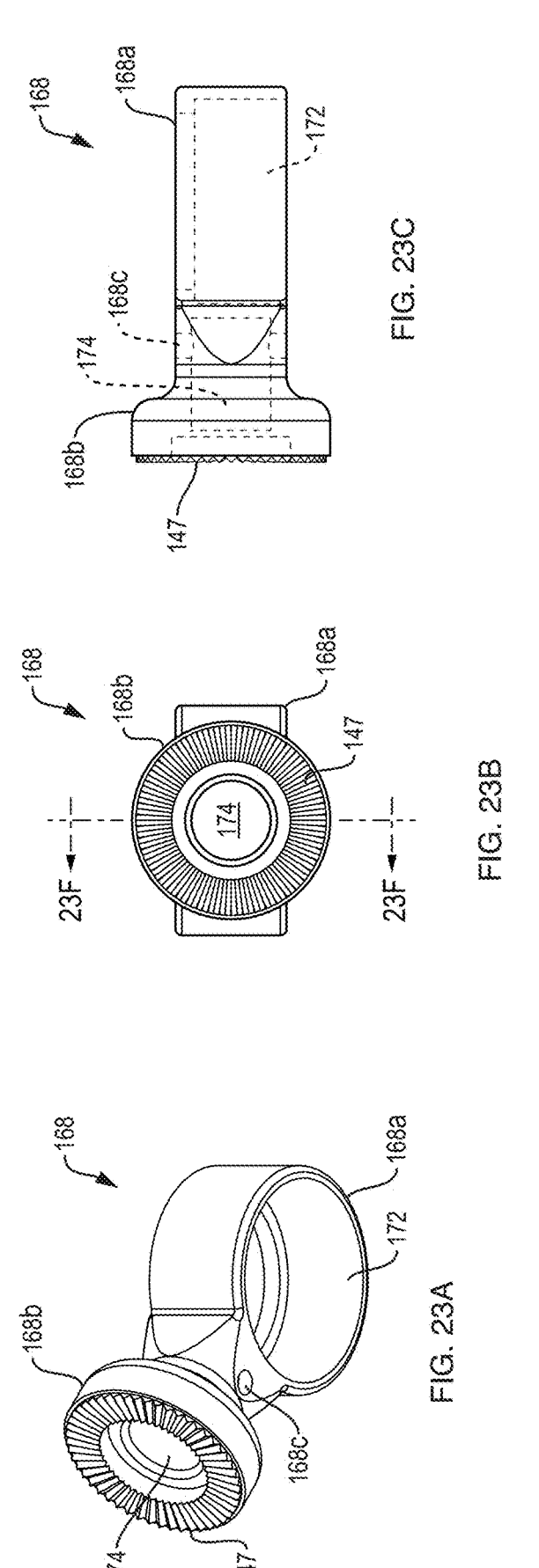
FIG. 23B
FIG. 23A
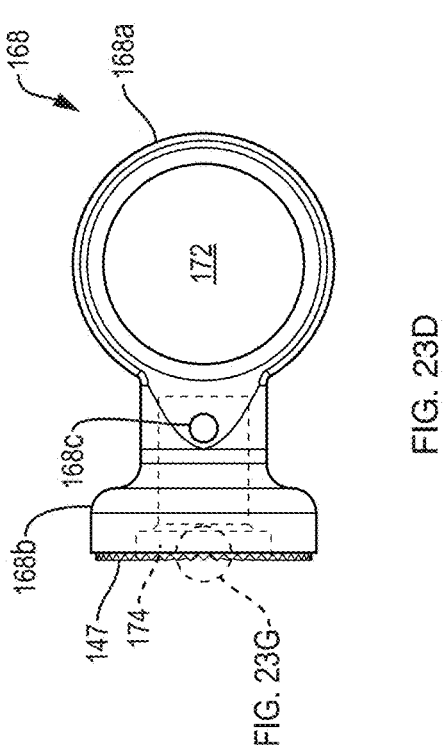
FIG. 23E
FIG. 23D

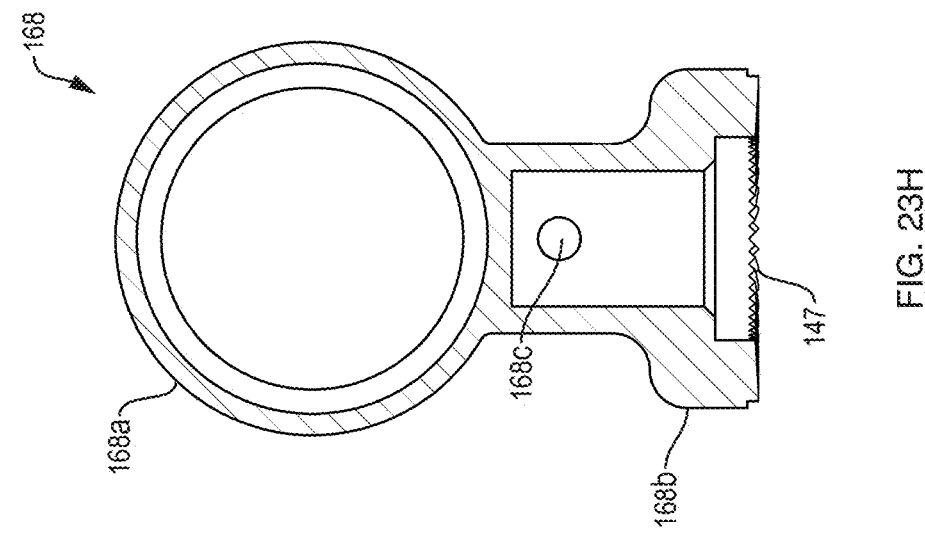
FIG. 23H
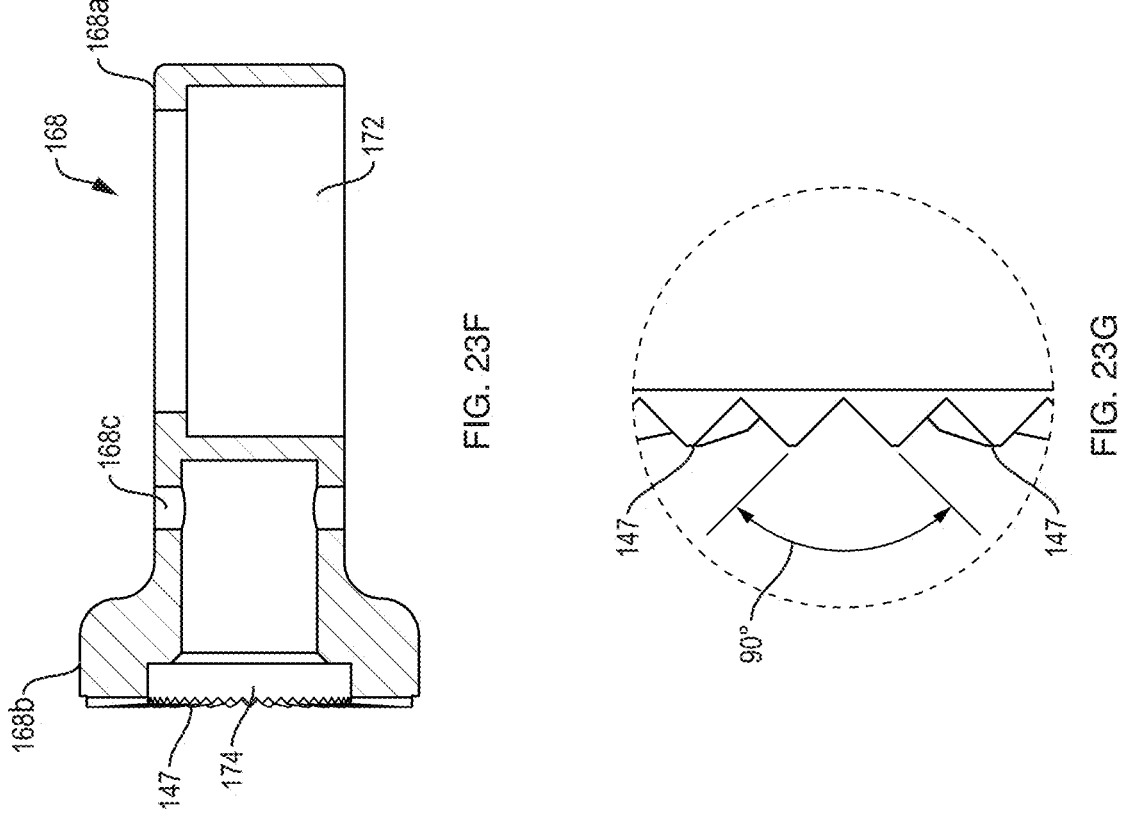
FIG. 23F
FIG. 23G

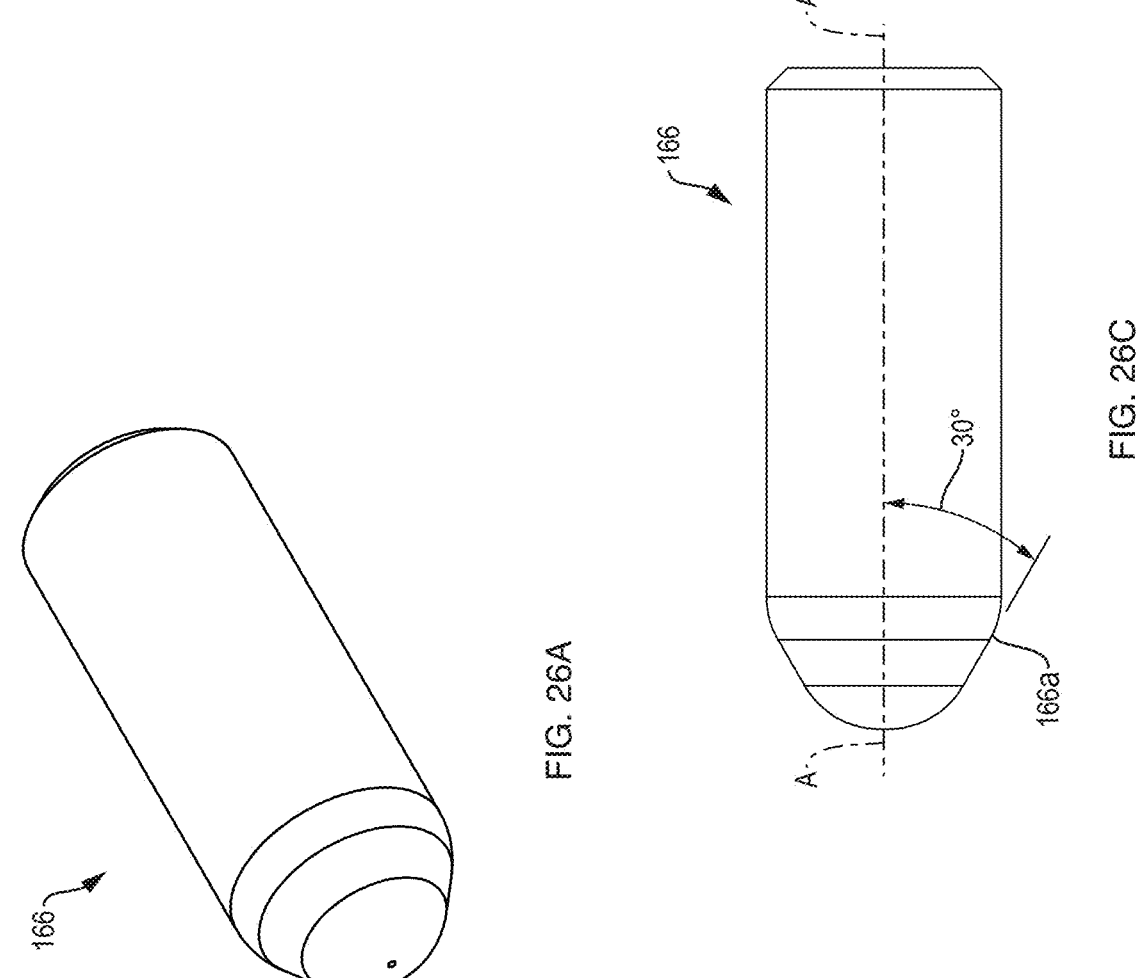
FIG. 26A
FIG. 26C
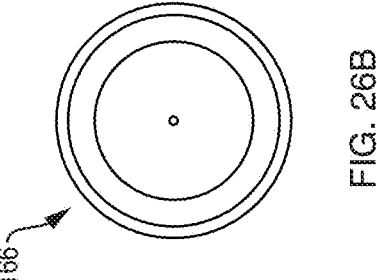
FIG. 26B

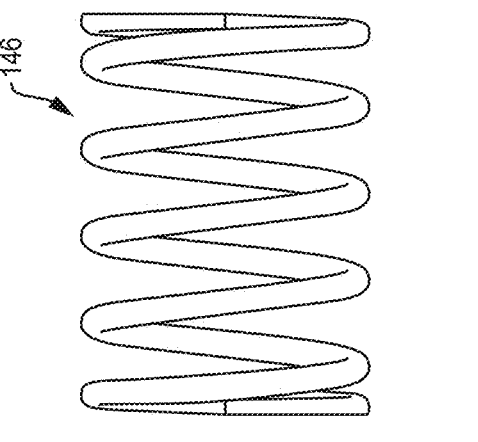
FIG. 27C
FIG. 27A
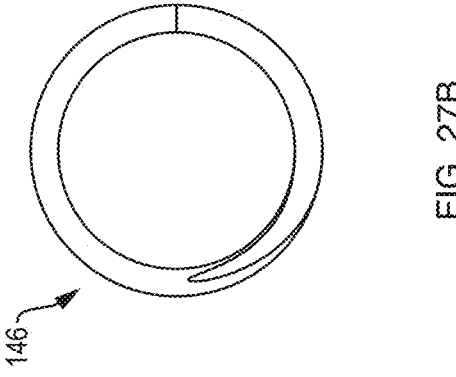
FIG. 27B

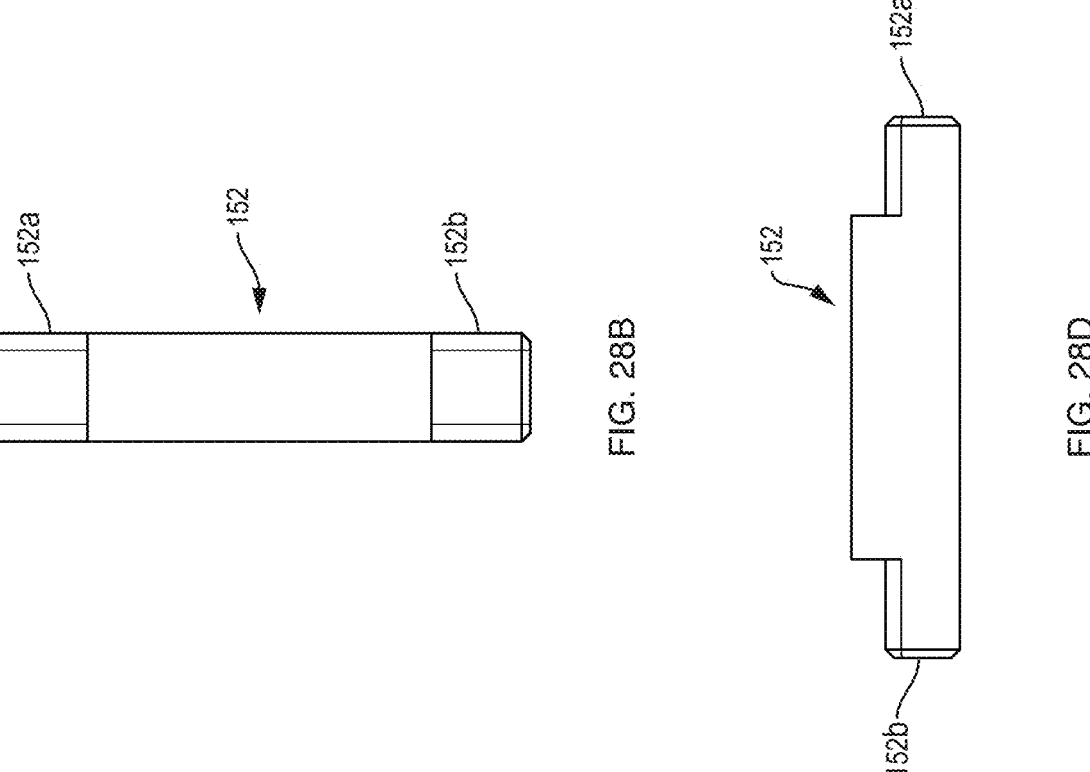
FIG. 28B
FIG. 28D
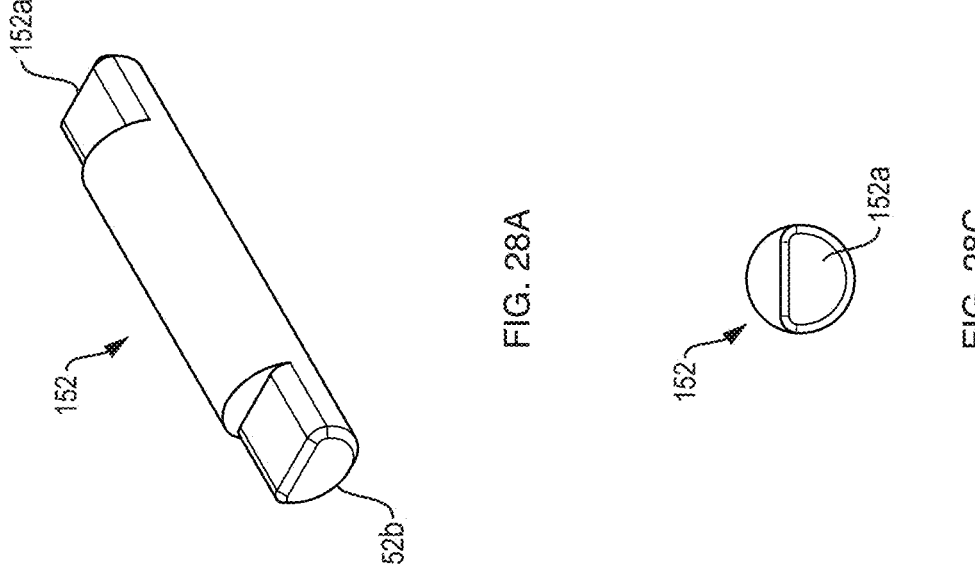
FIG. 28A
FIG. 28C

148d

103°

148c

23°

148

148a

148b

148

150

150a

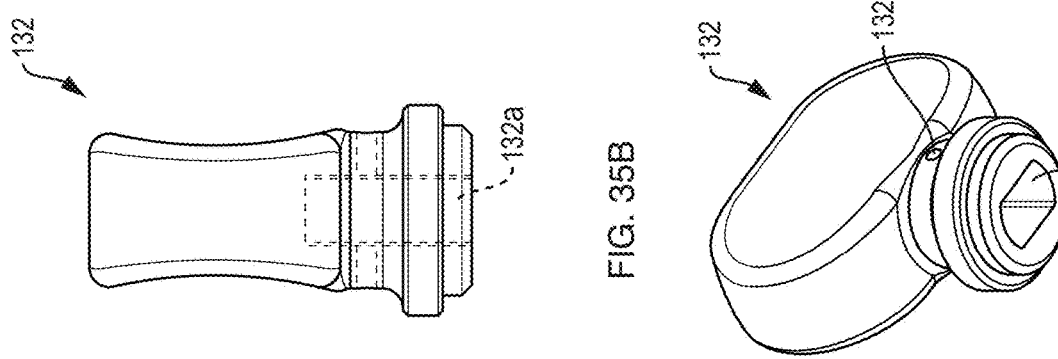
FIG. 35B
FIG. 35D
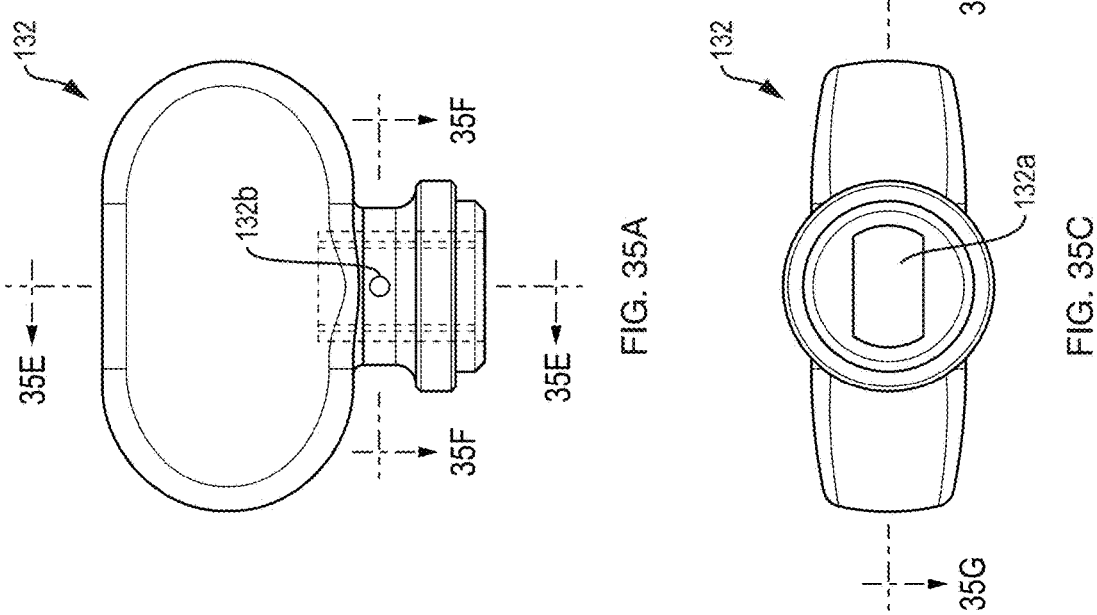
FIG. 35A
FIG. 35C

SYSTEMS AND METHODS FOR PRONE LATERAL SPINE SURGERY

CROSS REFERENCE TO RELATED APPLICATIONS

This application is a Continuation of U.S. application Ser. No. 18/555,208 filed Oct. 12, 2023, which is a National Phase filing under 35 U.S.C. § 371 of International Application No. PCT/US2023/060571 filed Jan. 12, 2023, which claims benefit from U.S. Provisional Patent Application Ser. No. 63/299,279, filed Jan. 13, 2022, and U.S. Provisional Patent Application Ser. No. 63/306,785, filed Feb. 4, 2022, all of which are incorporated by reference in their entireties.

STATEMENT REGARDING GOVERNMENT INTEREST

None.

BACKGROUND OF THE INVENTION

The present invention relates generally to spine surgery, and more particularly, to systems and methods for prone lateral spine surgery.

Prone lateral surgery to the thoracic and lumbar spine allows simultaneous anterior and posterior approaches to the spine without the need for changing patient position intra-operatively. This makes surgeries that might otherwise require an intraoperative flip more efficient while maintaining an equivalent safety profile.

Nevertheless, current approaches to prone lateral surgery do require work to be performed prior to patient positioning. A bolster is commonly positioned on the side opposite the surgeon to prevent patient and spine movement during the prone portion of the procedure.

Exemplary pre-surgical preparations for performing prone lateral surgery using existing and customary technique are shown in FIGS. 1A and 1B in which the patient has been prepared and draped, with a bolster on the patient's right side. This setup allows the surgeon access only to the left side of the patient's spine.

The use of a bolster has significant drawbacks. First, the surgeon and/or surgical staff must be available to position this bolster in a specific position before the patient is positioned. If the bolster is initially mispositioned, then the surgeon and staff may have to roll the patient when face-down or even roll the patient back off of the table. This can be frustrating and time-consuming, and may even lead to neurological injury if there is high-grade neural element compression. Second, the placement of a bolster limits a surgeon's access to the spine because the bolster covers up one side of the abdomen. A surgeon must therefore choose which side to access prior to positioning and cannot easily change to the other side if access to the spine from the open/pre-determined side is not possible. A surgeon cannot safely and efficiently access both sides of the patient's spine using current techniques.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

Various embodiments of the invention include an internal fixation system and a surgical method for prone lateral spine surgery that employs the internal fixation system. The surgical method does not require the use of a bolster to prevent patient and spine movement during the prone portion of the procedure, as bolsters have the aforementioned drawbacks.

In one embodiment, an internal fixation system for spinal surgery on a patient comprises a lateral lumbar interbody fusion (LLIF) retractor having an LLIF retractor adaptor; a posterior compressor/distractor; an A-arm configured to mount on a surgical table; and a B-arm configured to engage an end of the table-mounted A-arm and to engage the posterior compressor/distractor.

In another embodiment, an internal fixation system for spinal surgery on a patient comprises a lateral lumbar interbody fusion (LLIF) retractor having an LLIF retractor adaptor 118; a posterior compressor/distractor including a posterior distractor rack assembly including a rack having a plurality of ridges on at least one surface thereof; a posterior distractor carriage assembly configured to operably engage the posterior distractor rack assembly and including an opening configured to receive the rack therethrough; and a pinion assembly configured to operably engage the posterior distractor rack assembly and the posterior distractor carriage assembly. The posterior distractor rack assembly and posterior distractor carriage assembly are movable relative to one another.

In yet another embodiment, an internal fixation system for spinal surgery on a patient comprises at least two cannulated pedicle screws that are insertable through respective pedicles of the patient's spine; a distracting frame 20 configured to operably connect the at least two cannulated screws to each other; and means for mounting the internal fixation system to a surgical table.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 17F is a cross-sectional view of the carriage hub of FIGS. 17A and 17C, as taken along line 17F in FIG. 17C;

FIG. 17G is a detailed view of a portion of FIG. 17B, as denoted in dashed lines;

FIG. 17H is a detailed view of a portion of FIG. 17C, as denoted in dashed lines;

FIG. 20A is a top perspective view of a torsion spring for use with the ratchet pawl of FIG. 18A;

FIG. 20B is a front plan view of the torsion spring of FIG. 20A;

FIG. 20C is a side elevational view of the torsion spring of FIG. 20A;

FIG. 23A is a bottom perspective view of a swivel tube hub of the swivel tube subassembly of FIG. 21A;

FIG. 23B is a front elevational view of the swivel tube hub of FIG. 23A;

FIG. 23C is a side elevational view of the swivel tube hub of FIG. 23A;

FIG. 23D is a top plan view of the swivel tube hub of FIG. 23A;

FIG. 23E is a rear elevational view of the swivel tube hub of FIG. 23A;

FIG. 23F is a cross-sectional view of the swivel tube hub of FIGS. 23A and 23B, as taken along line 23F-23F in FIG. 23B;

FIG. 23G is a detailed view of a portion of FIG. 23B, as denoted in dashed lines;

FIG. 23H is a cross-sectional view of the swivel tube hub of FIGS. 23A and 23E, as taken along line 23H-23H in FIG. 23E;

FIG. 26A is a top perspective view of a swivel tube tulip rod of the swivel tube subassembly of FIG. 21A;

FIG. 26B is a front elevational view of the swivel tube tulip rod of FIG. 26A;

FIG. 26C is a side elevational view of the swivel tube tulip rod of FIG. 26A;

FIG. 27A is a top perspective view of a compression spring of the swivel tube subassembly of FIG. 21A;

FIG. 27B is a front elevational view of the compression spring of FIG. 27A;

FIG. 27C is a side elevational view of the compression spring of FIG. 27A;

FIG. 28A is a top perspective view of a cam pin of the posterior distractor carriage assembly of FIG. 15A;

FIG. 28B is a front elevational view of the cam pin of FIG. 28A;

FIG. 28C is a top plan view of the cam pin of FIG. 28A;

FIG. 28D is a side elevational view of the cam pin of FIG. 28A;

FIG. 35D is a bottom perspective view of the knob of FIG. 35A;

FIG. 35E is a cross-sectional view of the knob of FIG. 34A, as taken along line 35E-35E in FIG. 35A;

FIG. 35F is a cross-sectional view of the knob of FIG. 34A, as taken along line 35F-35F in FIG. 35A;

FIG. 35G is a cross-sectional view of the knob of FIGS. 34A and 34C, as taken along line 35G-35G in FIG. 35C;

FIG. 36A is a top perspective view of a gear of the pinion assembly of FIG. 33A;

FIG. 36B is a front elevational view of the gear of FIG. 36A;

FIG. 36C is a side elevational view of the gear of FIG. 36A;

FIG. 37A is a top perspective view of a pin of the pinion assembly of FIG. 33A;

FIG. 37B is a front plan view of the pin of FIG. 36A; and
FIG. 37C is a side elevational view of the pin of FIG. 36A.

DETAILED DESCRIPTION

Figure 1A:
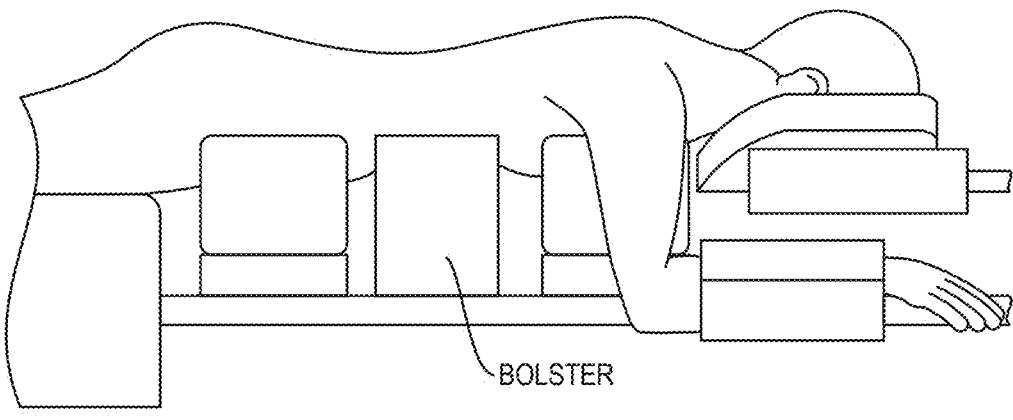
FIG. 1A is a schematic illustration of an exemplary pre-surgical preparation for performing prone lateral surgery on a patient using existing and customary technique, showing a bolster on the patient's right side.
Figure 1B:
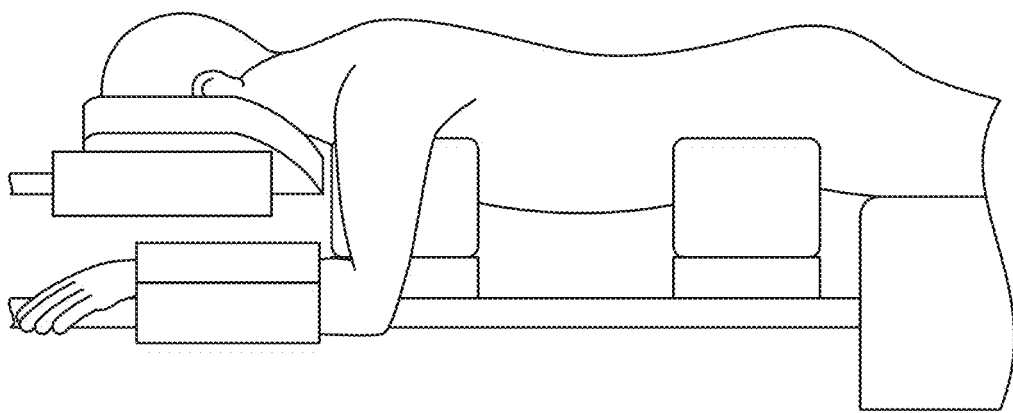
FIG. 1B is a schematic illustration of the exemplary pre-surgical preparation shown in FIG. 1A, showing the patient's left side to which the surgeon has access (i.e., without the bolster)

The subject innovation is now described with reference to
the drawings, wherein like reference numerals are used to
refer to like elements throughout. In the following descrip-
tion, for purposes of explanation, numerous specific details
are set forth in order to provide a thorough understanding of
the present invention. It may be evident, however, that the
present invention may be practiced without these specific
details.

Disclosed herein are internal fixation systems and meth-
ods for prone lateral spine surgery without the use of a
bolster.

Eliminating the bolster from prone lateral spine surgery
would save time and allow the surgeon to access either side
of the spine in the same patient without repositioning. This
is especially advantageous for patients with multilevel disc
degeneration and a secondary scoliotic deformity, as often-
times in these patients it is easier to access different levels
from one side or the other.

To eliminate the bolster, internal fixation systems accord-
ing to the present invention are employed to control spine
motion directly.

Advantageously, the internal fixation systems of the pres-
ent invention facilitate a surgical approach from both the
patient's right side and left side.

The internal fixation systems of the present invention also
provide a gentler and safer way for a surgeon to manipulate
the patient's spine, and to distract across the patient's disc
space.

Further, the internal fixation systems of the present inven-
tion facilitate more stability and eliminate steps of surgery,
providing more space and improved visibility for the sur-
geon.

Figure 2:
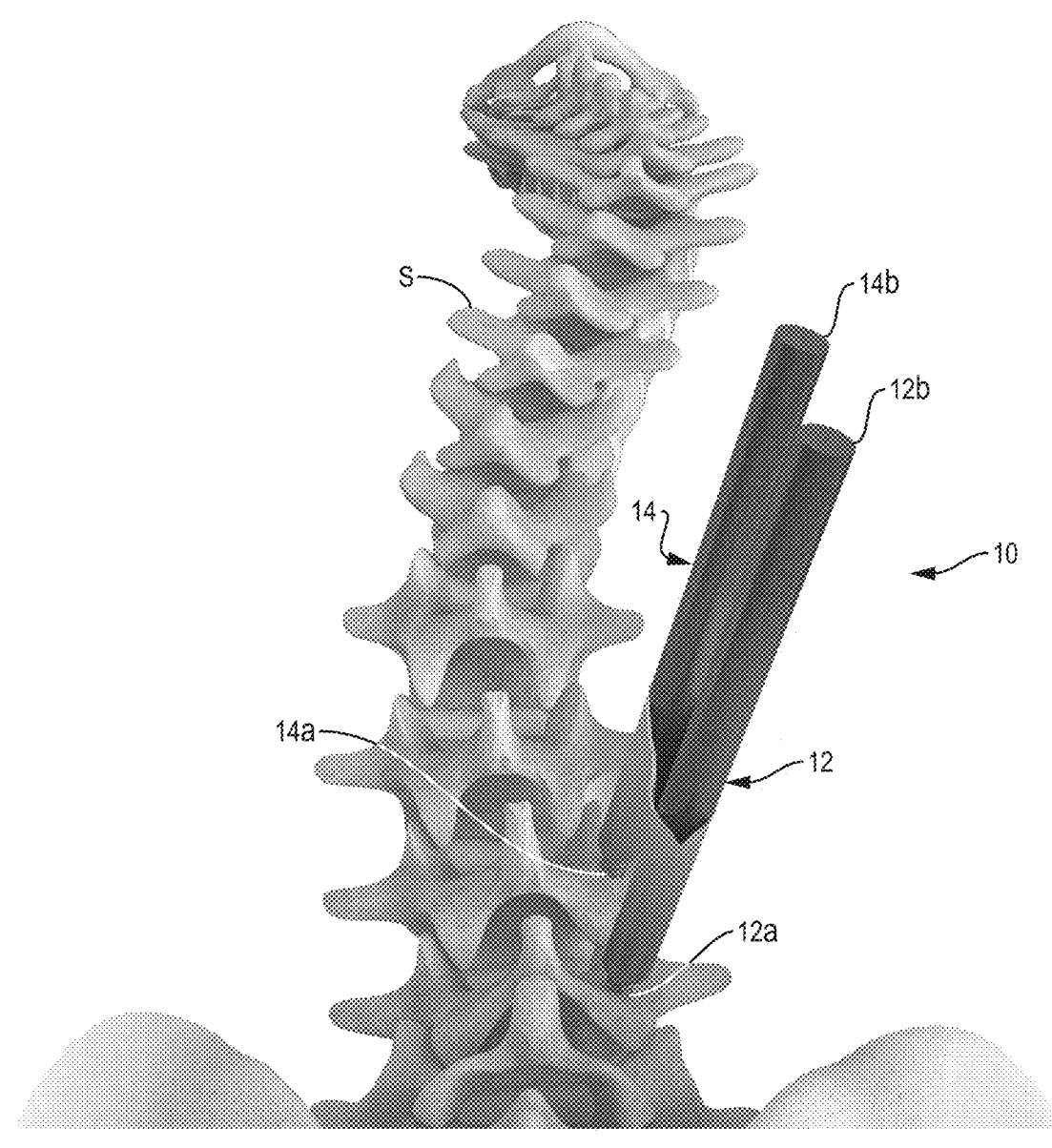
FIG. 2 is a schematic illustration of the placement of cannulated posts of an internal fixation system according to a first embodiment of the present invention being inserted into a patient's spine during surgery
Figure 3:
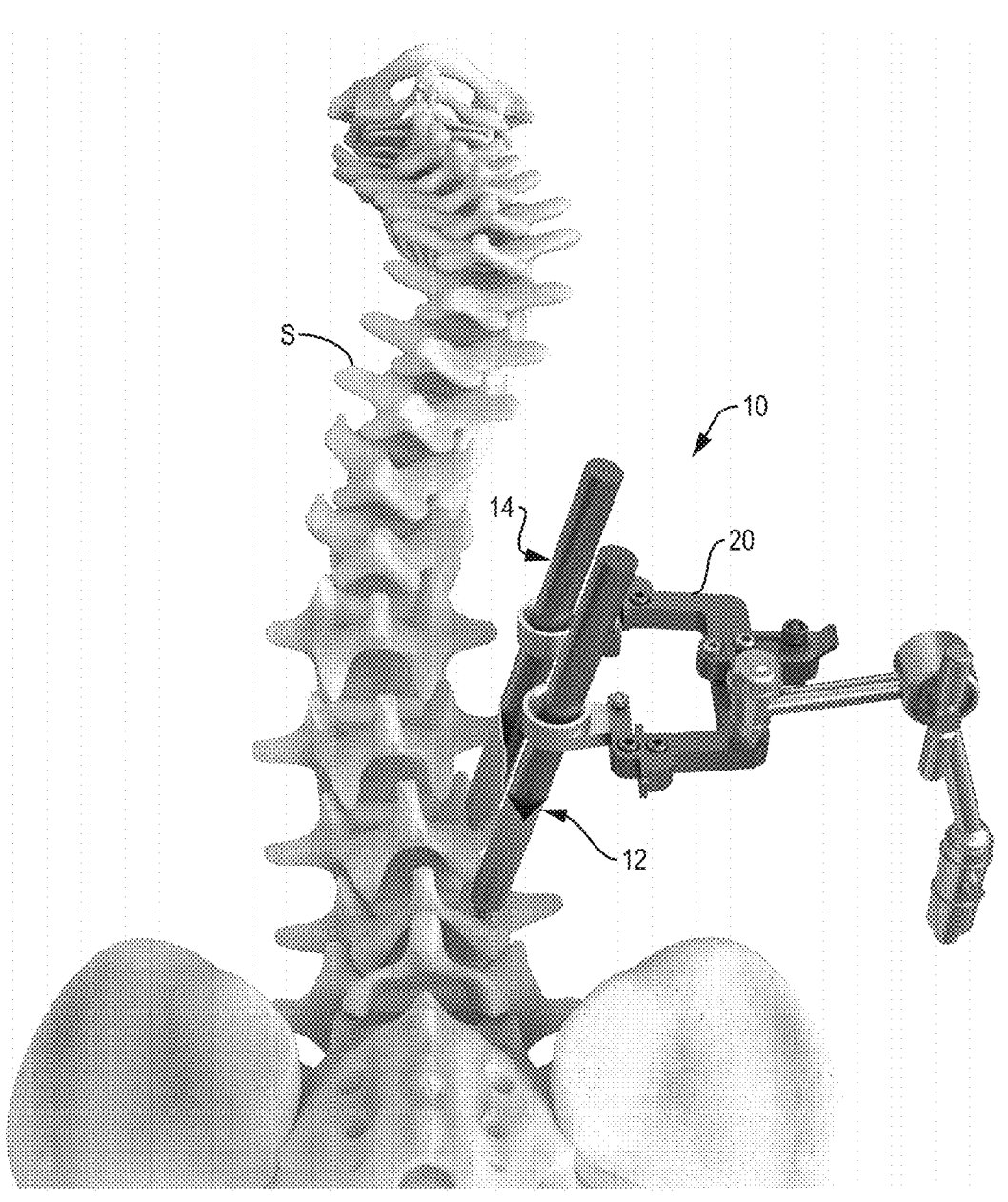
FIG. 3 is a top environmental view of the internal fixation system of FIG. 2 in use during a prone lateral spine surgery according to the present invention.
Figure 4:
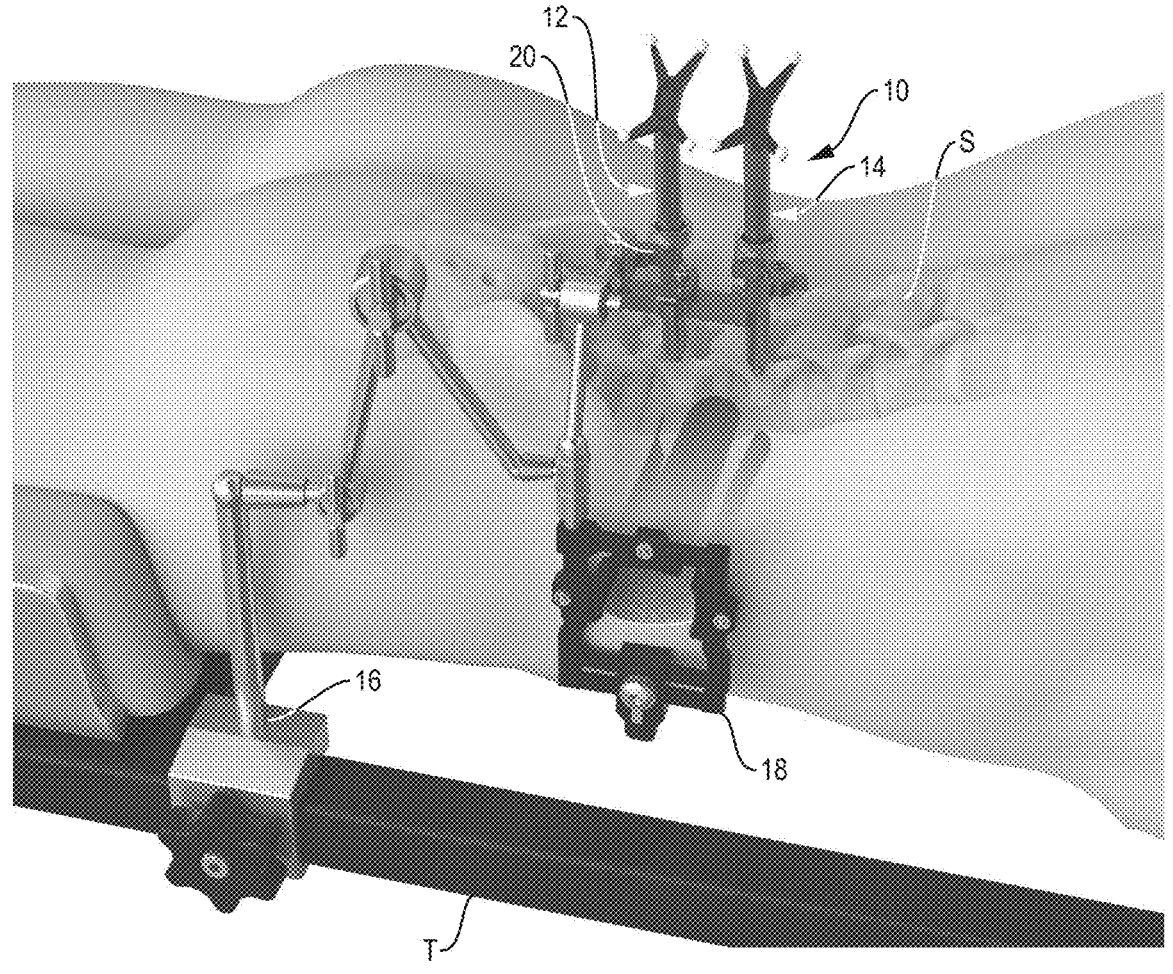
FIG. 4 is a top environmental view of the internal fixation system of FIG. 2 in use with a lateral retractor during a prone lateral spine surgery according to the present invention, wherein the lateral retractor and a distractor of the internal fixation system are connected.

An internal fixation system 10 according to a first embodi-
ment of the present invention is shown in FIGS. 2-4. The
internal fixation system 10 includes at least two cannulated
posts 12, 14 having respective distal ends 12a, 14a and
proximal ends 12b, 14b. The distal ends 12a, 14a are
configured to be inserted through respective pedicles of the
patient's spine S, as illustrated in FIGS. 2-4. As illustrated
in FIG. 4, this internal fixation system 10 is mounted directly
to a surgical table T using a table mount 16 (or other
mounting means) that is also used to position a lateral
retractor 18 for prone spine access. By connecting the lateral
retractor 18 to screws internally fixated into bone (i.e., the
patient's spine), the lateral retractor 18 becomes more stable,
minimizing retractor motion and providing additional
mechanical advantage.

In this embodiment, a surgeon first inserts a guidewire
into the patient's vertebrae bone using fluoroscopic or
stereotactic navigation guidance. The surgeon then inserts a
cannulated post over the guidewire.

The cannulated posts 12, 14 are then operably connected
to each other at or near their respective proximal ends using
an actively- and passively-distracting frame 20 (see FIGS. 3
and 4).

Before or during discectomy work, active distraction can
be utilized to minimize the risk of endplate violation. During
a trialing step, when the disc space is being expanded to
select the proper size implant, the distracting frame 20 will
progressively expand in both height and in relative angula-
tion and maintain that distraction after the trial is removed.
The use of a distractor during the disc preparation, trialing, and implant insertion portions of a lateral interbody fusion
procedure will decrease the risk of endplate violation and
implant subsidence. By reducing subsidence, for aminal
height is better maintained.

Intraoperatively, the change in angulation and position of
the cannulated posts 12, 14 can be interpreted through
stereotactic navigation to indicate to the surgeon how sig-
nificantly the patient's global and segmental spinal align-
ment has changed.

After the prone lateral surgery is performed, if posts have
been used, the cannulated posts 12, 14 are cannulated with
a guidewire, removed, and replaced with cannulated pedicle
screws (i.e., the cannulated screws shown implanted in
FIGS. 5 and 6), as are typically implanted in the course of
prone lateral surgery. Screw towers may be used with the
cannulated pedicle screws to facilitate their implantation,
after which the screw towers are removed.

Figure 5:
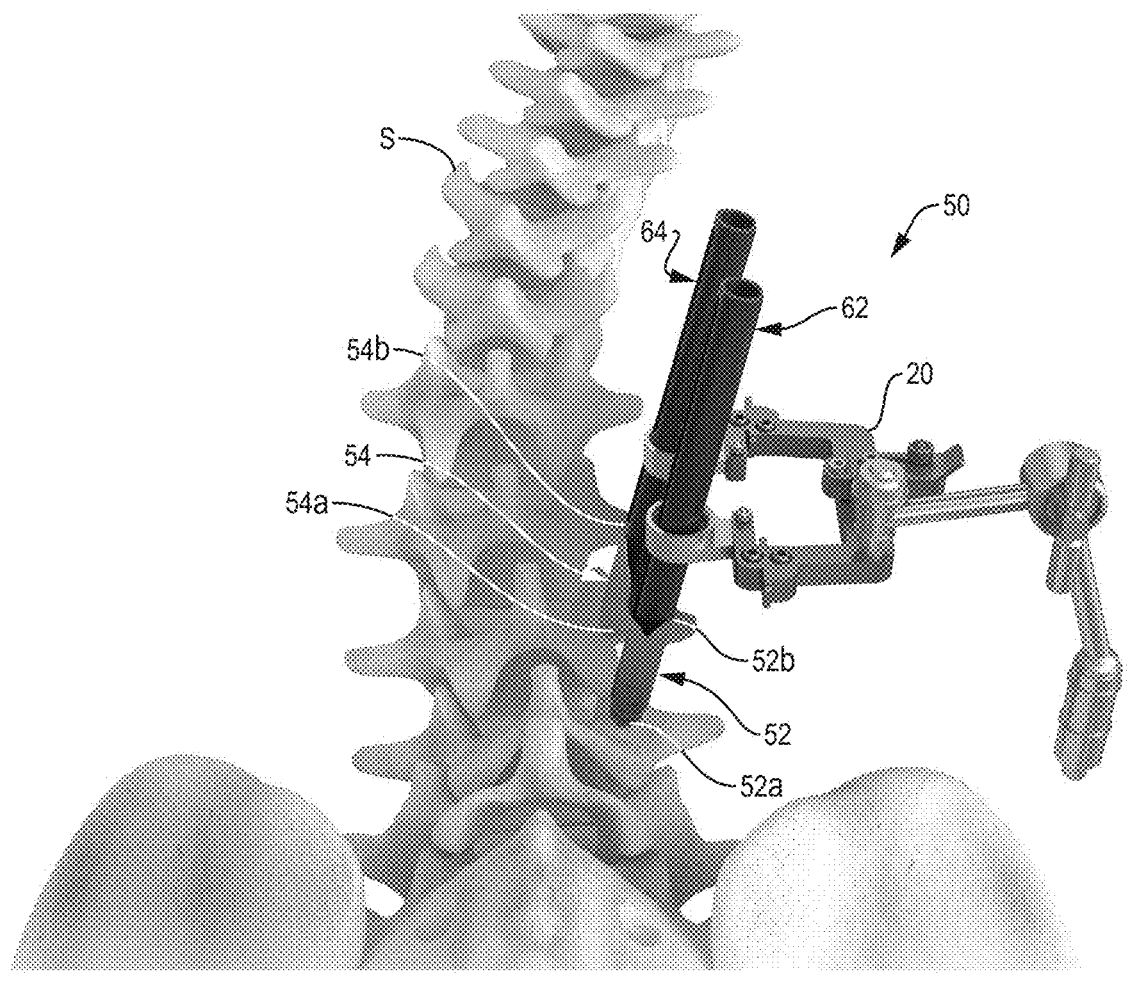
FIG. 5 is a top environmental view of the placement of cannulated pedicle screws of an internal fixation system according to a second embodiment of the present invention into a patient's spine during surgery.
Figure 6:
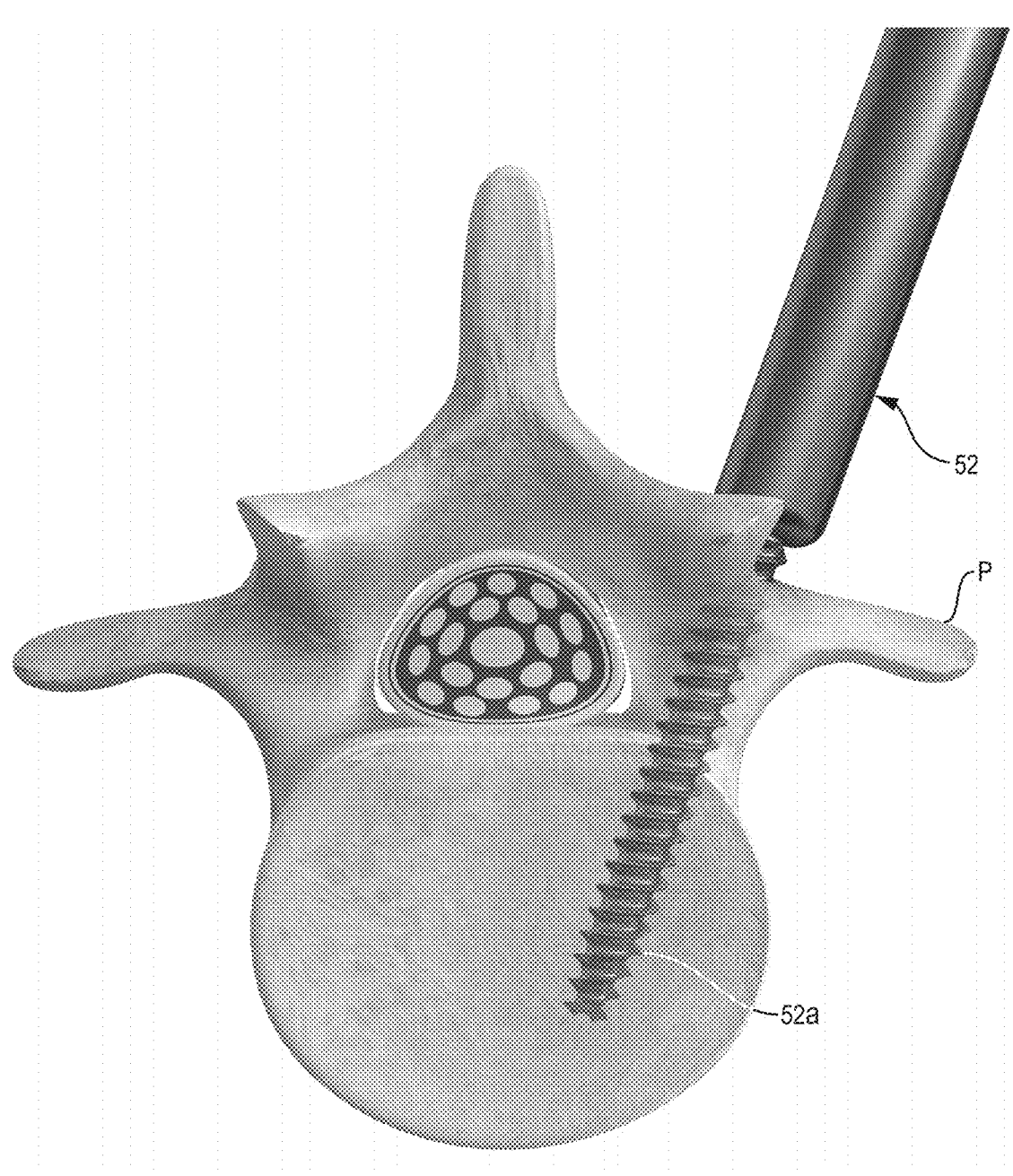
FIG. 6 is a detailed view of FIG. 5, showing the distal end of the cannulated pedicle screw inserted within a patient's vertebral body.
Figure 7:
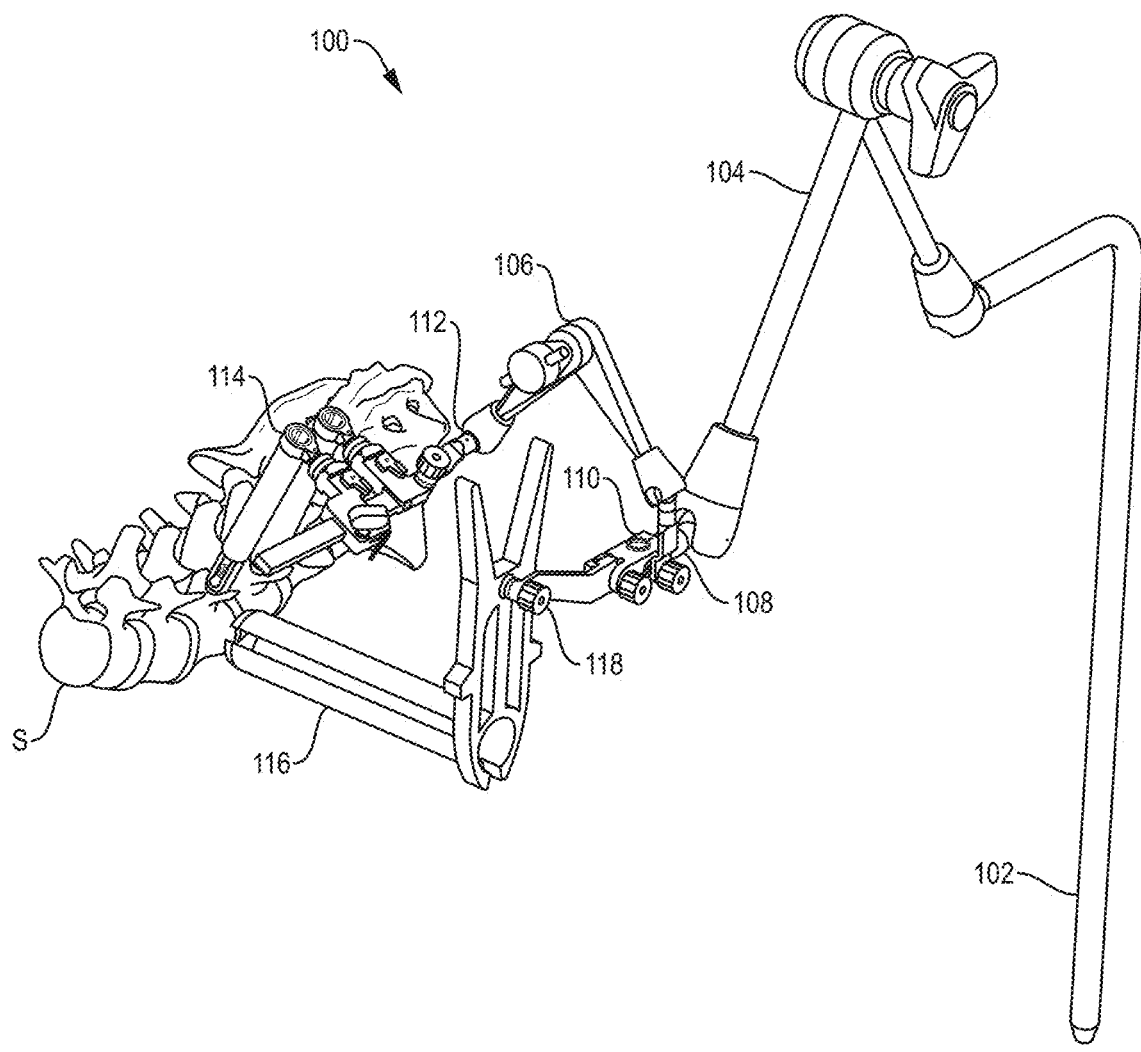
FIG. 7 is a top perspective view of an internal fixation system according to a third embodiment of the present invention in use with a patient's spine during surgery.
Figure 8:
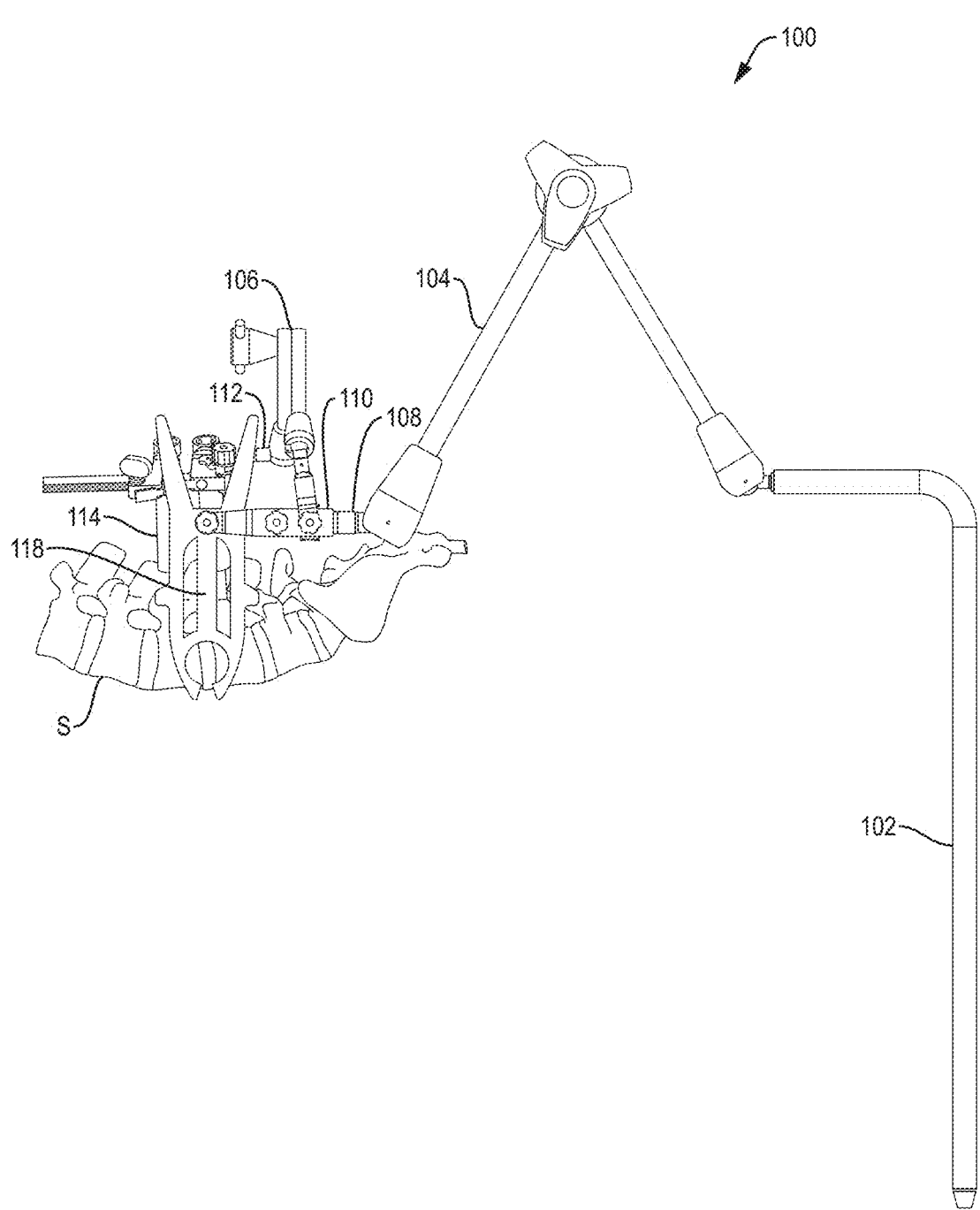
FIG. 8 is a left lateral view of the internal fixation system of FIG. 7.
Figure 9:
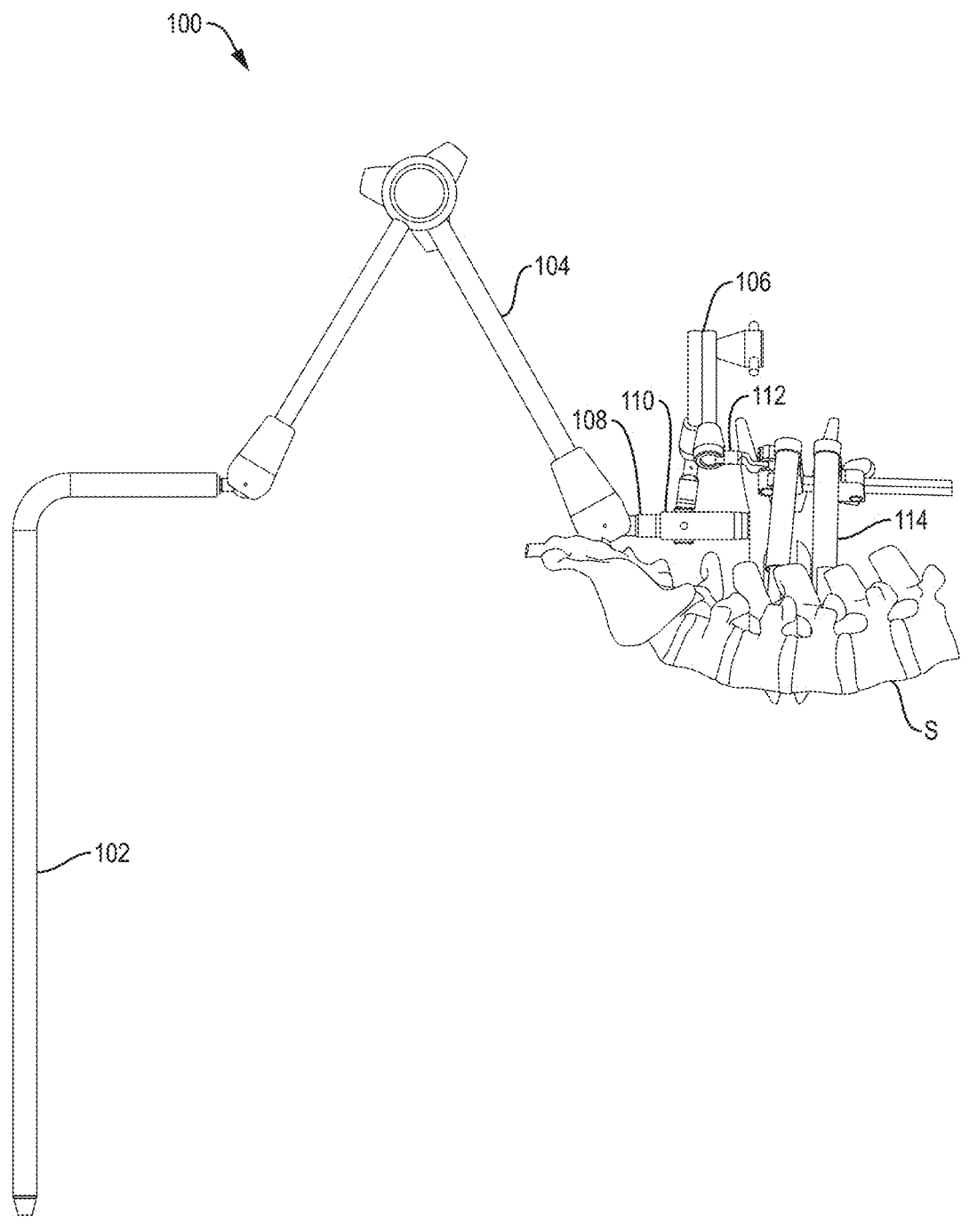
FIG. 9 is a right lateral view of the internal fixation system of FIG. 7.
Figure 10:
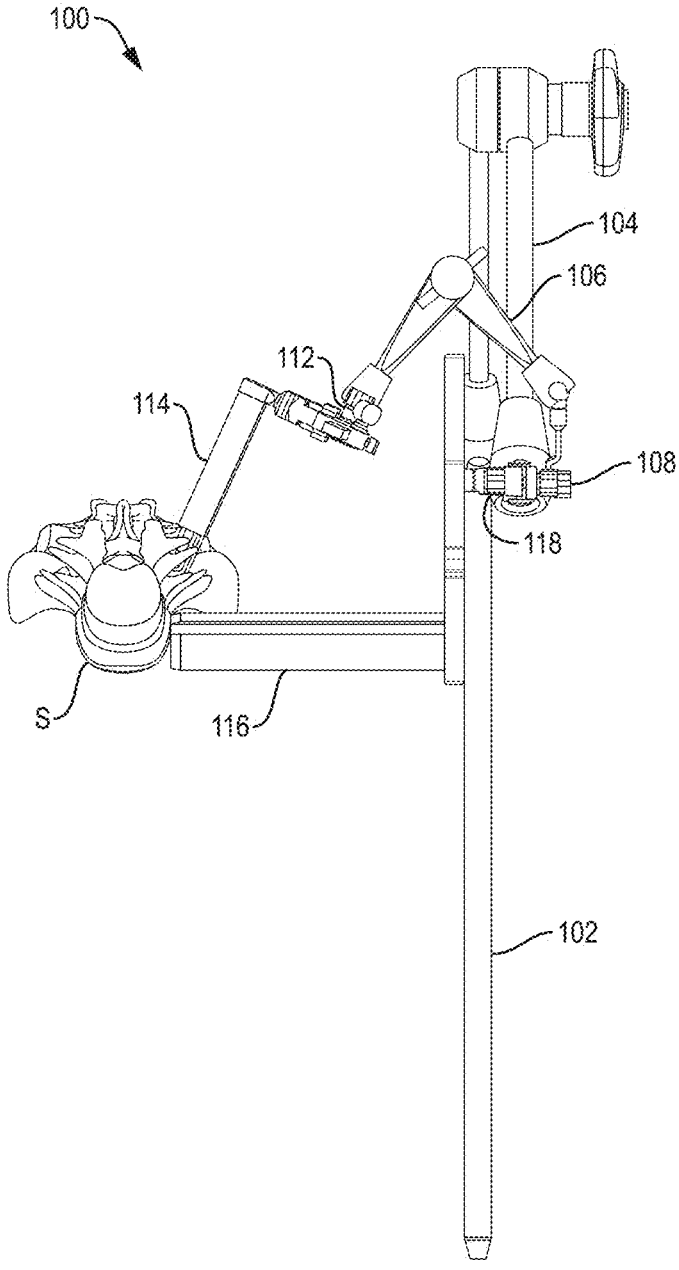
FIG. 10 is a cephalad-to-caudal view of the internal fixation system of FIG. 7.
Figure 11:
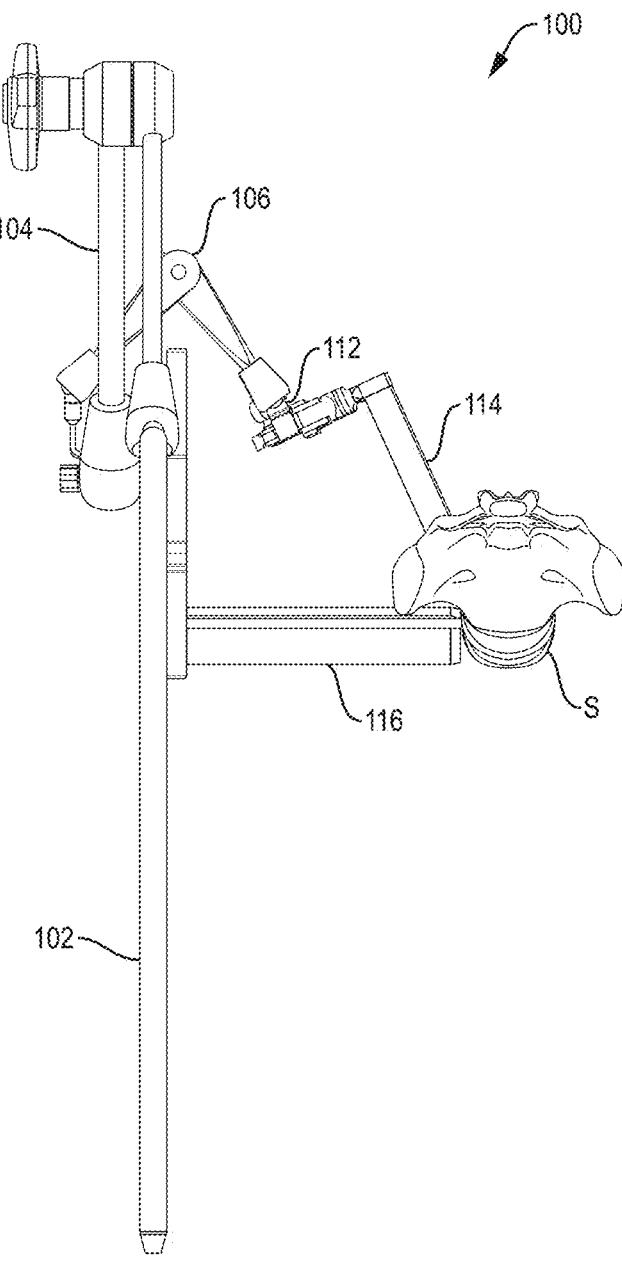
FIG. 11 is a caudal-to-cephalad view of the internal fixation system of FIG. 7.
Figure 12:
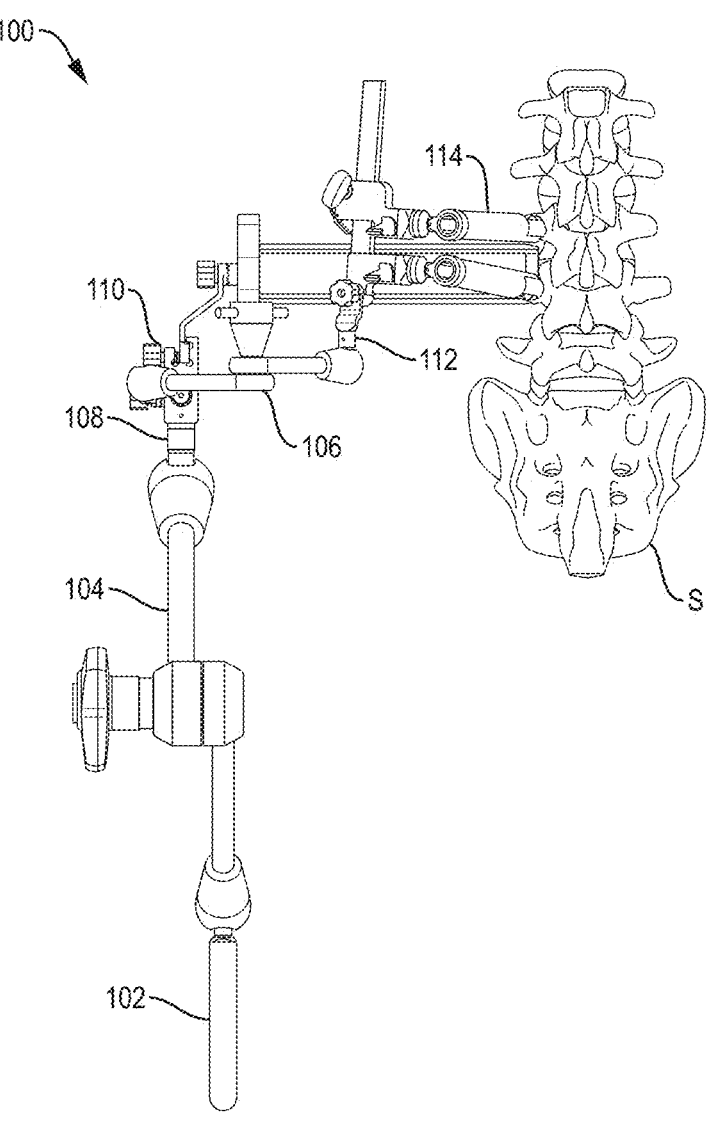
FIG. 12 is a posterior view of the internal fixation system of FIG. 7.
Figure 13:
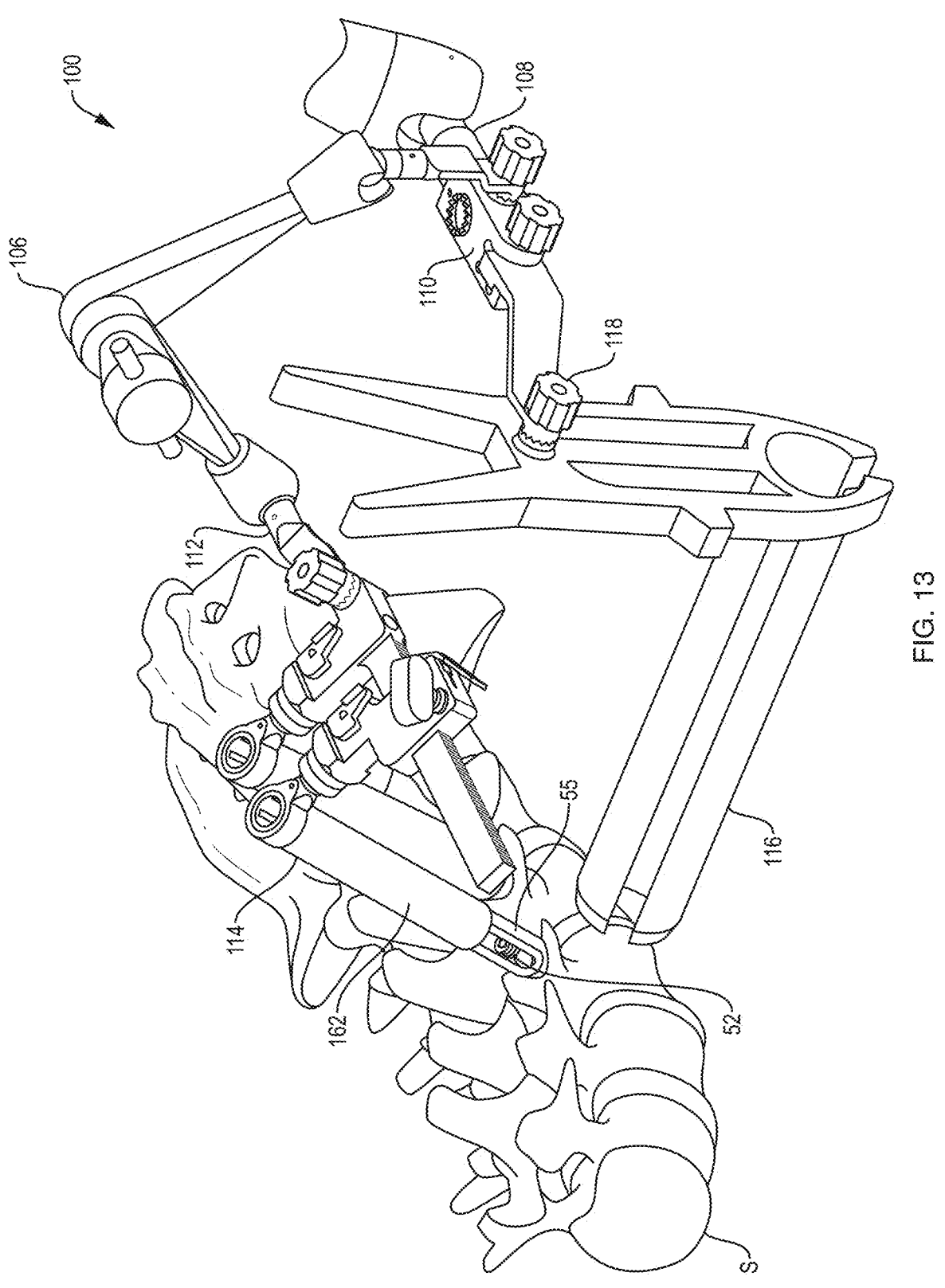
FIG. 13 is a top perspective view of the internal fixation system of FIG. 7.
Figure 13A:
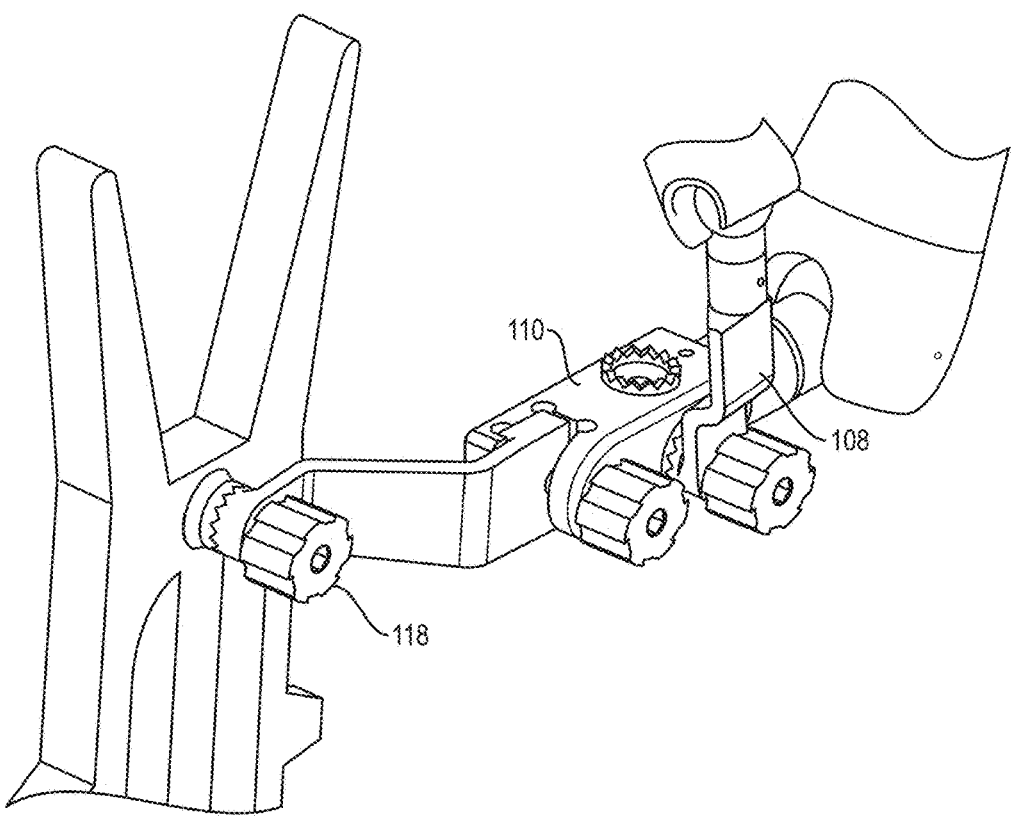
FIG. 13A is a detailed view of a first portion of FIG. 13.
Figure 13B:
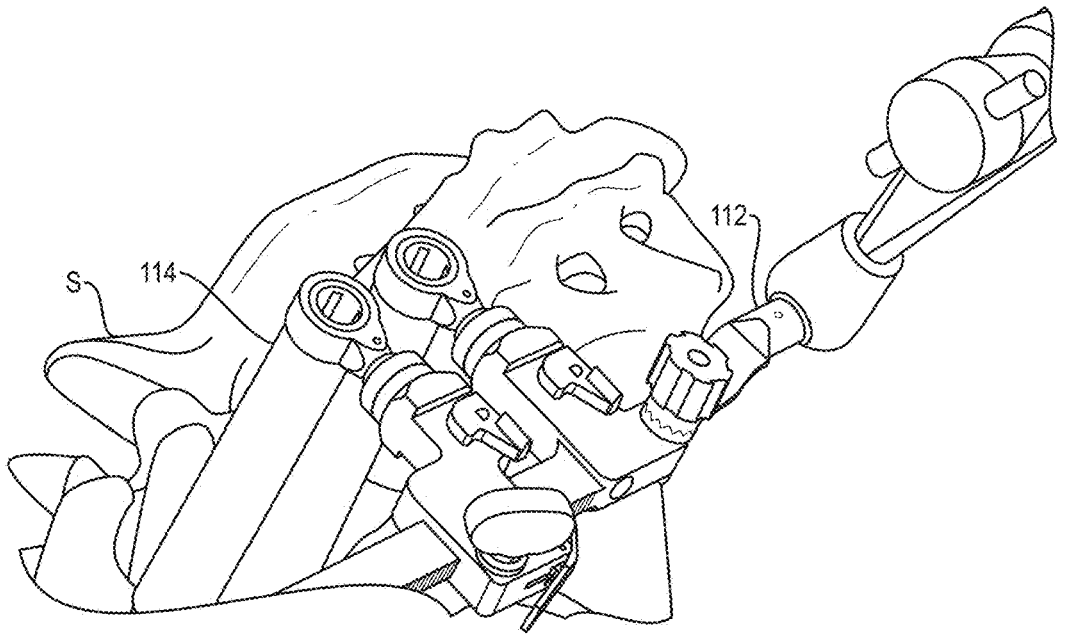
FIG. 13B is a detailed view of a second portion of FIG. 13.
Figure 14A:
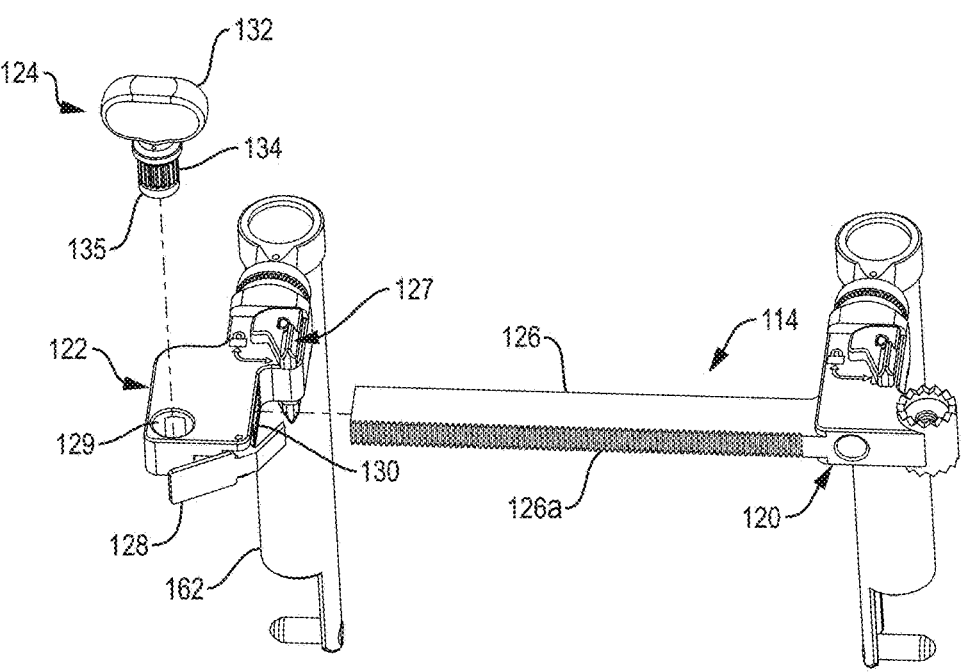
FIG. 14A is a top perspective exploded view of a posterior compressor/distractor of the internal fixation system of FIG. 7.
Figure 14B:
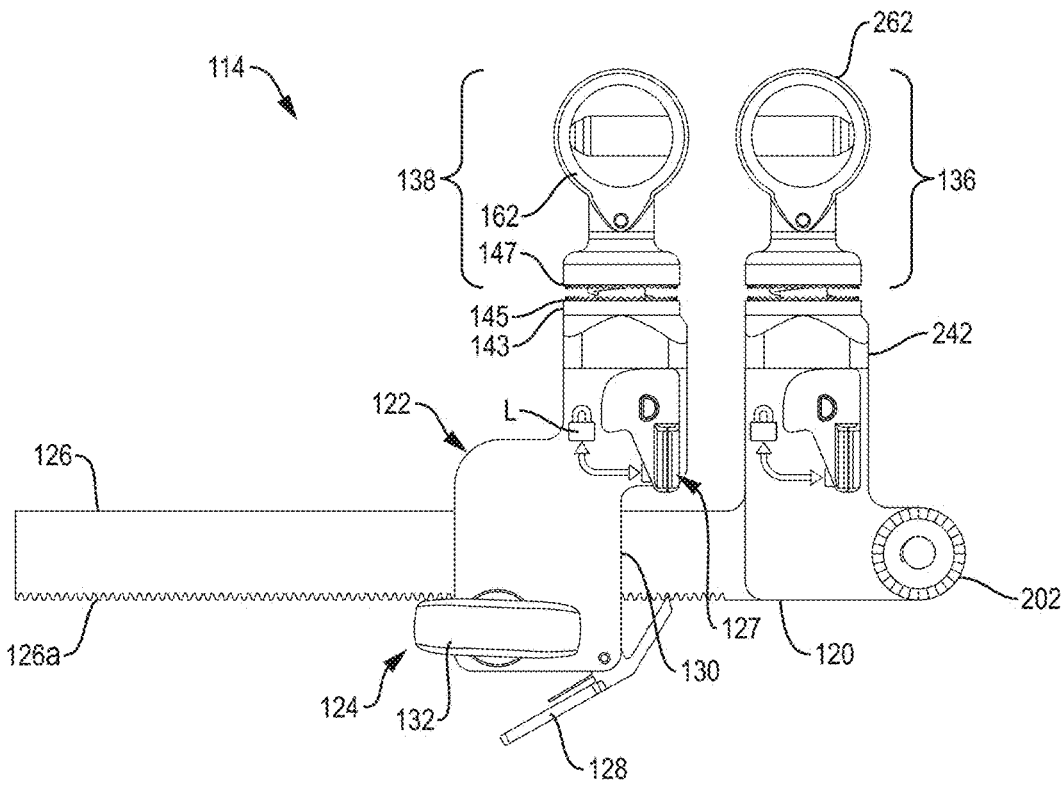
FIG. 14B is a top plan view of the posterior compressor/distractor of the internal fixation system of FIG. 7.
Figures 14C, 14D:
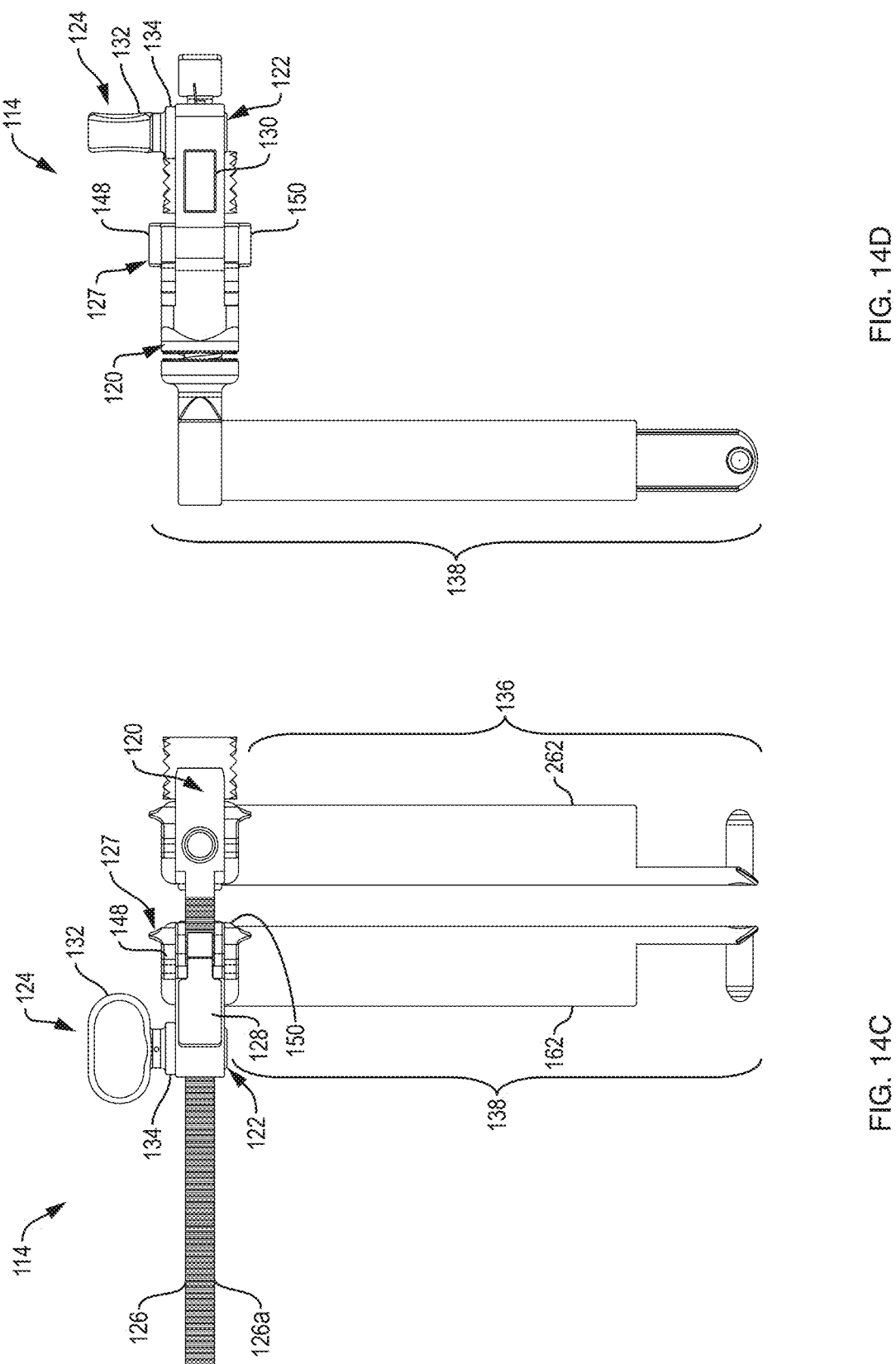
FIG. 14C is a front elevational view of the posterior compressor/distractor of the internal fixation system of FIG. 7.
FIG. 14D is a side elevational view of the posterior compressor/distractor of the internal fixation system of FIG. 7.
Figure 15A:
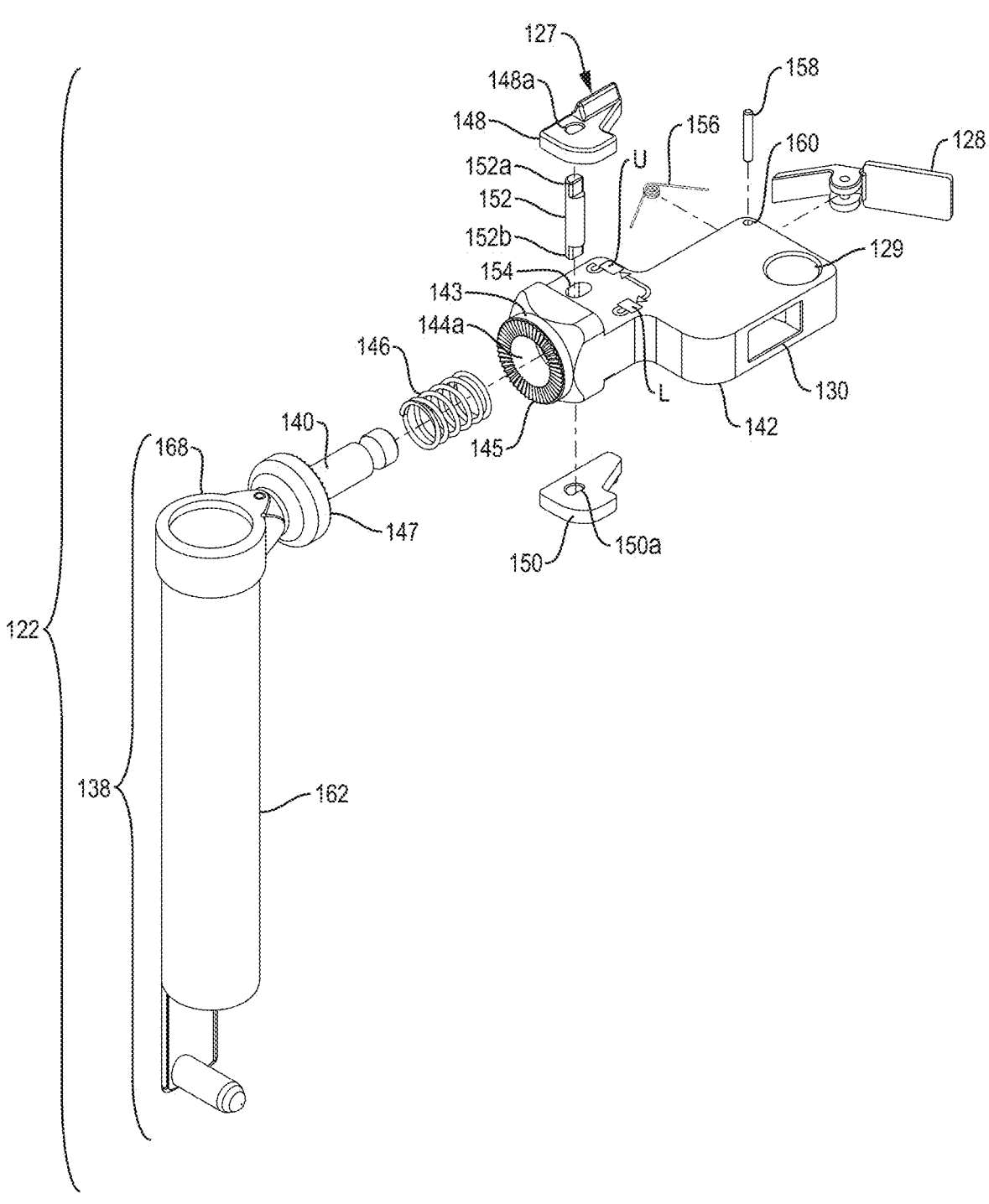
FIG. 15A is a top perspective exploded view of a posterior distractor carriage assembly of the posterior compressor/distractor of FIG. 14A.
Figure 15B:
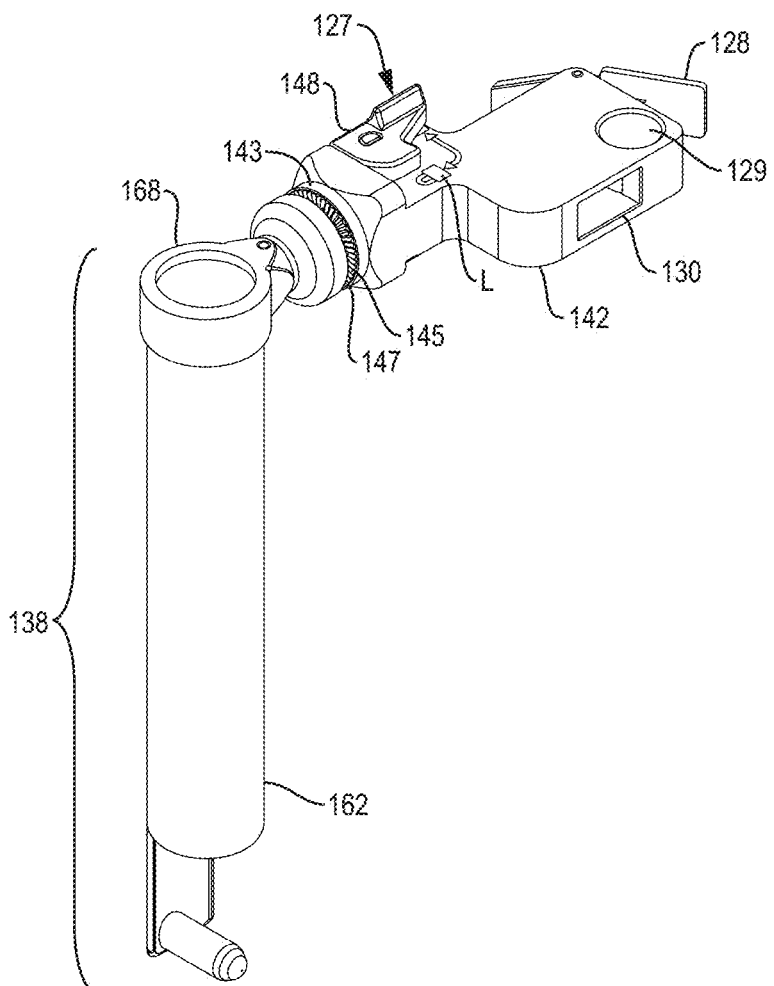
FIG. 15B is a top perspective view of the posterior distractor carriage assembly of FIG. 15A, as assembled.
Figure 15C:
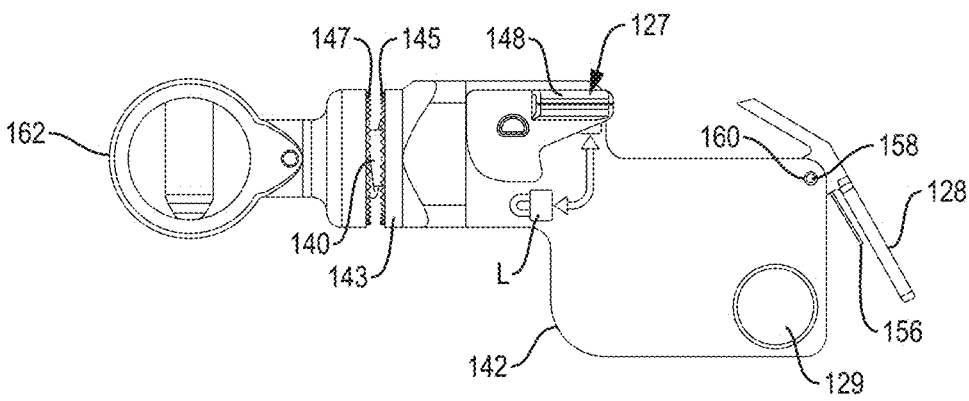
FIG. 15C is a top plan view of the posterior distractor carriage assembly of FIG. 15A.
Figure 15E:
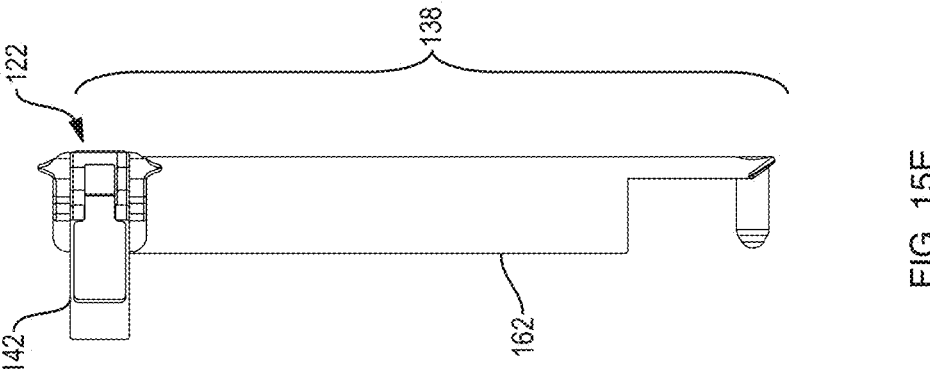
FIG. 15E is a side elevational view of the posterior distractor carriage assembly of FIG. 15A.
Figure 15D:
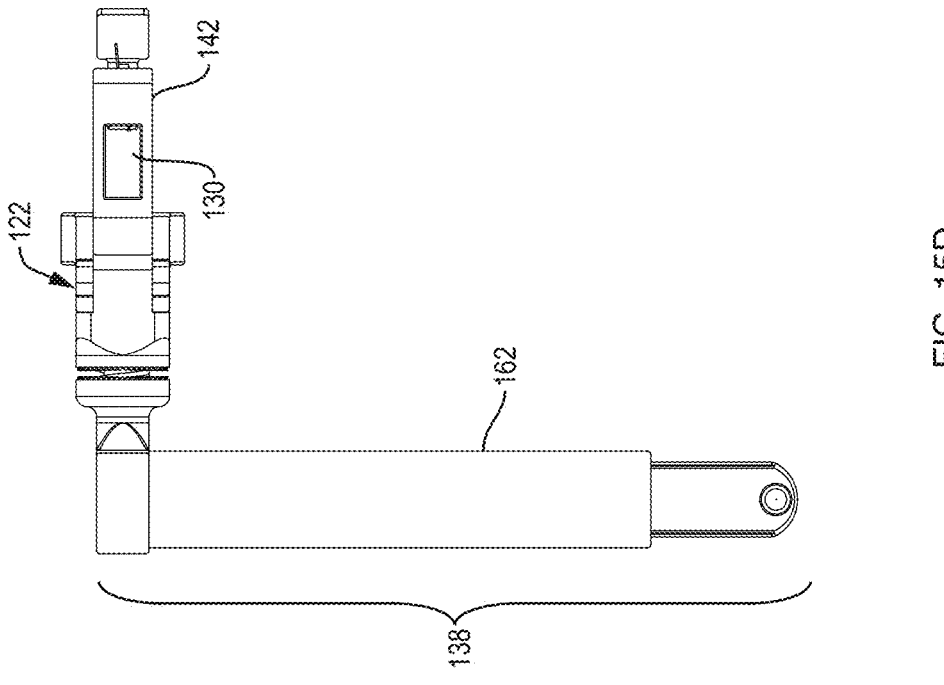
FIG. 15D is a front elevational view of the posterior distractor carriage assembly of FIG. 15A.
Figures 16A, 16B:
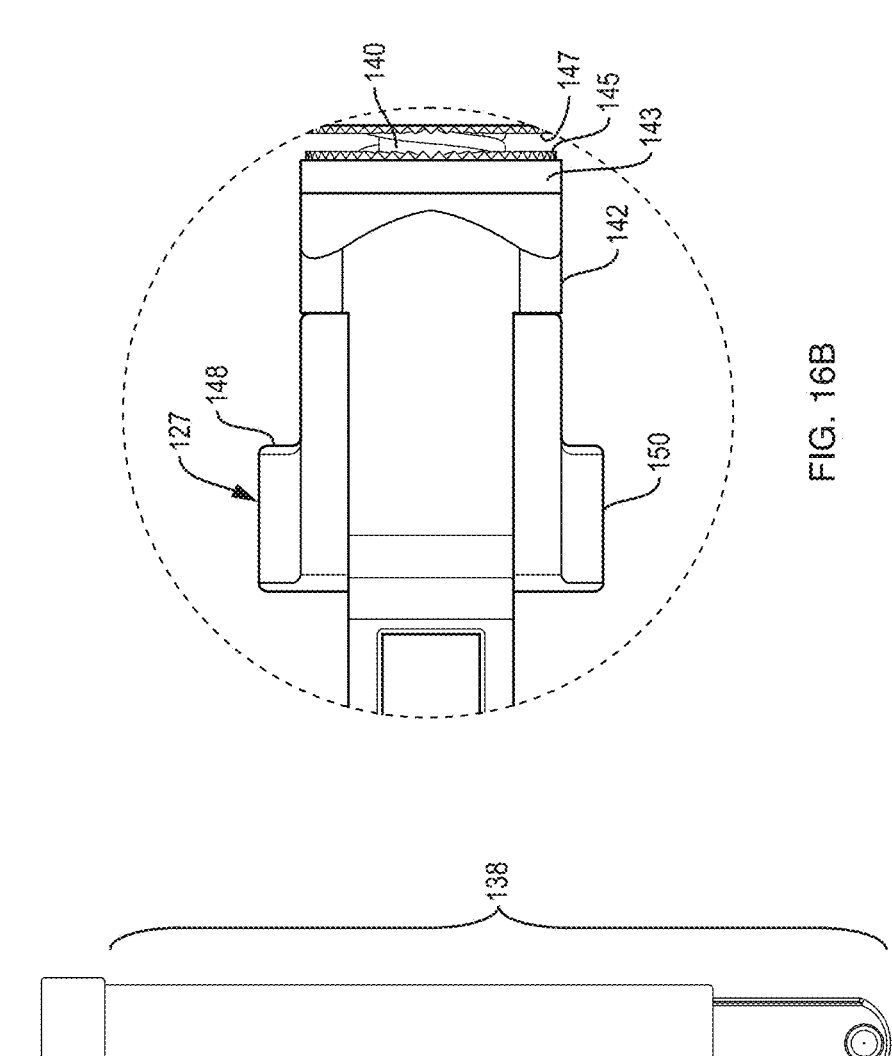
FIG. 16A is a rear elevational view of the posterior distractor carriage assembly of FIG. 15A.
FIG. 16B is a detailed view of a portion of FIG. 16A, as denoted in dashed lines.
Figure 16E:
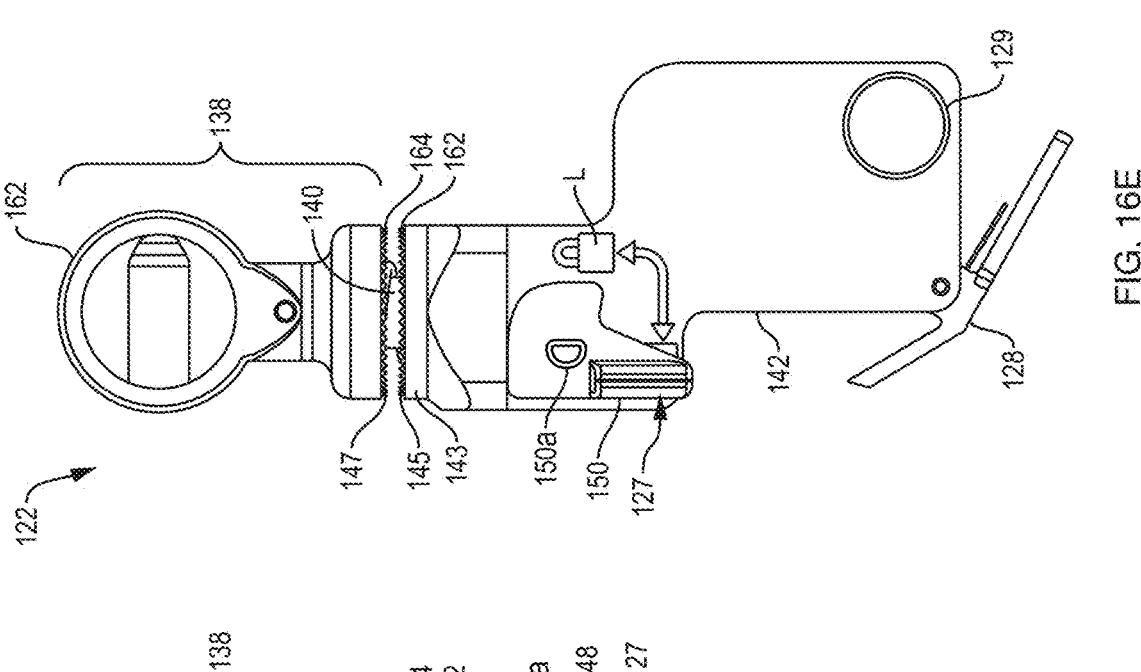
FIG. 16E is a bottom plan view of the posterior distractor carriage assembly of FIG. 15A, showing the spring lever assembly thereof in its unlocked position.
Figure 16D:
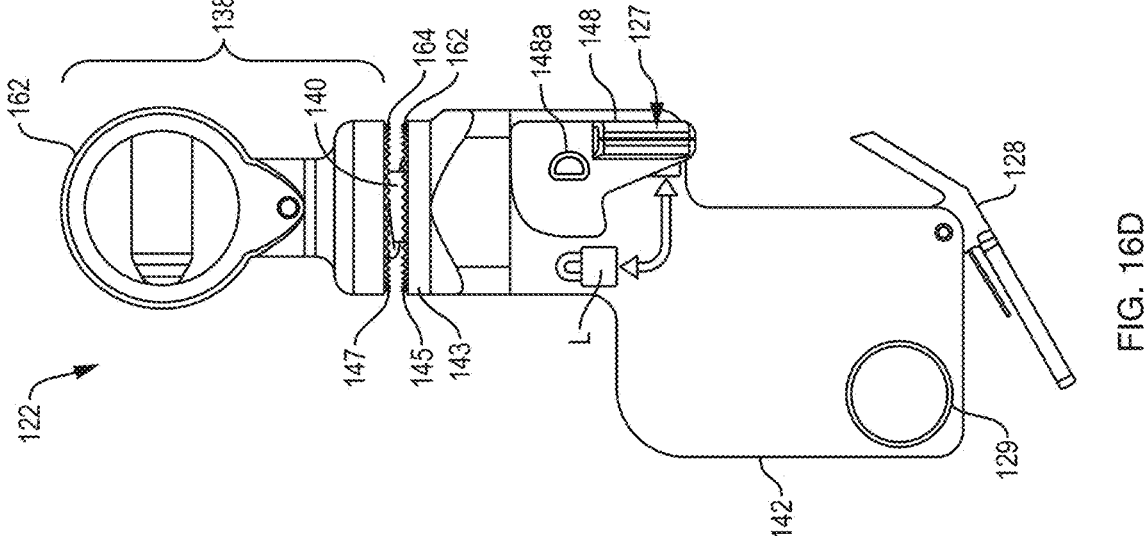
FIG. 16D is a top plan view of the posterior distractor carriage assembly of FIG. 15A, showing the spring lever assembly thereof in an unlocked position.
Figure 16C:
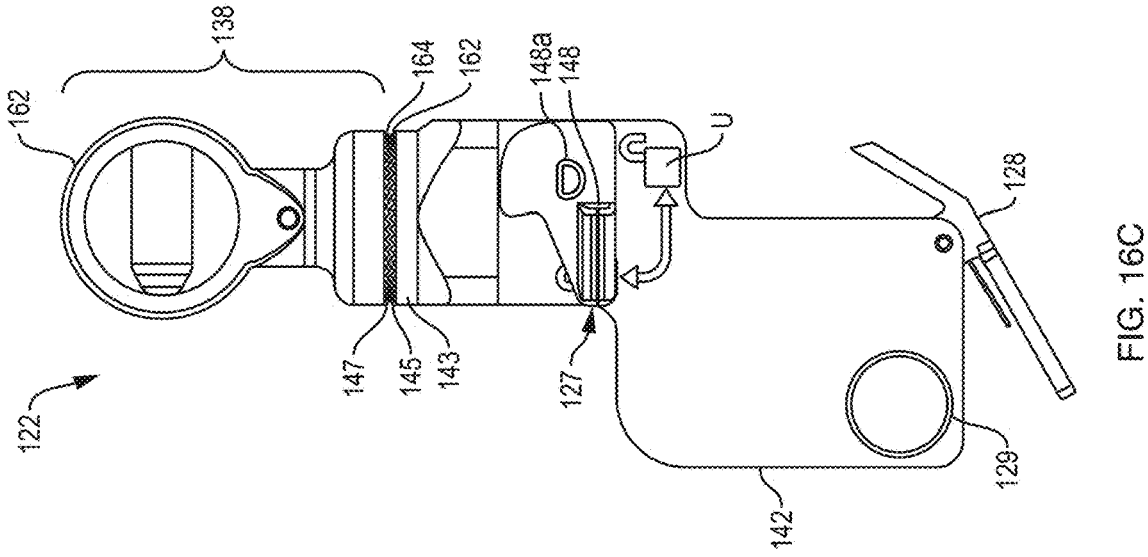
FIG. 16C is a top plan view of the posterior distractor carriage assembly of FIG. 15A, showing a spring lever assembly thereof in a locked position.

An internal fixation system 50 according to a second
embodiment of the present invention is shown in FIGS. 5
and 6 and is generally similar to the internal fixation system
10. However, in this embodiment, the internal fixation
system 50 includes at least two cannulated pedicle screws
52, 54 (instead of the cannulated posts of the first embodi-
ment) having respective distal ends 52a, 54a and proximal
ends 52b, 54b. The distal ends 52a, 54a are configured to be
inserted through respective pedicles P of the patient's spine
S, as illustrated in FIGS. 5 and 6. This internal fixation
system 50 is mounted directly to the surgical table T using
a table mount 16 (or other mounting means) that is also used
to position a lateral retractor 18 for prone spine access, as
illustrated in FIG. 4.

In this embodiment, a surgeon first inserts a guidewire
into the patient's vertebrae bone using fluoroscopic or
stereotactic navigation guidance. The surgeon then inserts
each cannulated screw 52, 54 with respective screw towers
62, 64 removably attached thereto over the guidewire.

The cannulated pedicle screw towers 62, 64 are then
operably connected to each other at their respective proxi-
mal ends using an actively- and passively-distracting frame
20 (see FIGS. 3 and 4).

Before or during discectomy work, active distraction can
be utilized to minimize the risk of endplate violation. During
a trialing step, when the disc space is being expanded to
select the proper size implant, the distracting frame 20 will
progressively expand in both height and in relative angula-
tion and maintain that distraction after the trial is removed.

Intraoperatively, the change in angulation and position of
the cannulated screws 52, 54 and screw towers 62, 64 can be
interpreted through stereotactic navigation to indicate to the
surgeon how significantly the patient's global and segmental
spinal alignment has changed.

After the prone lateral surgery is performed, the screw
towers 62, 64 are removed from the cannulated pedicle
screws 52, 54.

This embodiment inserts the final cannulated screws 52,
54 without needing to use an intermediate post. This saves
steps, simplifying the surgery and therefore facilitating a
decrease in surgery time and the risk of any adverse events.

An internal fixation system 100 according to a third
embodiment of the present invention is shown in FIGS.
7-13B. In this embodiment, the internal fixation system 100
includes a table-mounted L-column 102 and a table-
mounted A-arm 104 for the surgical table (not shown). A
B-arm 106 engages an end of the table-mounted A-arm 104
via a B-arm lateral connector 108 and an A-arm distal clamp
110 on an end of the A-arm 104. The B-arm 106 further
includes a B-arm posterior connector 112 that engages a posterior compressor/distractor 114. The internal fixation system 100 further includes a lateral lumbar interbody fusion (LLIF) retractor 116 having an LLIF retractor adaptor 118. FIGS. 7-13B show the internal fixation system 100 in use with a patient's spine S.

During a surgical technique according to this embodiment, a surgeon inserts cannulated implants (e.g., cannulated pedicle screws 52, 54 and respective screw towers 62, 64, as shown in FIG. 5) into the vertebrae of the patient's spine S, and connects these together with the compressor/distractor 114 (i.e., slides respective swivel tubes 162, 262 over the cannulated pedicle screws 52, 54 and respective screw towers 62, 64). Set caps or set screws are then used to lock the distractor to the cannulated implants. The cap/set screw is shown inside a tulip portion 55 of the pedicle screw 52, just above the rod analog that extends from the distractor tower/swivel tube 162 into the pedicle screw 52. The lateral retractor 116 is placed according to standard technique, connected to a surgical table using the table arm A 104. The compressor/distractor 114 is then connected to a connector (the distal clamp 110) on the table arm A and locked in place using the B arm 106 and B-arm lateral connector 108 (see FIGS. 7-8). Once the implant is placed, the caps are removed, and the distractor is removed. Rods are then inserted into the vertebrae, and set caps/set screws placed to complete the construct. If used, the screw towers 62, 64 are then removed. By connecting the lateral retractor 116 to screws internally fixated into bone (i.e., the patient's spine), the lateral retractor 116 becomes more stable, minimizing retractor motion and providing additional mechanical advantage. The use of the compressor/distractor 114 during the disc preparation, trialing, and implant insertion portions of a lateral interbody fusion procedure will decrease the risk of endplate violation and implant subsidence. By reducing subsidence, for aminal height is better maintained.

The posterior compressor/distractor 114 and its components according to various embodiments of the present invention are shown in FIGS. 14A-37C.

FIGS. 14A-14D show the posterior compressor/distractor 114 including a posterior distractor rack assembly 120, a posterior distractor carriage assembly 122 and a pinion assembly 124. These assembles operate together, whereby the posterior distractor rack assembly 120 and posterior distractor carriage assembly 122 move relative to one another. Each of these assemblies and their respective components are described below.

The posterior distractor rack assembly 120 includes a rack 126 having a plurality of ridges 126a on at least one surface thereof. The posterior distractor carriage assembly 122 includes a spring lever assembly 127 having indicia to show its locked and unlocked positions (L and U, respectively) a ratchet pawl 128, an aperture 129 and an opening 130 dimensioned to receive the rack 126 therethrough. In the embodiment illustrated, the opening 130 is rectangular. The pinion assembly 124 includes a knob 132 and a post 135 descending from the knob 132. A gear 134 circumferentially engages the post 135 and includes ridges 134a on its surface that interdigitate with the ridges 126a on the rack 126, as further discussed below. The aperture 129 of the posterior distractor carriage assembly 122 is dimensioned to receive the post 135 and gear 134 of the pinion assembly 124 therein (see FIG. 14A). The posterior compressor/distractor 114 further includes two swivel tube subassemblies 136, 138 that are configured to be moved and positioned with respect to each other. One swivel tube subassembly 138 is part of the posterior distractor carriage assembly 122, while the other swivel tube subassembly 136 is part of the posterior distractor rack assembly 120 (see FIGS. 14A-14D). As further discussed below, the swivel tube subassembly 138 includes the swivel tube 162, and the swivel tube subassembly 136 includes the swivel tube 262.

To assemble the posterior compressor/distractor 114 for surgery, the post 135 and surrounding gear 134 of the pinion assembly 124 is inserted into the aperture 129. The spring lever assembly 127 of the posterior distractor carriage assembly 122 is then deployed (i.e., moved to its unlocked position U), and the rack 126 of the posterior distractor rack assembly 120 is slid into the opening 130 of the posterior distractor carriage assembly 122 (see FIGS. 14B-14C). As the rack 126 is advanced through the opening 130 and the posterior distractor carriage assembly 122, the ridges 126a operably contact the ratchet pawl 128 and interdigitate with the ridges 134a on the gear 134 of the pinion assembly 124, which causes the knob 132 of the pinion assembly 124 to rotate smoothly and the distance between two swivel tube subassemblies 136, 138 to increase. Once a desired distance between the two swivel tube subassemblies 136, 138 is reached (i.e., based on the patient's measurements and other surgical parameters), the spring lever 127 is moved to its locked position L to secure the posterior compressor/distractor 114 in this position.

Reference is now made to FIGS. 15A-15E, which show components of the posterior distractor carriage assembly 122. The posterior distractor carriage assembly 122 includes the swivel tube subassembly 138, which has an arm, or rod, 140 extending therefrom, and a carriage hub 142. The arm 140 includes an aperture 140a formed in one end and an annular groove 141 formed in the opposite end, as further discussed below. Formed within the carriage hub 142 is the aperture 129 for receiving the post 135/gear 134 and the opening 130 for receiving the rack 126 (both of which are described above), as well as a cavity 144 configured to receive the arm 140 therein. The cavity 144 includes an opening 144a surrounded by an annular end 143 of the carriage hub 142. A first plurality of teeth 145 extend from the annular end 143. A compression spring 146 fits over the arm 140 of the swivel tube subassembly 138, and into the cavity 144 with the arm 140. A second plurality of teeth 147 is provided on an end of the swivel tube subassembly 138, proximate to and surrounding the arm 140, and is configured to removably engage (i.e., interdigitate with) the first plurality of teeth 145.

The spring lever assembly 127 of the posterior distractor carriage assembly 122 includes a top cam lever 148, a bottom cam lever 150, and a cam pin 152 configured to connect the top and bottom cam levers 148, 150 together on opposed surfaces of the carriage hub 142 through a cam aperture 154 formed therein. The cam pin 152 includes a first end 152a that is configured to engage a bore 148a formed in the top cam lever 148. The cam pin 152 also includes a second end 152b that is configured to engage a bore 150a formed in the bottom cam lever 150. The cam pin 152 is also configured to engage the groove 141 of the swivel tube subassembly arm 140 when inserted into the cavity 144. The ratchet pawl 128 engages a torsion spring 156 and a ratchet pin 158 positioned within a ratchet aperture 160 formed in the carriage hub 142 to enable movement of the ratchet pawl 128.

FIGS. 16A-16D further illustrate the posterior distractor carriage assembly 122. When the spring lever assembly 127 is positioned in its unlocked position U (FIGS. 16A, 16B, 16D and 16E, as well as FIGS. 14B, 15B and 15C), the swivel tube subassembly 138 is distanced from the carriage hub 142. When the spring lever assembly 127 is moved to its locked position L (i.e., by rotation of the top and bottom cam levers 148, 150), the cam pin 152 is rotated. Due to the cam pin 152's engagement with the groove 141 of the swivel tube subassembly arm 140, this rotation of the cam pin 152 causes the inward movement of the swivel tube subassembly arm 140 (i.e., drawing it further into the cavity 144). This in turn causes the second plurality of teeth 147 (on the swivel tube subassembly 138) to removably engage (i.e., interdigitate with) the first plurality of teeth 145, thereby locking the swivel tube subassembly 138 to the carriage hub 142 (see FIGS. 15B and 16C). This junction of the swivel tube subassembly 138 to the carriage hub 142 allows the angle between the swivel tube 162 to be adjustable to accommodate the angle of the pedicle screws. The junction also allows a single compressor/distractor 114 to be used for both right- and left-sided approaches (i.e., to the patient's disc space) as it allows 360° rotation.

Figure 17A:
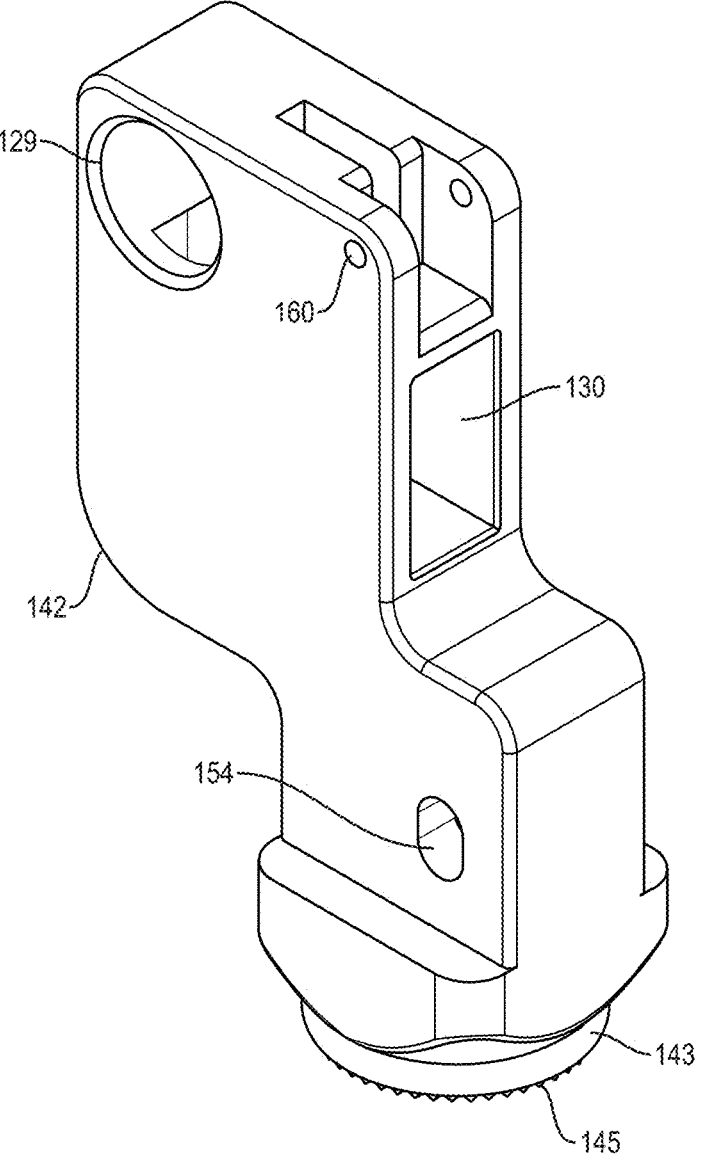
FIG. 17A is a top perspective view of a carriage hub of the posterior distractor carriage assembly of FIG. 15A.
Figure 17C:
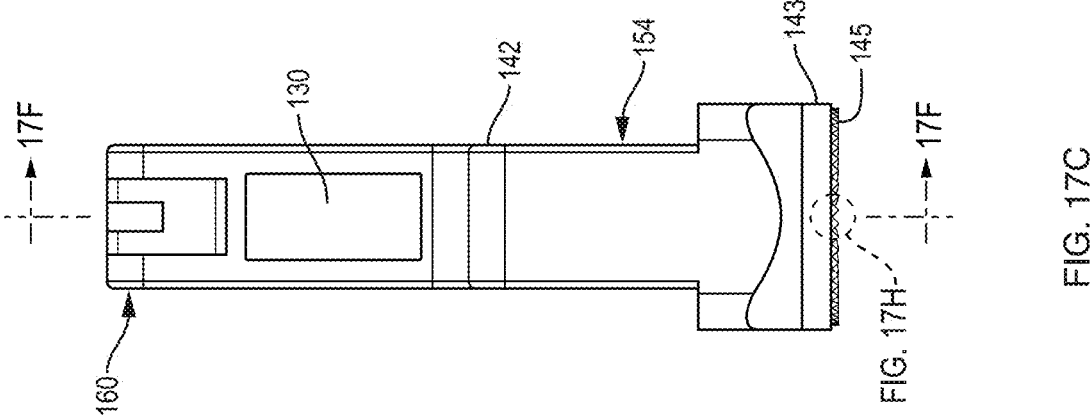
FIG. 17C is a side elevational view of the carriage hub of FIG. 17A.
Figure 17B:
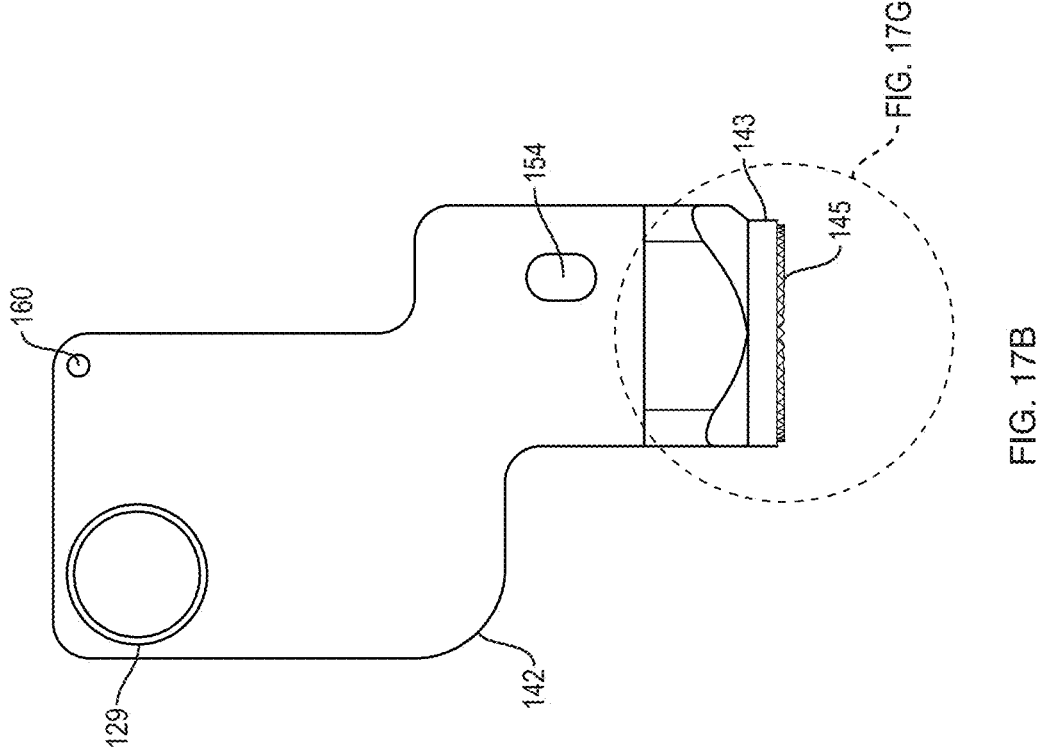
FIG. 17B is a front elevational view of the carriage hub of FIG. 17A.
Figure 17E:
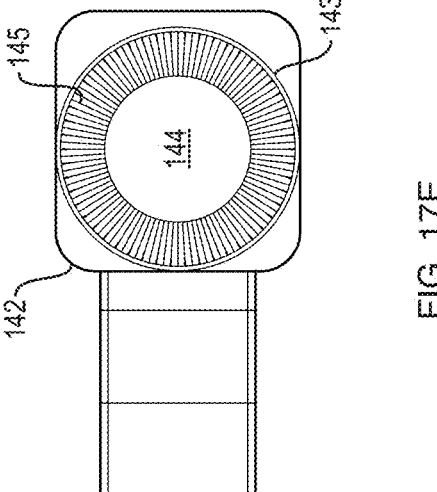
FIG. 17E is a bottom plan view of the carriage hub of FIG. 17A.
Figure 17D:
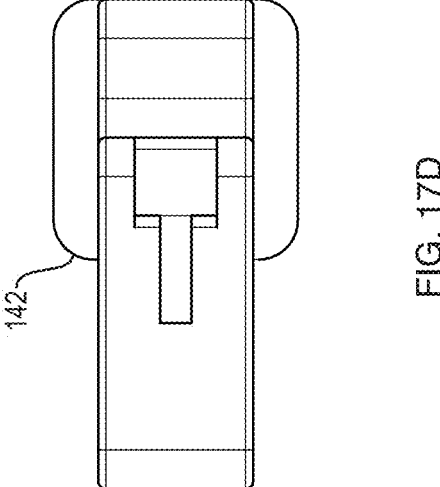
FIG. 17D is a top plan view of the carriage hub of FIG. 17A.
Figures 18A, 18B, 18C, 18D:
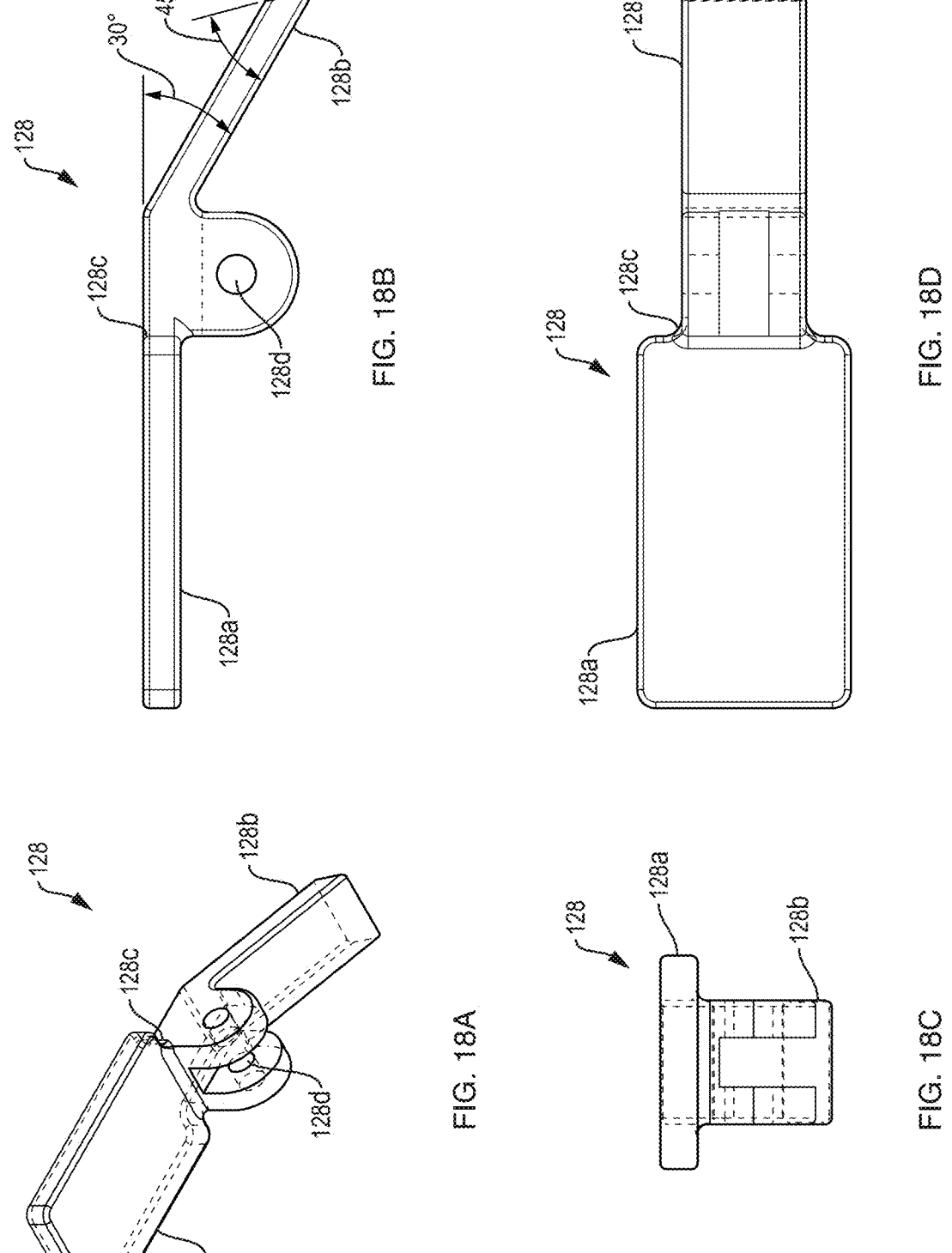
FIG. 18A is a bottom perspective view of a ratchet pawl of the posterior distractor carriage assembly of FIG. 15A.
FIG. 18B is a side elevational view of the ratchet pawl of FIG. 18A.
FIG. 18C is front plan view of the ratchet pawl of FIG. 18A.
FIG. 18D is top plan view of the carriage hub of FIG. 18A.
Figures 19A, 19B, 19C:
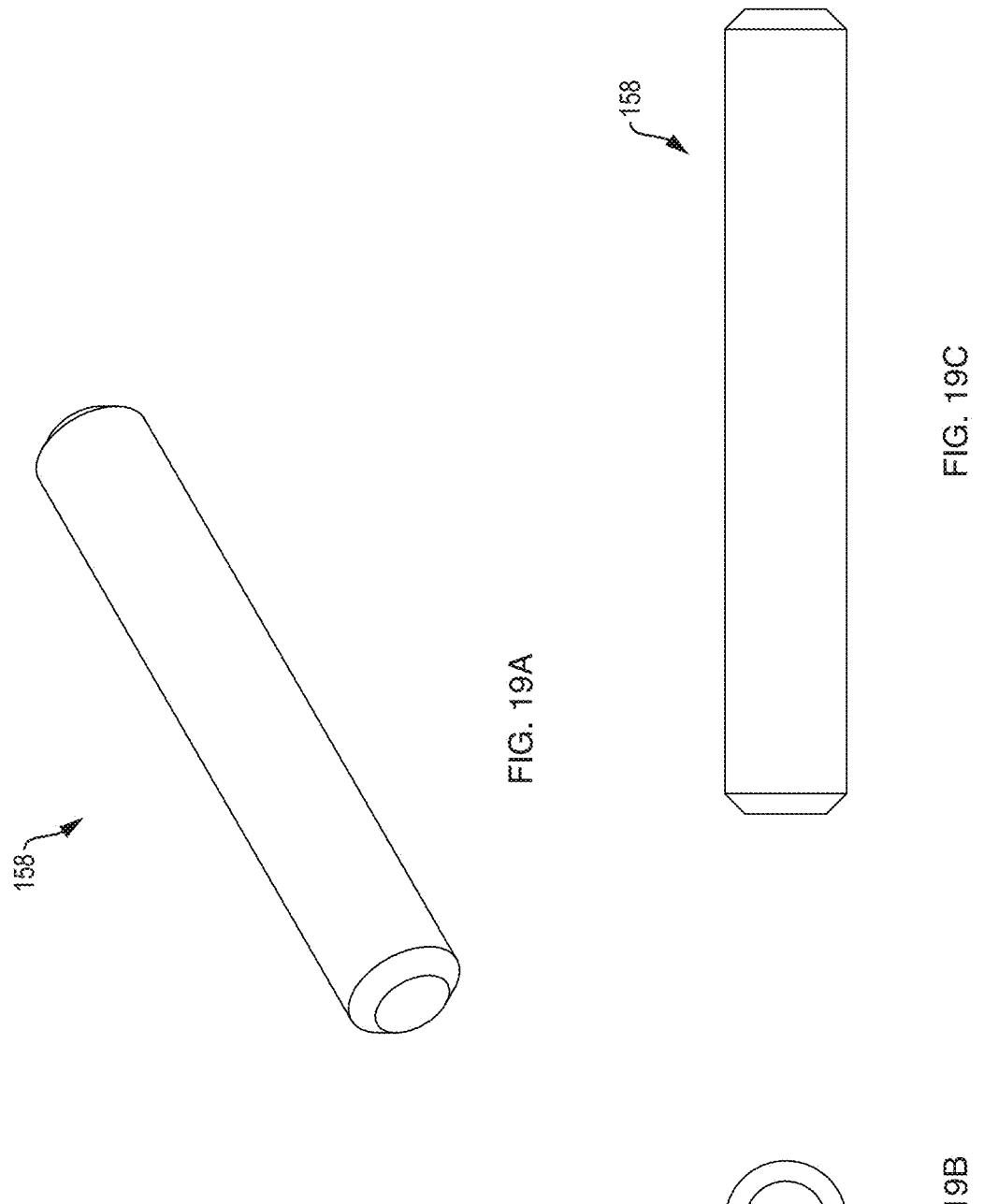
FIG. 19A is a top perspective view of a ratchet pin for use with the ratchet pawl of FIG. 18A.
FIG. 19B is front plan view of the ratchet pin of FIG. 19A.
FIG. 19C is a side elevational view of the ratchet pin of FIG. 19A.
Figure 21A:
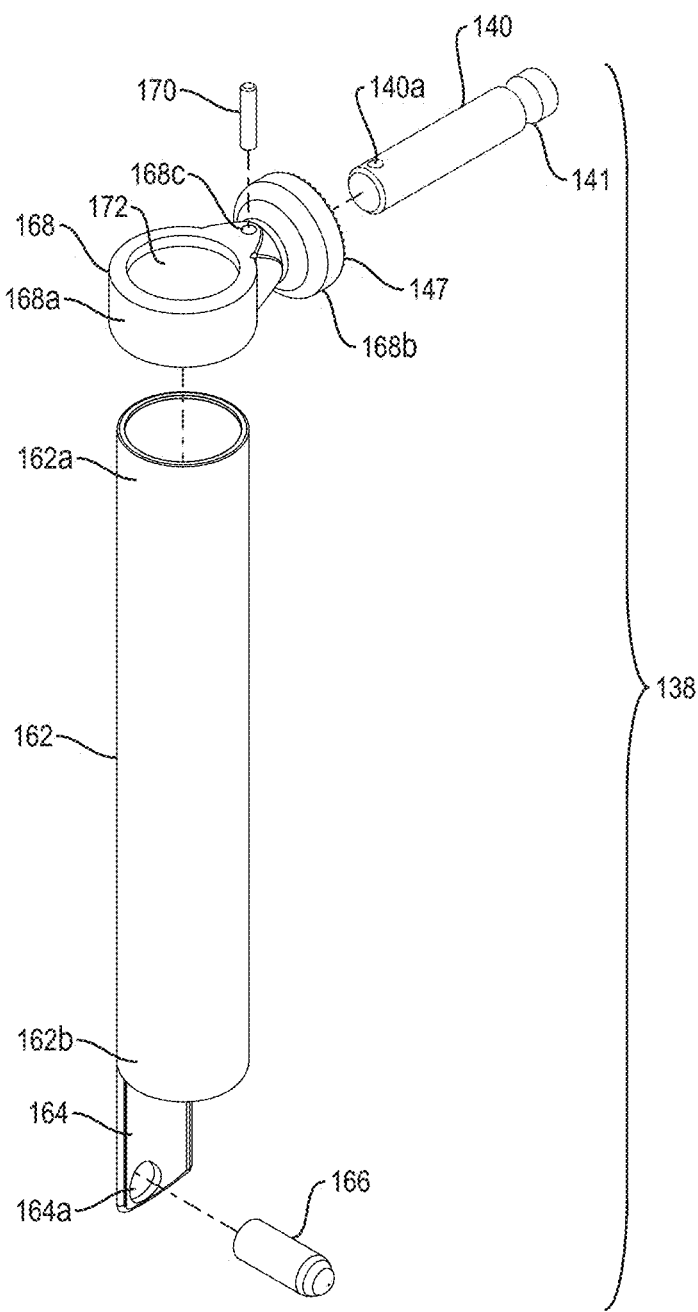
FIG. 21A is a top perspective exploded view of a first swivel tube subassembly of the posterior distractor carriage assembly of FIG. 15A.
Figure 21D:
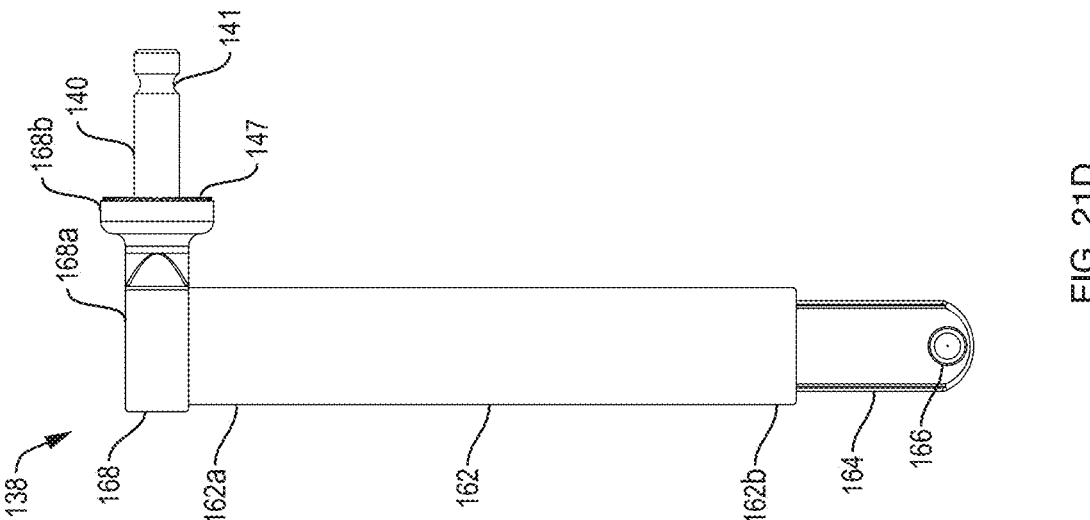
FIG. 21D is front elevational view of the swivel tube subassembly of FIG. 21A.
Figure 21C:
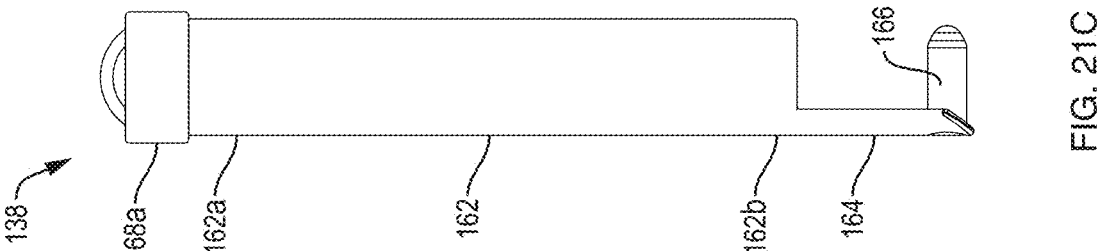
FIG. 21C is a side elevational view of the swivel tube subassembly of FIG. 21A.
Figure 21B:
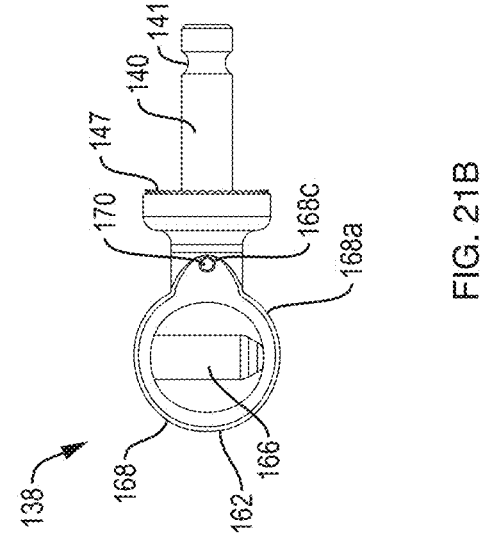
FIG. 21B is a top plan view of the swivel tube subassembly of FIG. 21A.
Figures 22A, 22B, 22C, 22D:
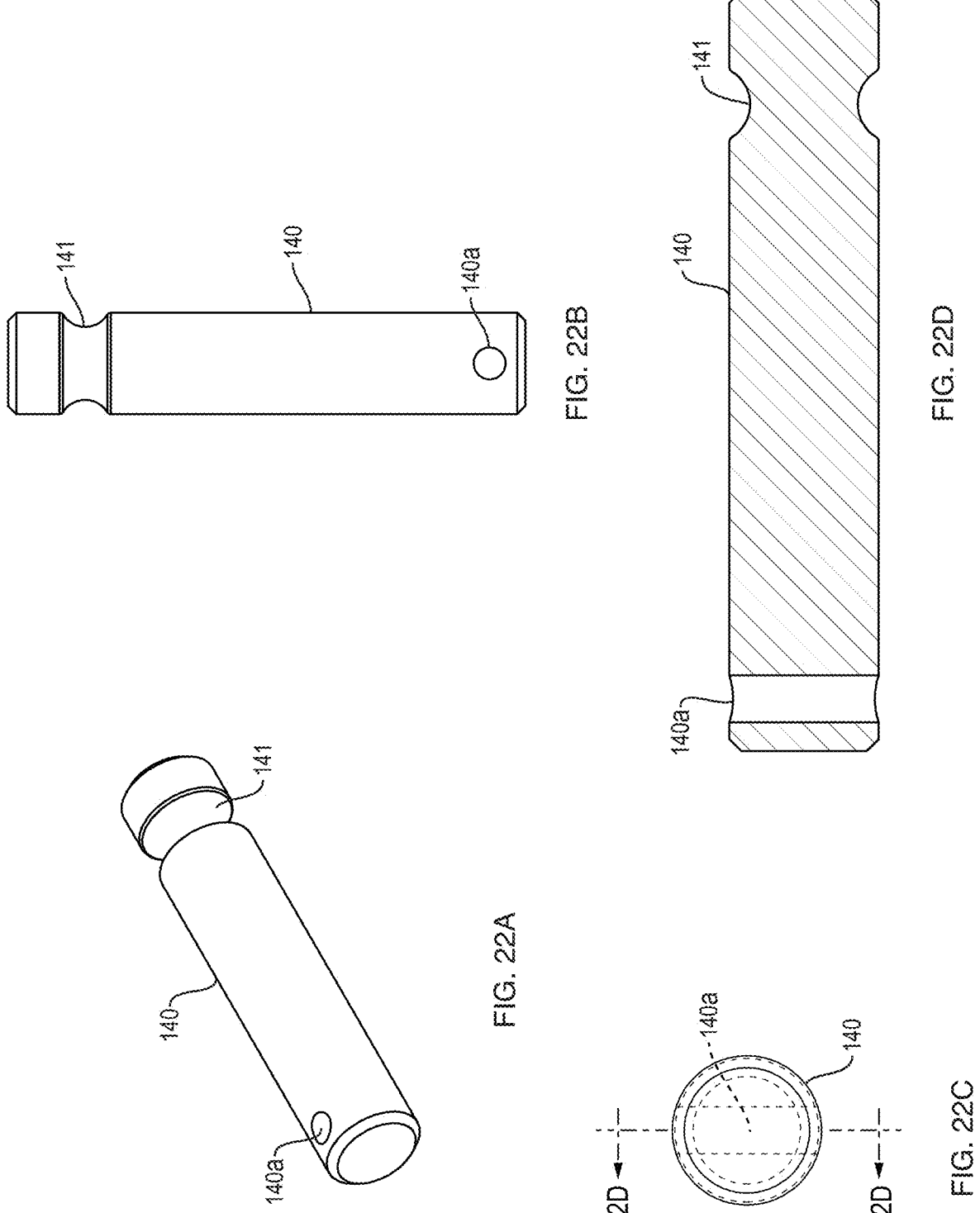
FIG. 22A is a top perspective view of an arm of the swivel tube subassembly of FIG. 21A.
FIG. 22B is a side elevational view of the arm of FIG. 22A.
FIG. 22C is a rear elevational view of the arm of FIG. 22A.
FIG. 22D is a cross-sectional view of the arm of FIGS. 22A and 22C, as taken along line 22D-22D in FIG. 22C.
Figures 24A, 24B, 24C:
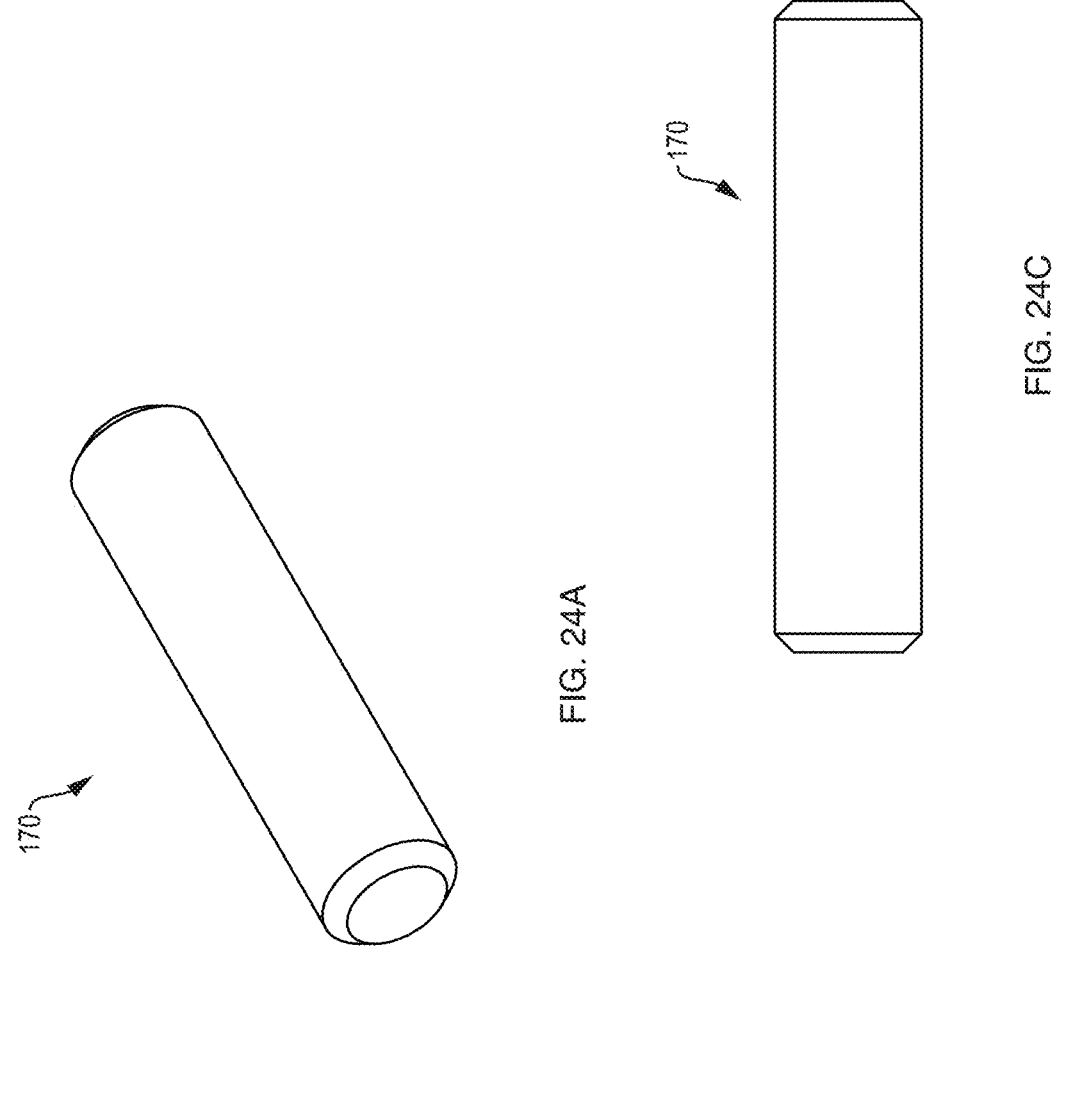
FIG. 24A is a top perspective view of a swivel tube pin of the swivel tube subassembly of FIG. 21A.
FIG. 24B is a front elevational view of the swivel tube pin of FIG. 24A.
FIG. 24C is a side elevational view of the swivel tube pin of FIG. 24A.
Figures 25A, 25B, 25C, 25D:
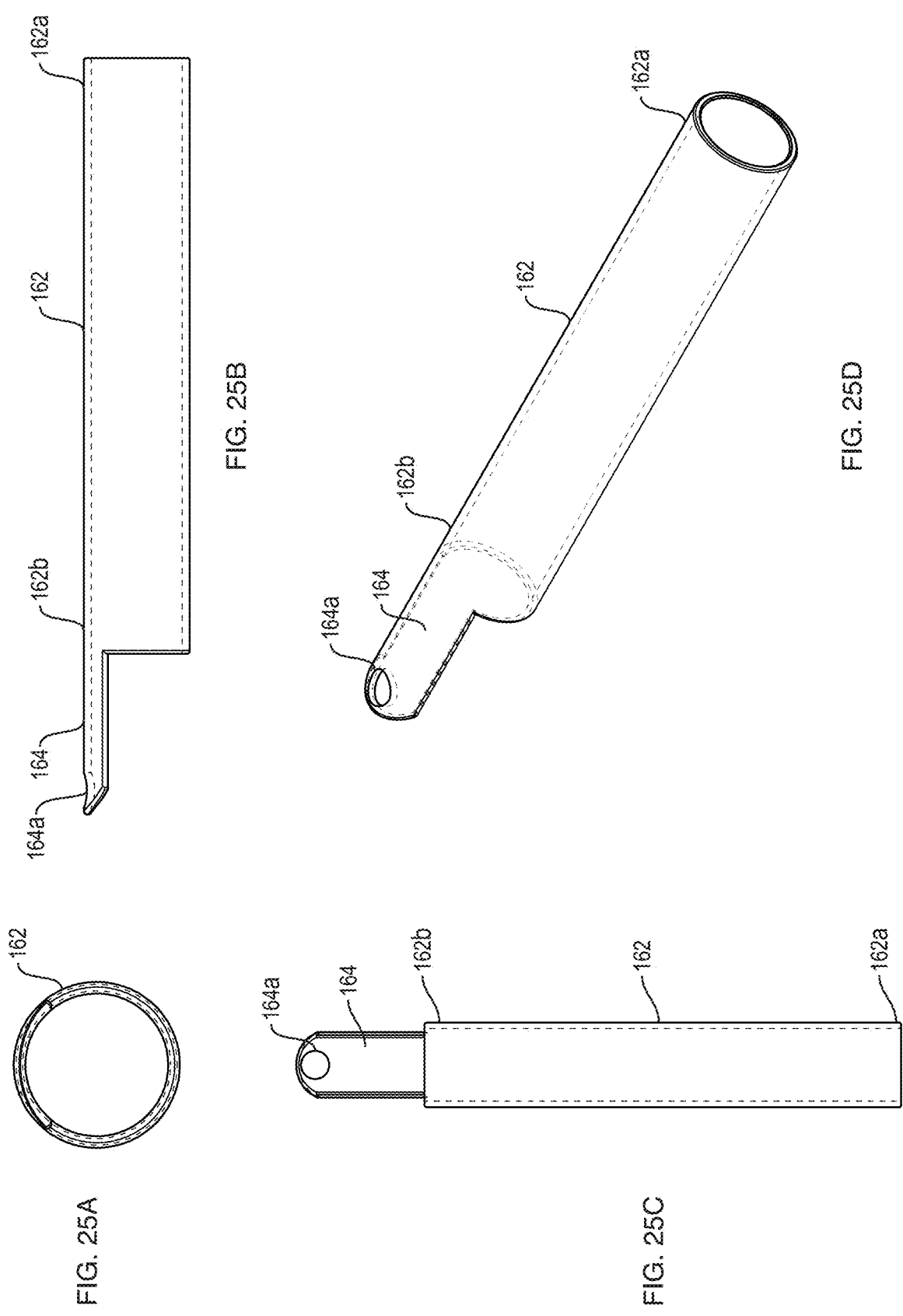
FIG. 25A is a bottom elevational view of a swivel tube of the swivel tube subassembly of FIG. 21A.
FIG. 25B is a side elevational view of the swivel tube of FIG. 25A.
FIG. 25C is a front elevational view of the swivel tube of FIG. 25A.
FIG. 25D is a top perspective view of the swivel tube of FIG. 25A.

FIGS. 17A-17H further illustrate the carriage hub 142, including the aperture 129, opening 130, cam pin aperture 154 and rachet aperture 160 thereof. FIG. 17F shows the cavity 144, which is configured to receive the swivel tube subassembly arm 140 therein. FIG. 17G shows an embodiment wherein the angle formed between the annular end 143 and an adjacent portion of the carriage hub 142 is 141°. Other angles are possible in other embodiments. FIG. 17H shows an embodiment wherein the angle formed between adjacent ones of the first plurality of teeth 145 is 90°. Other angles are possible in other embodiments.

FIGS. 18A-18D further illustrate the ratchet pawl 128 of the posterior distractor carriage assembly 122. The ratchet pawl 128 includes first and second members 128a, 128b rotatably connected by a hinge 128c (or other bending means). A bore 128d extends through a portion of the second member 128b, and is dimensioned to receive the ratchet pin 158 therethrough. The ratchet pin 158 is further illustrated in FIGS. 19A-19C.

The torsion spring 156 is further illustrated in FIGS. 20A-20C. The torsion spring 156 includes arms 156a, 156b that engage the first and second members 128a, 128b of the ratchet pawl 128, respectively, and a coil spring 156c between and connecting the arms 156a, 156b. The coil spring 156c defines an opening 156d dimensioned to receive the ratchet pin 158 therethrough.

The swivel tube subassembly 138 is further illustrated in FIGS. 21A-21D. The swivel tube subassembly 138 is shown as a right-hand version in these figures, but it should be understood that a left-hand version of the swivel tube subassembly 138 would be the mirror image of those shown in these figures. The swivel tube subassembly 138 includes a swivel tube 162 having first and second ends 162a, 162b, and being dimensioned to receive the cannulated pedicle screw 52 and screw tower 62 therein, as discussed above and shown in FIG. 13. The second end 162b includes an extension member 164 with an aperture 164a dimensioned to receive an end of a swivel tube tulip rod 166 therein. The swivel tube subassembly 138 includes a swivel tube hub 168 having a first portion 168a that is configured to engage the first end 162a of the swivel tube, and a second portion 168b with the second plurality of teeth 147 formed thereon and configured to receive the end of the swivel tube subassembly arm 140 having the aperture 140a therein. The swivel tube subassembly arm 140 is further illustrated in FIGS. 22A-22D.

The swivel tube hub 168 is further illustrated in FIGS. 23A-23H. The first portion 168a is generally annular and defines a circular opening 172 therethrough. The second portion 168b is also generally annular, and defines a cavity 174 therein that is dimensioned to receive the end of the swivel tube subassembly arm 140 having the aperture 140a therein. The swivel tube pin 170 is further illustrated in FIGS. 24A-24C. The swivel tube 138 is further illustrated in FIGS. 25A-25D.

The swivel tube tulip rod 166 is further illustrated in FIGS. 26A-26C. The swivel tube tulip rod 166 includes a longitudinal axis A-A, and a rounded or domed end 166a. The swivel tube tulip rod 166 is configured to insertably engage slots in the screw tower 62 when engaging same. The rounded end 166a has the domed shaped to exclude sharp edges or corners that could catch, snag and/or tear/damage the patient's adjacent soft tissue. In the embodiment shown, the domed end 166a and longitudinal axis A-A form a first angle between them of 30°. Other angles are possible in other embodiments.

The compression spring 146 is further illustrated in FIGS. 27A-27C. The cam pin 152 is further illustrated in FIGS. 28A-28D. Ends 152a, 152b of the cam pin 152 are configured to have a D-shaped cross section and insertably engage the respective bores 148a, 150a of the top and bottom cam levers 148, 150 of the spring lever assembly 127.

Figure 29A:
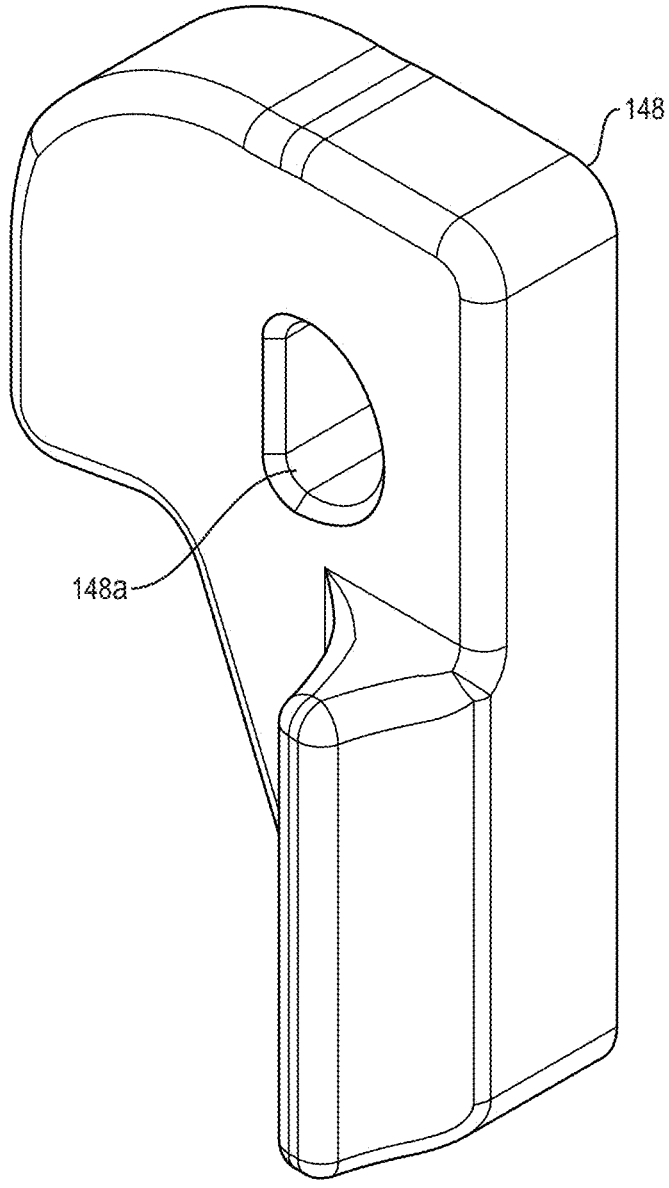
FIG. 29A is a top perspective view of a top cam lever of the posterior distractor carriage assembly of FIG. 15A.
Figure 29C:
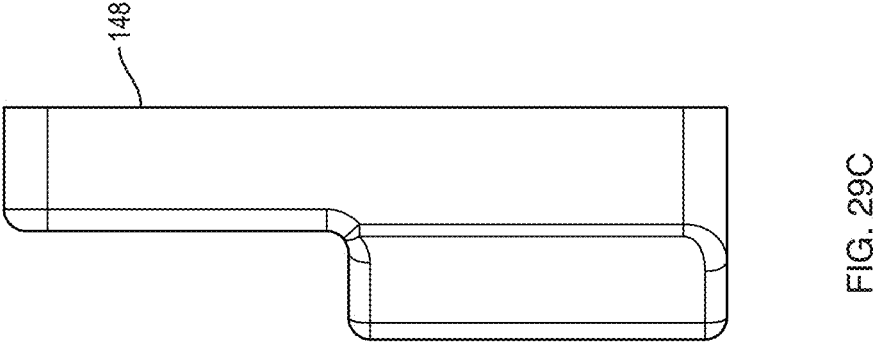
FIG. 29C is a side elevational view of the top cam lever of FIG. 29A.
Figure 29B:
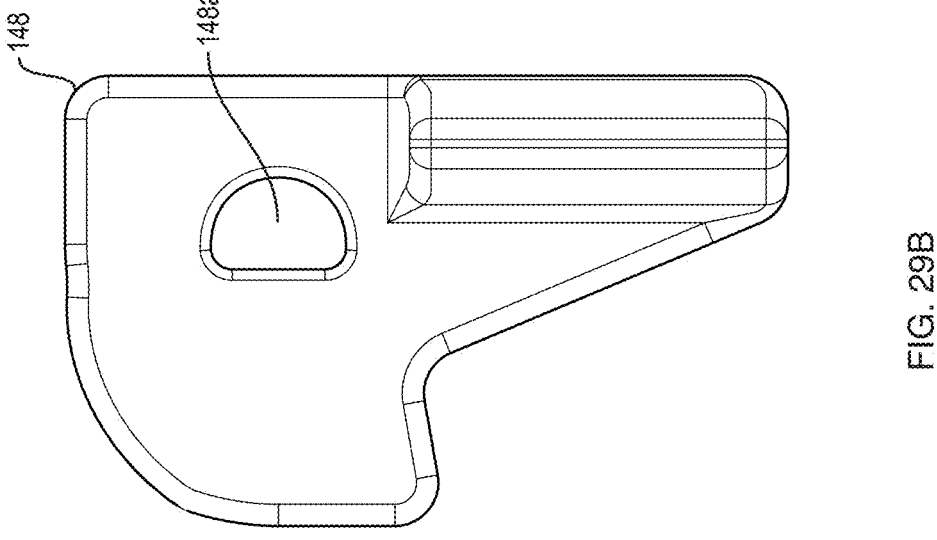
FIG. 29B is a front elevational view of the top cam lever of FIG. 29A.
Figure 29E:
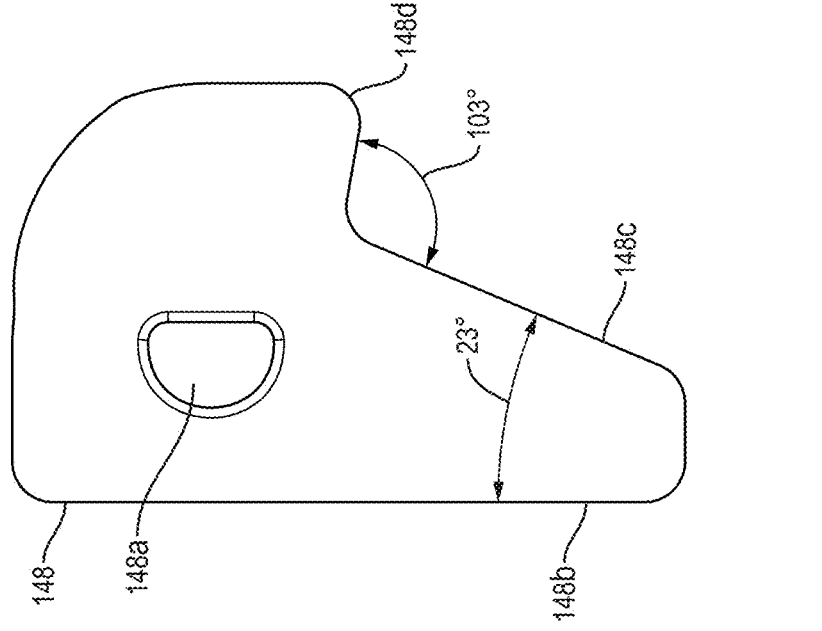
FIG. 29E is a rear elevational view of the top cam lever of FIG. 29A.
Figure 29D:
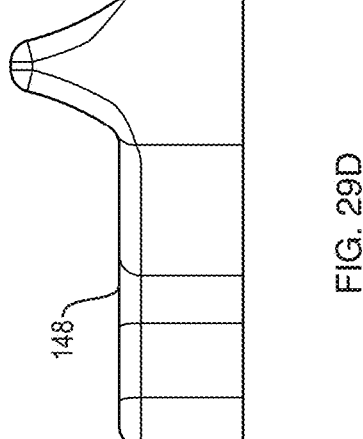
FIG. 29D is a top plan view of the top cam lever of FIG. 29A.

The top cam lever 148 is further illustrated in FIGS. 29A-29E, and includes a D-shaped bore 148a for receiving the end 152a of the cam pin 152 therein. As illustrated in FIG. 29E, the top cam lever 148 also includes a first edge 148b, a second edge 148c spaced from the first edge 148b, and a third edge 148d spaced from the second edge 148c. In the embodiment shown, the first and second edges 148b, 148c form a first angle between them of 23°, and the second and third edges 148c, 148d form a second angle between them of 103°. Other angles are possible in other embodiments.

Figure 30A:
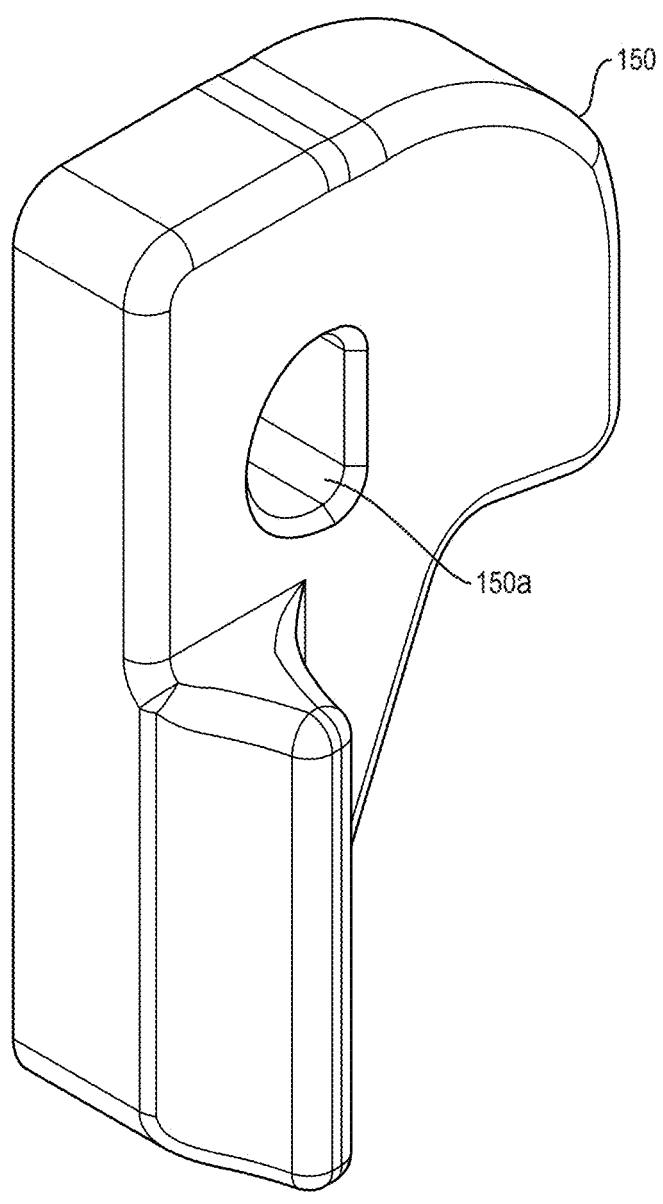
FIG. 30A is a bottom perspective view of a top cam lever of the posterior distractor carriage assembly of FIG. 15A.
Figure 30C:
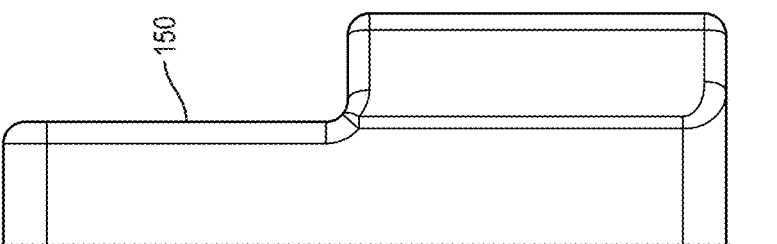
FIG. 30C is a side elevational view of the bottom lever of FIG. 30A.
Figure 30B:
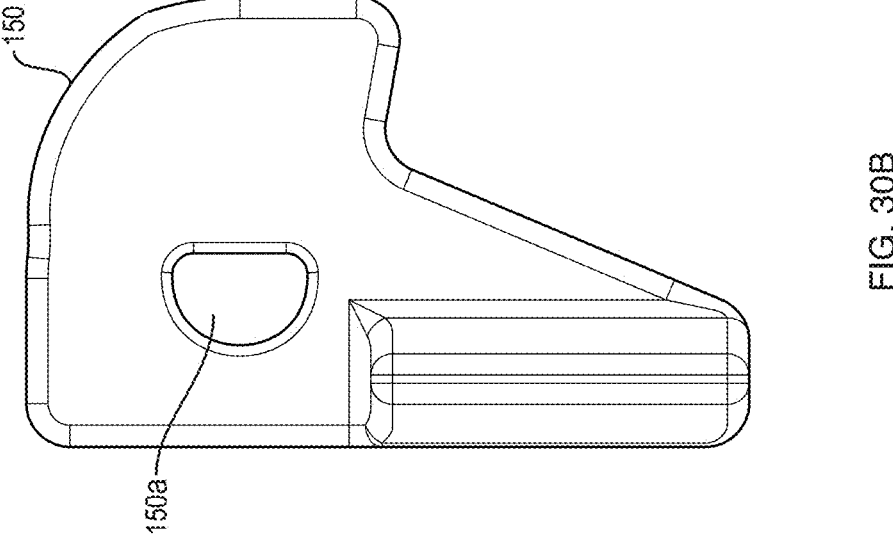
FIG. 30B is a front elevational view of the bottom cam lever of FIG. 30A.
Figure 30E:
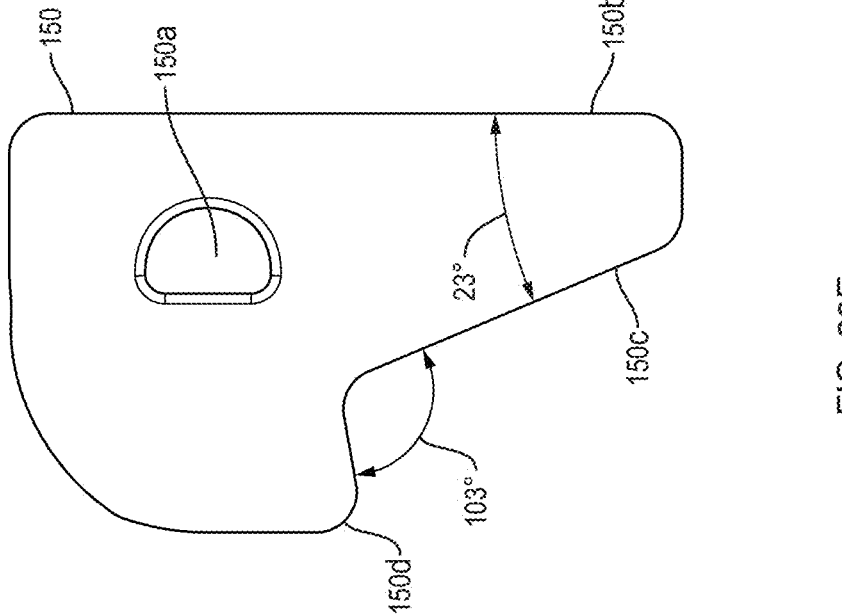
FIG. 30E is a rear elevational view of the bottom cam lever of FIG. 30A.
Figure 30D:
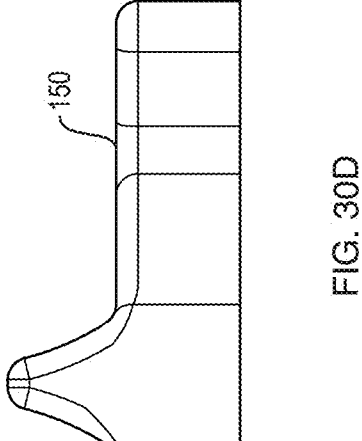
FIG. 30D is a top plan view of the bottom cam lever of FIG. 30A.
Figure 31A:
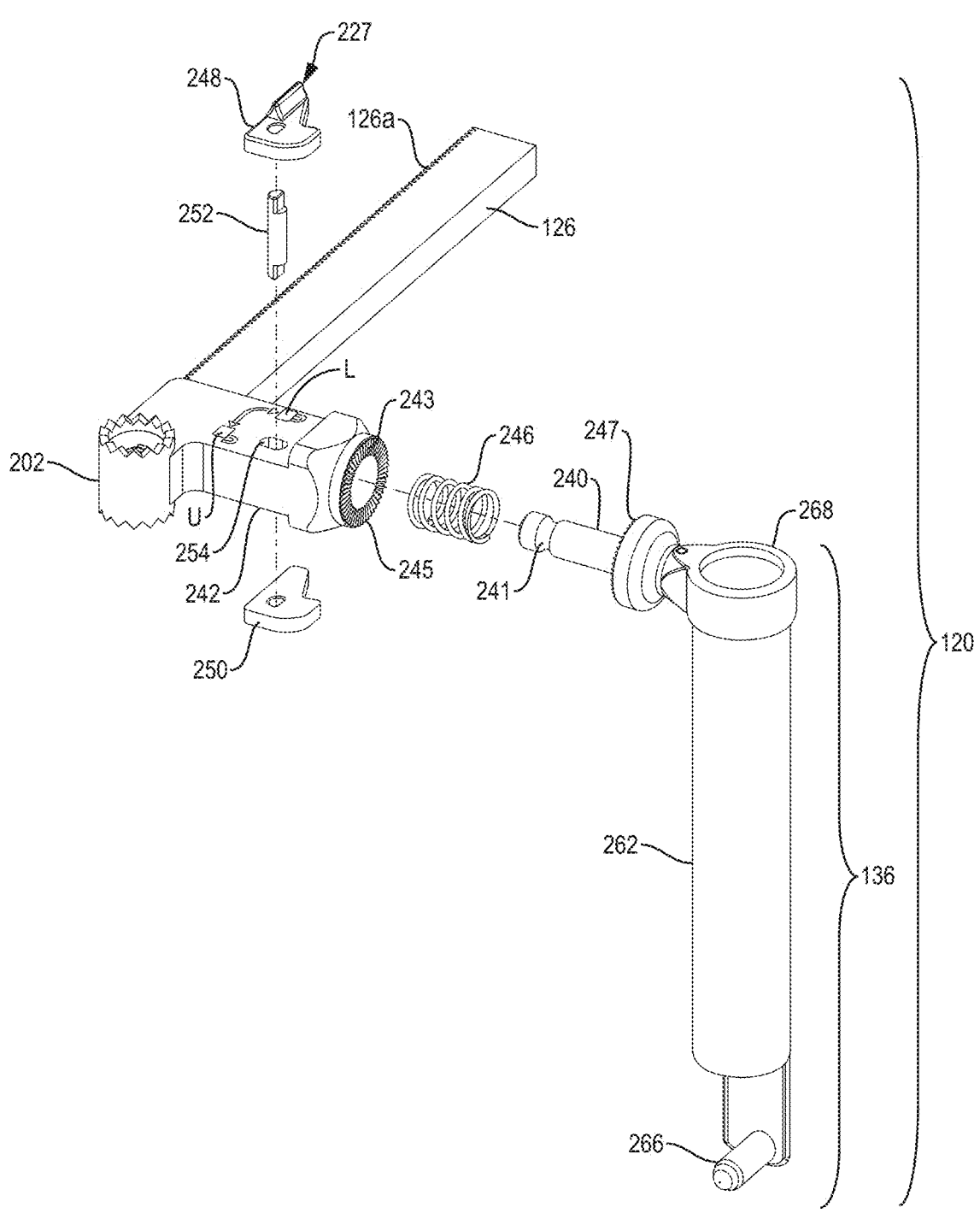
FIG. 31A is a top perspective exploded view of a posterior distractor rack assembly of the posterior compressor/distractor of FIG. 14A.
Figures 31B, 31C:
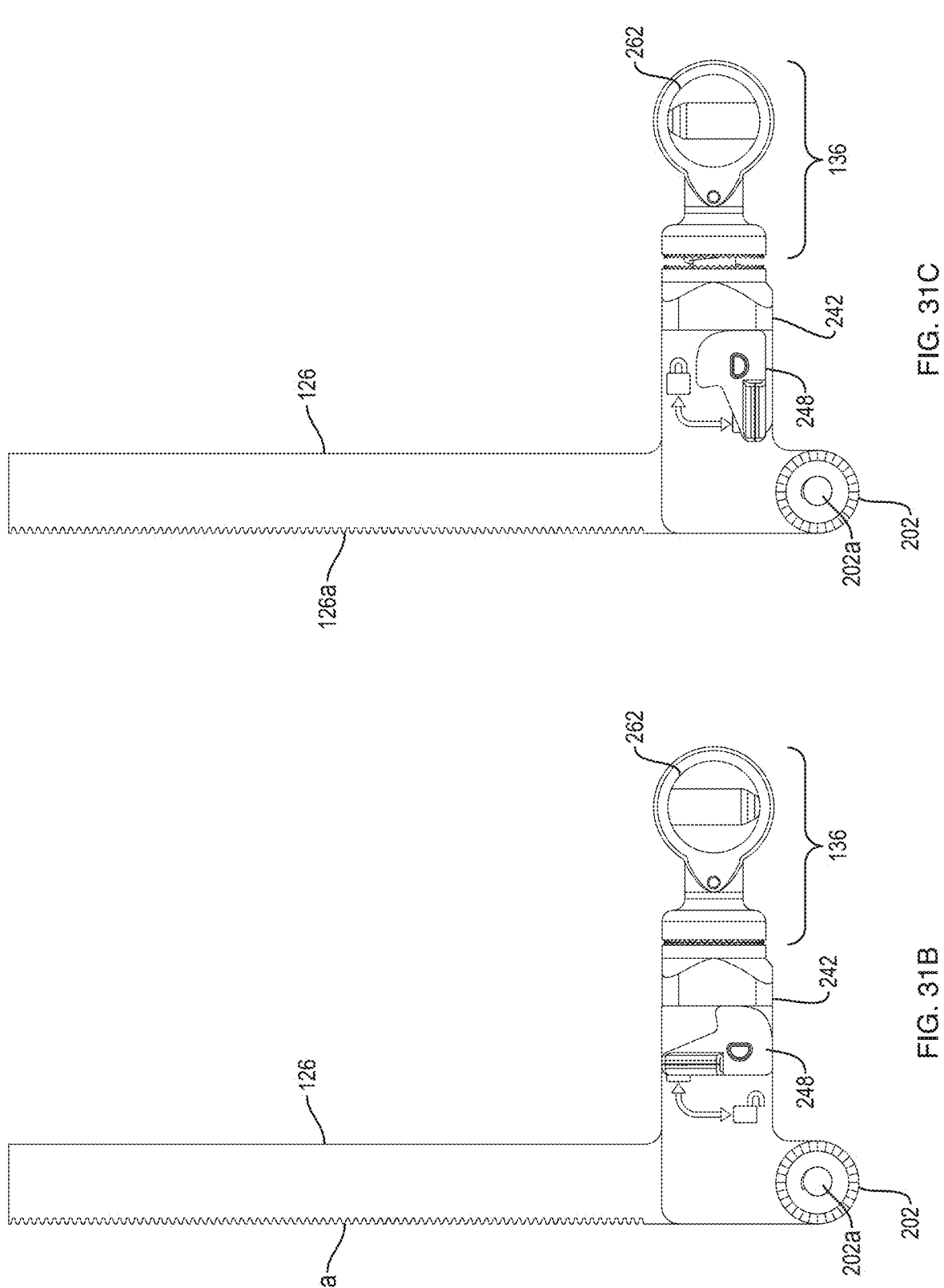
FIG. 31B is a top plan view of the posterior distractor rack assembly of FIG. 31A showing a spring lever assembly thereof in an unlocked position.
FIG. 31C is a top plan view of the posterior distractor rack assembly of FIG. 31A showing a spring lever assembly thereof in a locked position.
Figure 31D:
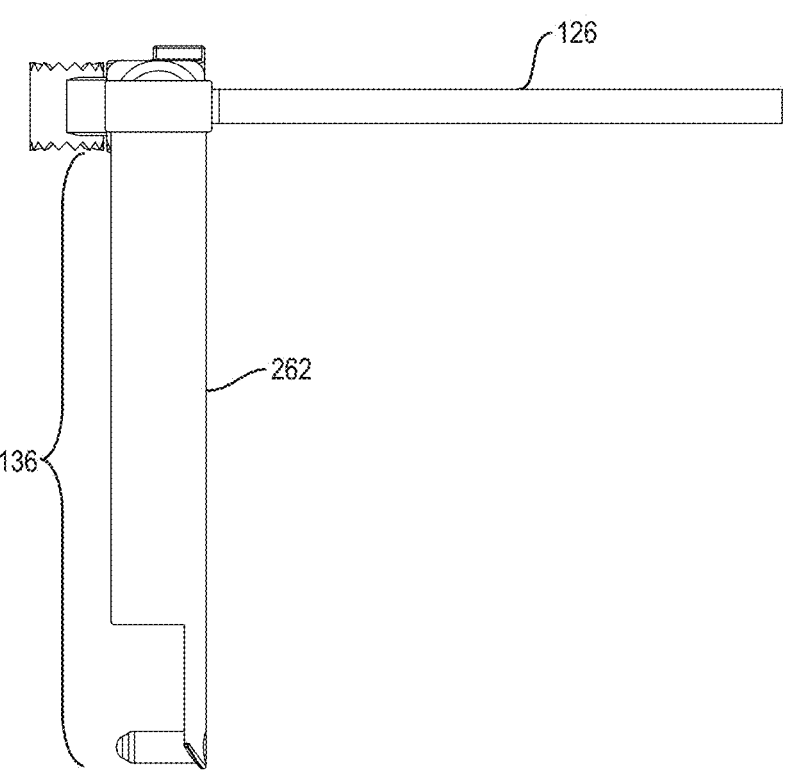
FIG. 31D is a side elevational view of the posterior distractor rack assembly of FIG. 31A.
Figure 31E:
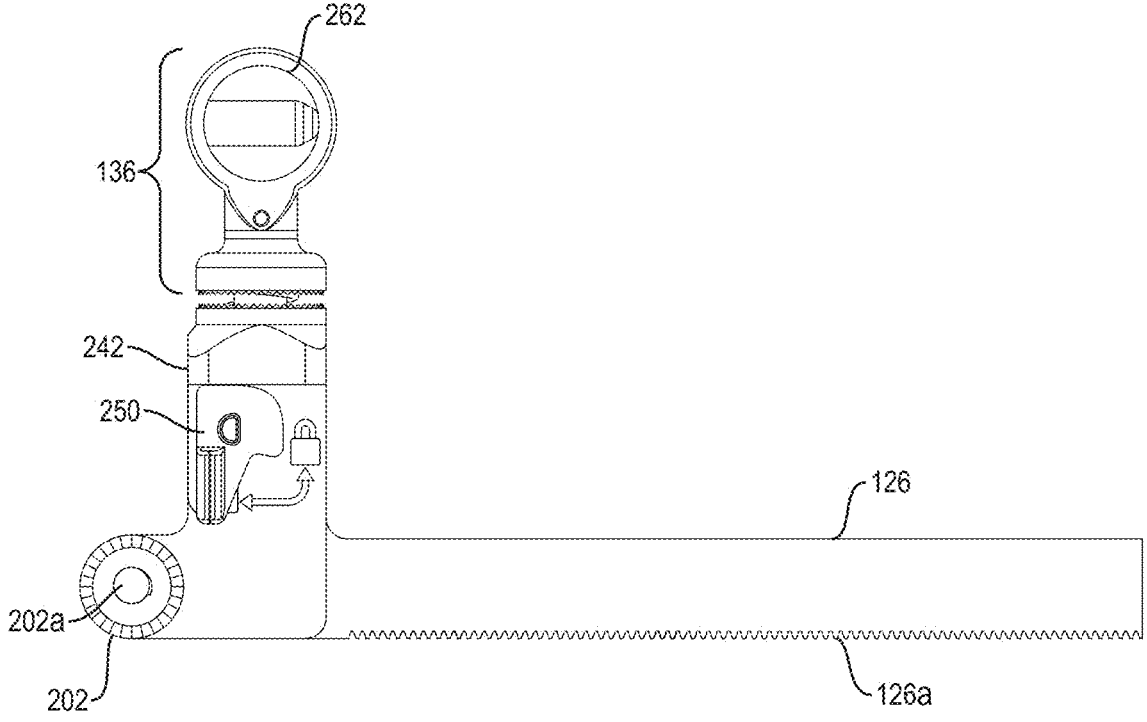
FIG. 31E is a bottom (looking upwards) plan view of the posterior distractor rack assembly of FIG. 31A showing a spring lever assembly thereof in a locked position.

The bottom cam lever 150 is further illustrated in FIGS. 30A-30E, and is formed as a mirror image of the top cam lever 148. The bottom cam lever 150 includes a D-shaped bore 150a for receiving the end 152b of the cam pin 152 therein. As illustrated in FIG. 30E, the bottom cam lever 150 also includes a first edge 150b, a second edge 150c spaced from the first edge 150b, and a third edge 150d spaced from the second edge 150c. In the embodiment shown, the first and second edges 150b, 150c form a first angle between them of 23°, and the second and third edges 150c, 150d form a second angle between them of 103°. Other angles are possible in other embodiments.

FIGS. 31A-31D further illustrate the posterior distractor rack assembly 120 and its components. Where applicable, components of the posterior distractor rack assembly 120 have been assigned reference numbers in the 200s to correspond with the same/corresponding components of the posterior distractor carriage assembly 122 with reference numbers in the 100s, and have the same or similar structure and function.

The posterior distractor rack assembly 120 includes the swivel tube subassembly 136. While the swivel tube subassembly 136 is shown as a left-hand version in these figures, but it should be understood that a right-hand version of the swivel tube subassembly 136 would be the mirror image of those shown in these figures. The swivel tube subassembly 136 includes a swivel tube 262, a swivel tube tulip rod 266, a swivel tube hub 268, an arm, or rod, 240 extending therefrom, and a rack hub 242. The arm 240 includes an annular groove 241 formed in an end thereof, as further discussed below. Formed within the rack hub 242 is a cavity 244 configured to receive the arm 240 therein. The cavity 244 includes an opening 244a surrounded by an annular end 243 of the rack hub 242. A third plurality of teeth 245 extend from the annular end 243. A compression spring 246 fits over the arm 240 of the swivel tube subassembly 136, and into the cavity 244 with the arm 240. A fourth plurality of teeth 247 is provided on an end of the swivel tube subassembly 136, proximate to and surrounding the arm 240, and is configured to removably engage (i.e., interdigitate with) the third plurality of teeth 245.

The posterior distractor rack assembly 120 further includes a spring lever assembly 227 having indicia to show its locked and unlocked positions (L and U, respectively). The spring lever assembly 227 includes a top cam lever 248, a bottom cam lever 250, and a cam pin 252 configured to connect the top and bottom cam levers 248, 250 together on opposed surfaces of the rack hub 242 through a cam aperture 254 formed therein. The cam pin 252 has the same structure as the cam pin 152 of the posterior distractor carriage assembly 122 described above, including first and second ends configured to engage bores formed in the top and bottom cam levers 248, 250. The cam pin 252 is also configured to engage the groove 241 of the swivel tube subassembly arm 240 when inserted into the cavity 244.

The posterior distractor rack assembly 120 operates similar to the operation of the posterior distractor carriage assembly 122 discussed above. When the spring lever assembly 227 is positioned in its unlocked position U (see FIG. 31C), the swivel tube subassembly 136 is distanced from the rack hub 242. When the spring lever assembly 227 is moved to its locked position L (i.e., by rotation of the top and bottom cam levers 248, 250), the cam pin 252 is rotated. Due to the cam pin 252's engagement with the groove 241 of the swivel tube subassembly arm 240, this rotation of the cam pin 252 causes the inward movement of the swivel tube subassembly arm 240 (i.e., drawing it further into the cavity 124). This in turn causes the second plurality of teeth 247 (on the swivel tube subassembly 136) to removably engage (i.e., interdigitate with) the first plurality of teeth 245, thereby locking the swivel tube subassembly 136 to the rack hub 242 (see FIG. 31B). This junction of the swivel tube subassembly 136 to the rack hub 242 allows the angle between the swivel tube 262 to be adjustable to accommodate the angle of the pedicle screws. The junction also allows a single compressor/distractor 114 to be used for both right- and left-sided approaches (i.e., to the patient's disc space) as it allows 360° rotation.

Figure 32A:
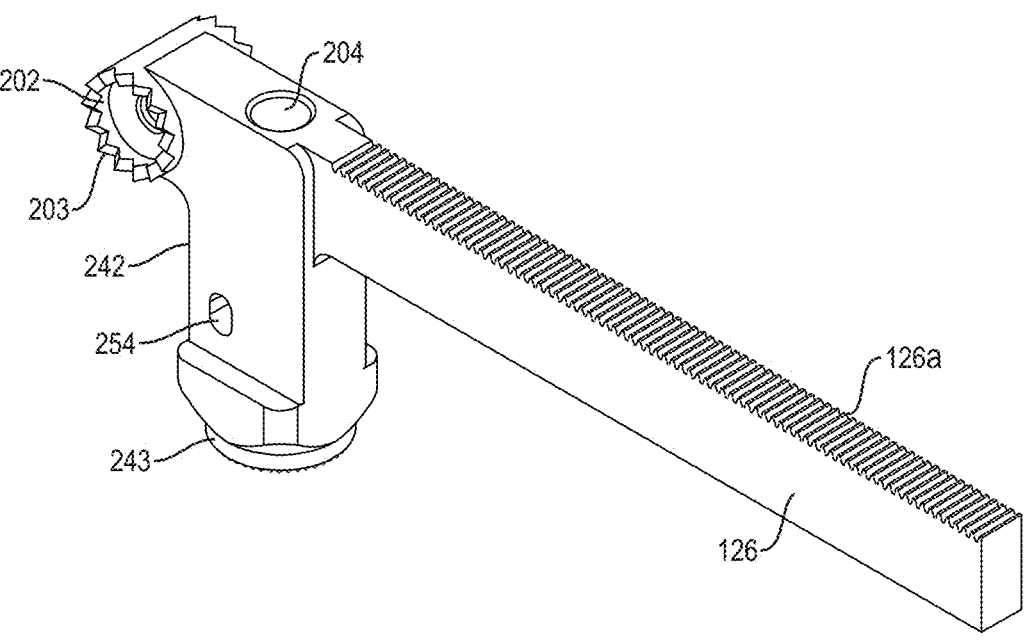
FIG. 32A is a top perspective view of a rack and rack hub of the posterior distractor rack assembly of FIG. 31A.
Figure 32B:
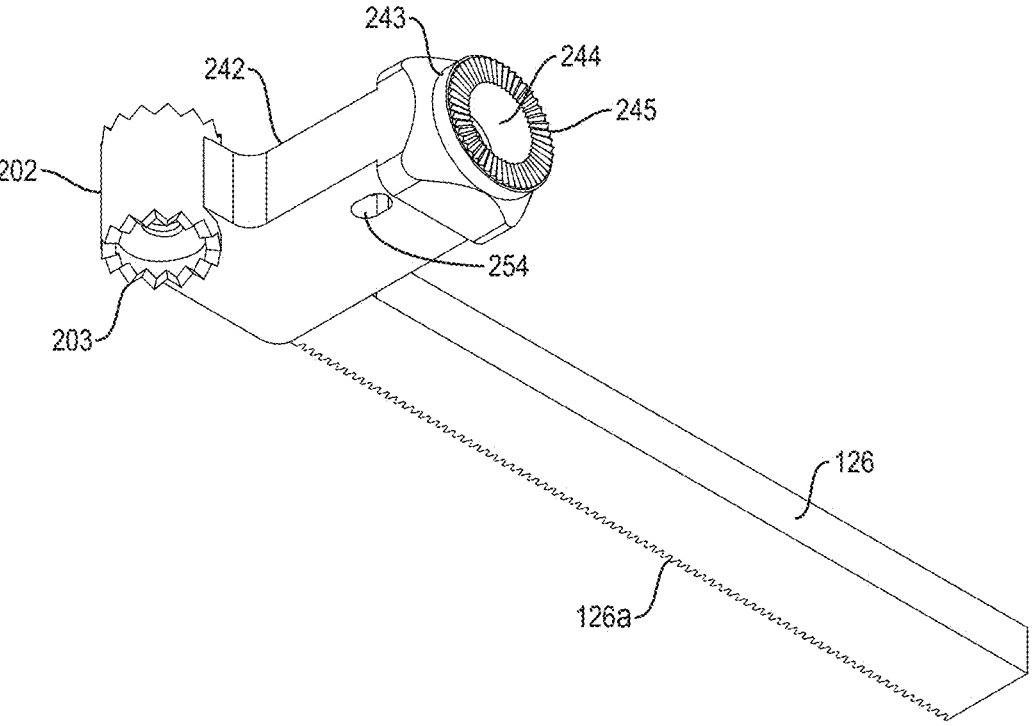
FIG. 32B is a bottom perspective view of the rack and rack hub of FIG. 32A.
Figures 32C, 32D, 32E, 32F, 32J:
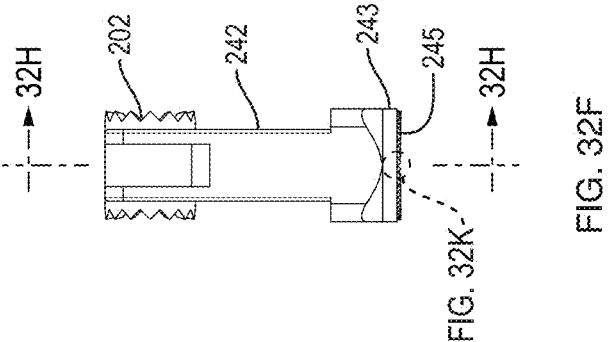
FIG. 32C is a front elevational view of the rack and rack hub of FIG. 32A.
FIG. 32D is a top plan view of the rack and rack hub of FIG. 32A.
FIG. 32E is a rear elevational view of the rack and rack hub of FIG. 32A.
FIG. 32F is a side elevational view of the rack and rack hub of FIG. 32A.
FIG. 32J is a detailed view of a portion of FIG. 32C, as denoted in dashed lines.
Figures 32G, 32H:
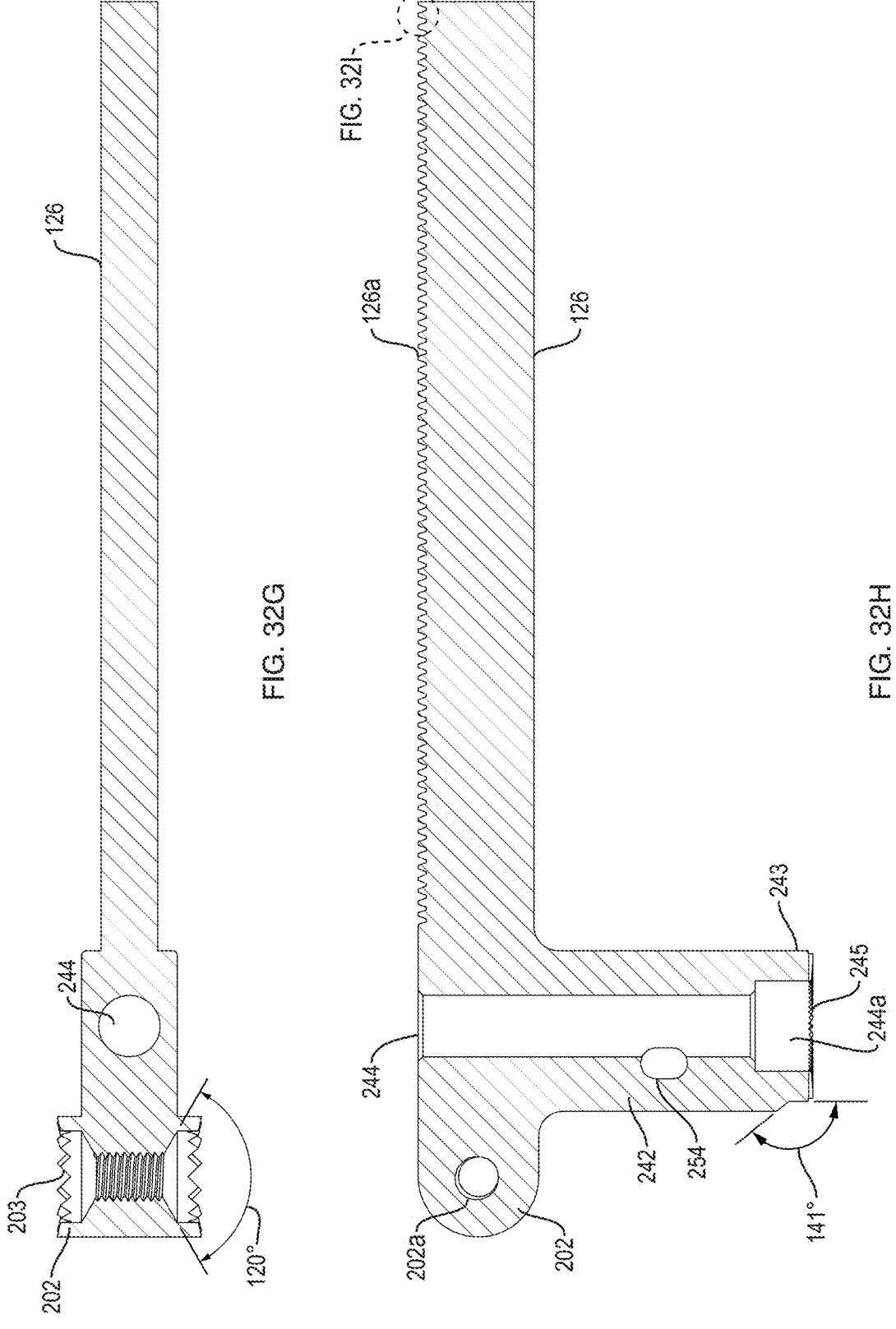
FIG. 32G is a cross-sectional view of the rack and rack hub of FIGS. 32A and 32D, as taken along line 32G-32G in FIG. 32D.
FIG. 32H is a cross-sectional view of the rack and rack hub of FIGS. 32A and 32F, as taken along line 32H-32H in FIG. 32F.

FIGS. 32A-32K further illustrate the rack 126 and rack hub 242 of the posterior distractor rack assembly 120. The rack 242 includes a cylindrical member 202 defining a threaded bore 202a therethrough, with a fifth plurality of teeth 203 on both ends thereof. The cavity 244 is formed in the rack hub 242 as a through bore, extending perpendicular to the threaded bore 202a, as shown in FIGS. 32A-32C, 32G and 32H. FIG. 32G shows an embodiment wherein the angle formed between the walls of the cylindrical member 202 and the threaded bore 202a is 120°. The cylindrical member 202 is configured to engage the B-arm posterior connector 112 (see FIGS. 13 and 13B). The configuration of the cylindrical member 202 and teeth 203 on both ends thereof facilitates that a single rack 126 and single compressor/distractor 114 can be used for both right- and left-sided approaches (i.e., to the patient's disc space) as it allows a surgeon to rotate or flip the rack according to the side of the approach.

FIG. 32H shows an embodiment wherein the angle formed between the annular end 243 and an adjacent portion of the rack hub 242 is 141°. Other angles are possible in other embodiments.

Figures 32I, 32J, 32K:
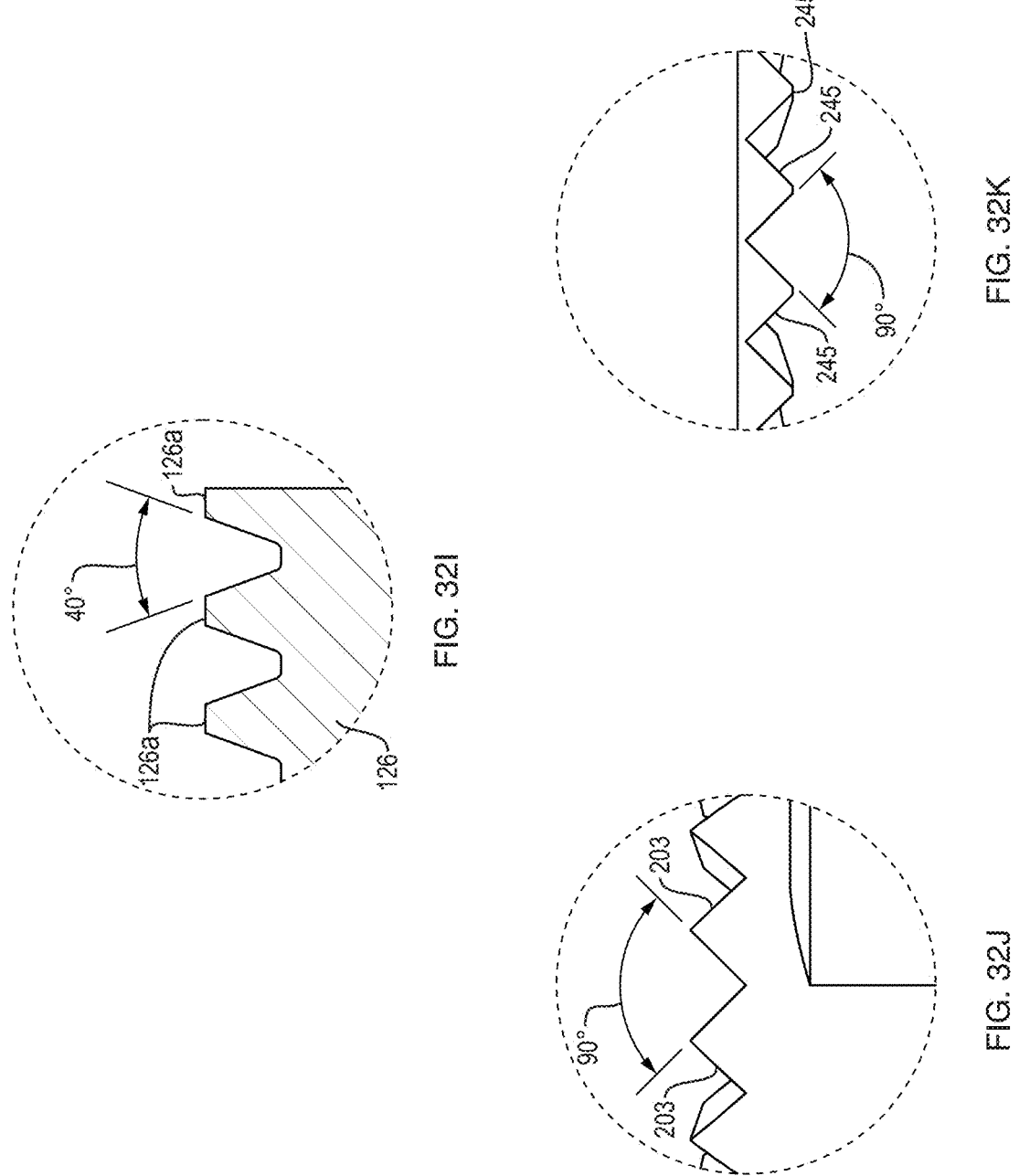
FIG. 32I is a detailed view of a portion of FIG. 32H, as denoted in dashed lines.
FIG. 32K is a detailed view of a portion of FIG. 32F, as denoted in dashed lines.
Figure 33A:
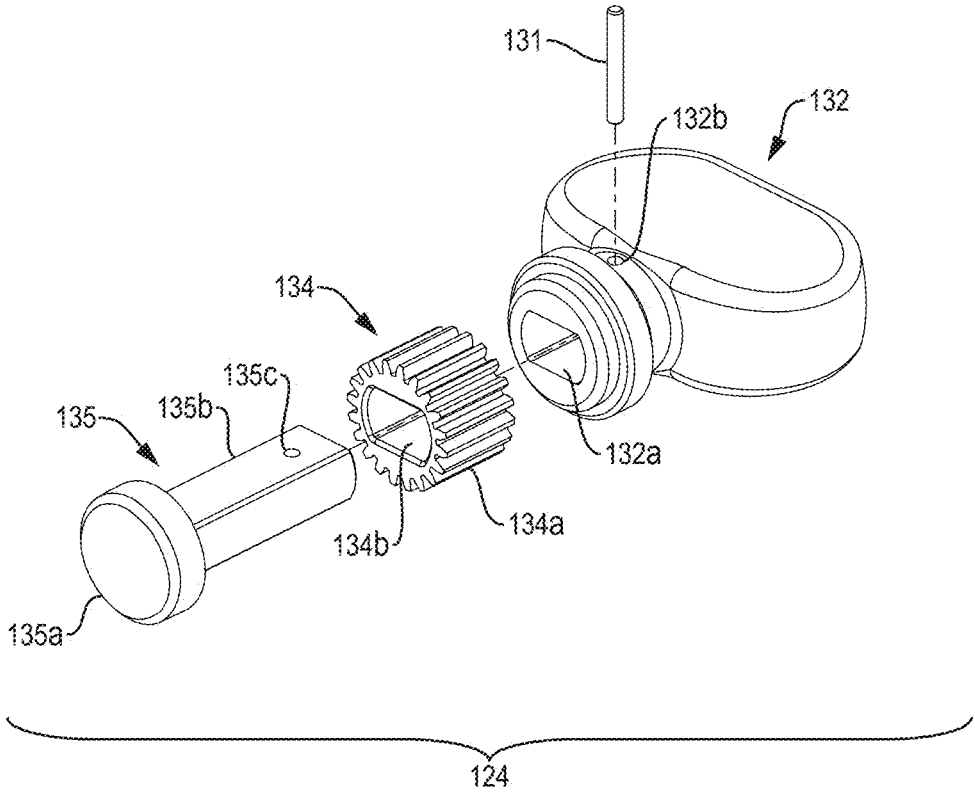
FIG. 33A is a top perspective exploded view of a pinion assembly of the posterior compressor/distractor of FIG. 14A.
Figure 33D:
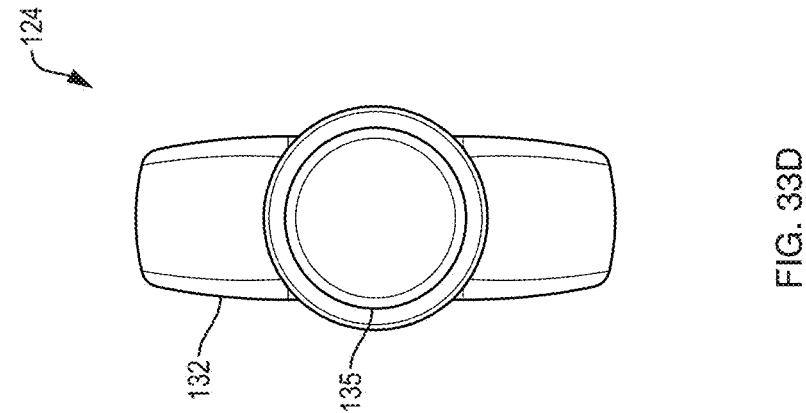
FIG. 33D is a bottom plan view of the pinion assembly of FIG. 33A.
Figure 33C:
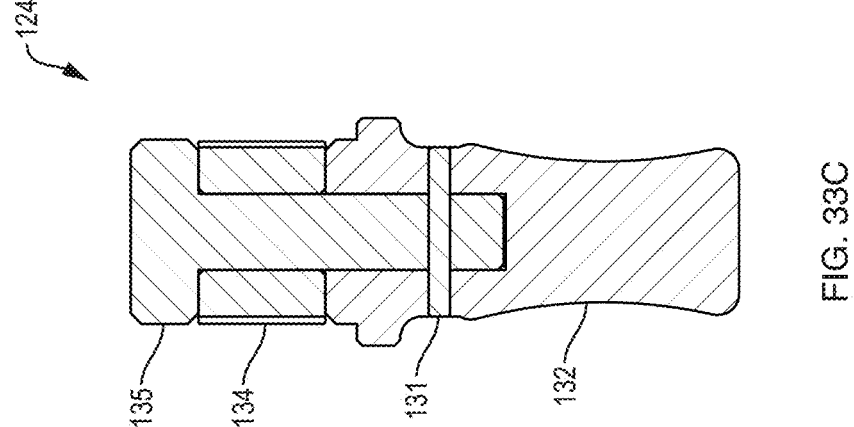
FIG. 33C is a cross-sectional view of the pinion assembly of FIGS. 33A and 33B, as taken along line 33C-33C in FIG. 33B.
Figure 33B:
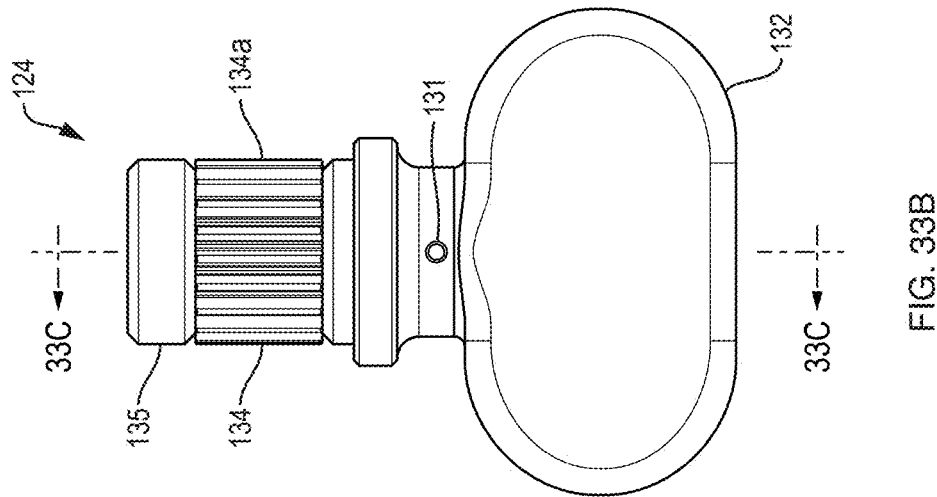
FIG. 33B is a side elevational view of the pinion assembly of FIG. 33A.
Figures 34A, 34B, 34C, 34D, 34E, 34F:
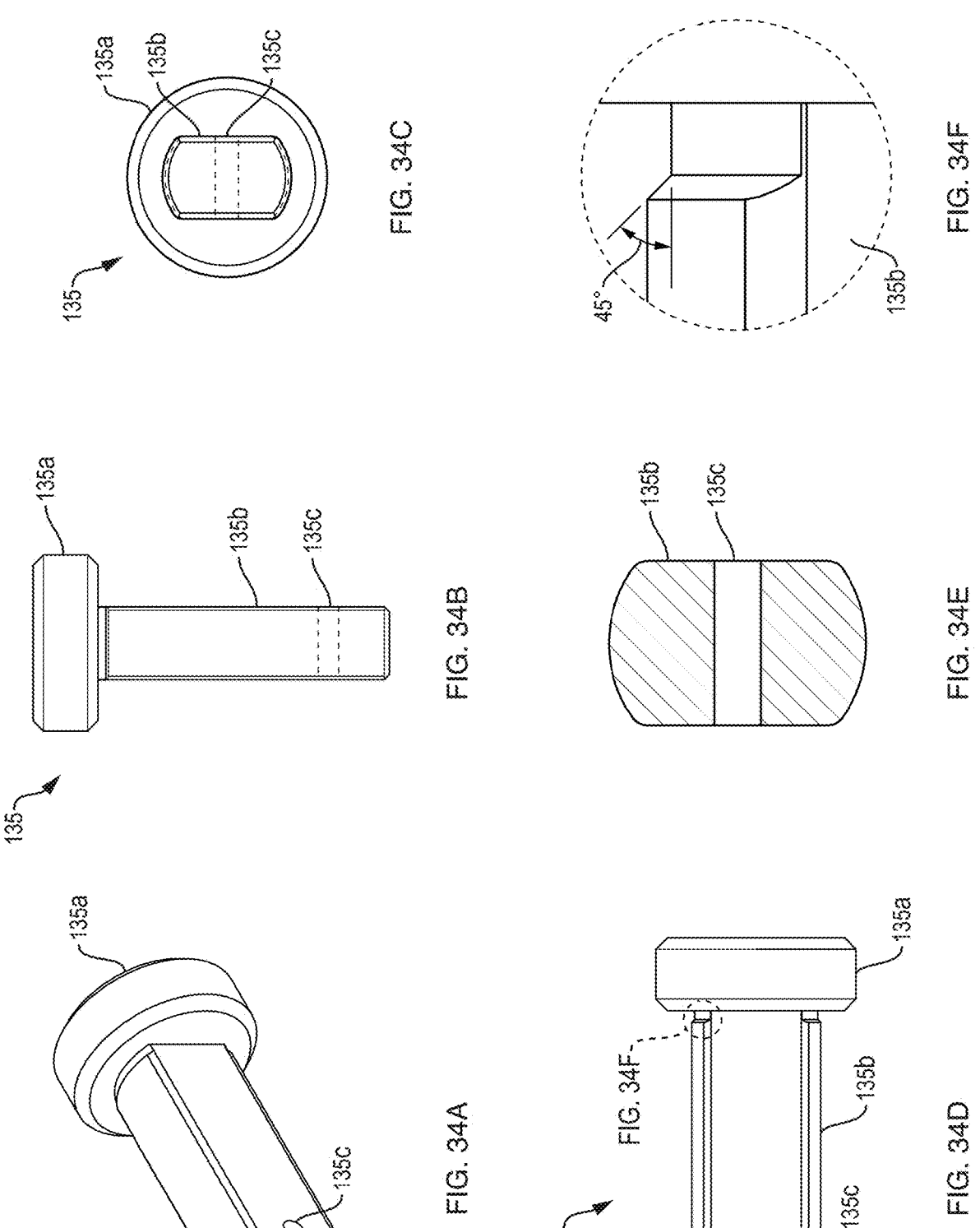
FIG. 34A is a top perspective view of a post of the pinion assembly of FIG. 33A.
FIG. 34B is a front elevational view of the post of FIG. 34A.
FIG. 34C is a bottom elevational view of the post of FIG. 34A.
FIG. 34D is a side elevational view of the post of FIG. 34A.
FIG. 34E is a cross-sectional view of the post of FIGS. 34A and 34D, as taken along line 34E-34E in FIG. 33D.
FIG. 34F is a detailed view of a portion of FIG. 32F, as denoted in dashed lines.
Figure 35G:
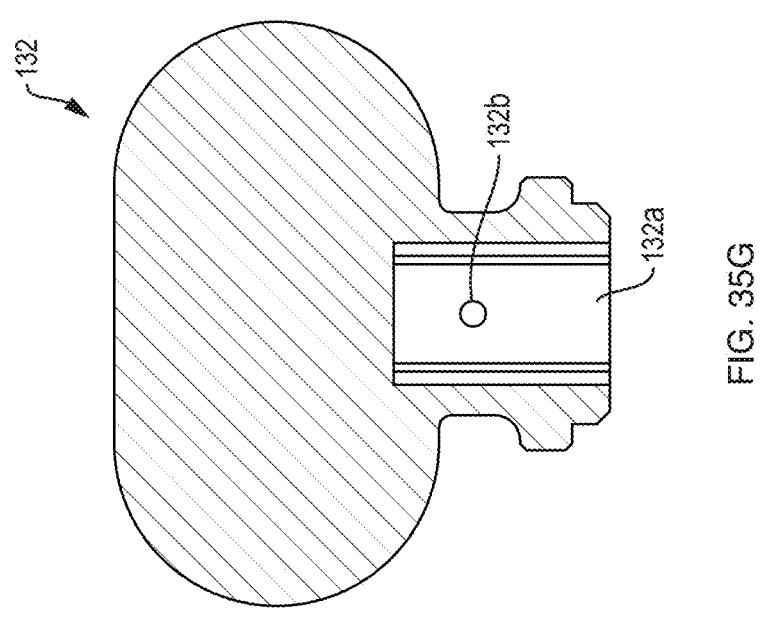
FIG. 35A is a front elevational view of a knob of the pinion assembly of FIG. 33A.
FIG. 35B is a side elevational plan view of the knob of FIG. 34A.
FIG. 35C is a bottom plan view of the knob of FIG. 35A.
Figure 35F:
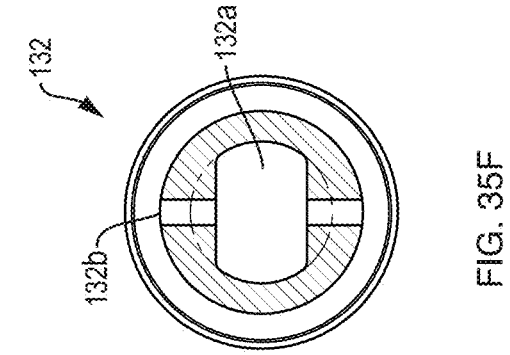
Figure 35E:
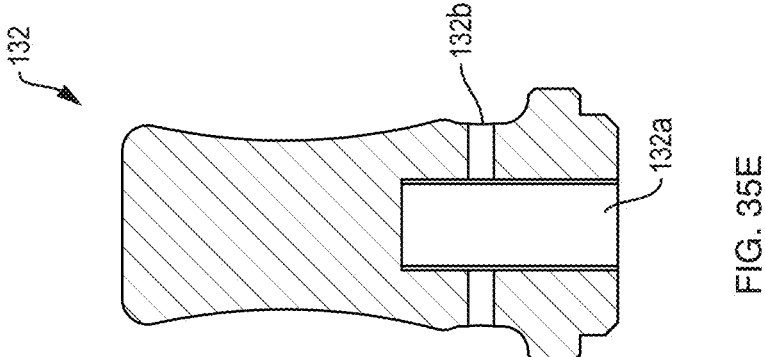
Figure 36C:
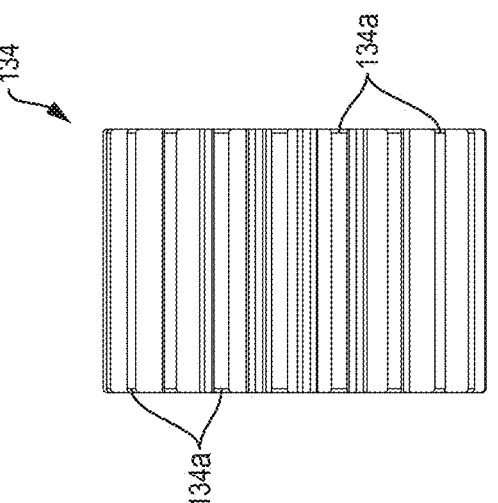
Figure 36A:
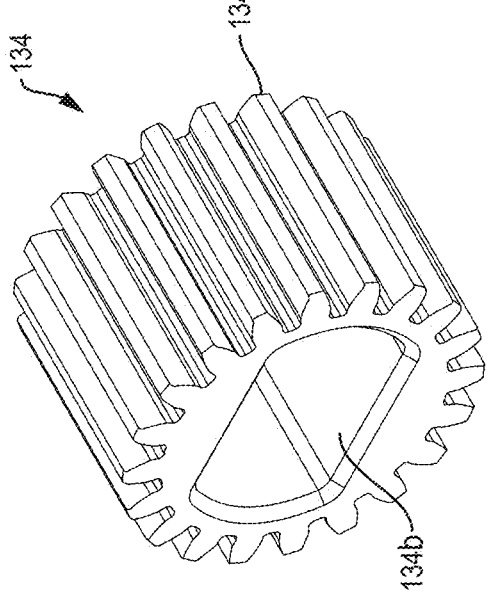
Figure 36B:
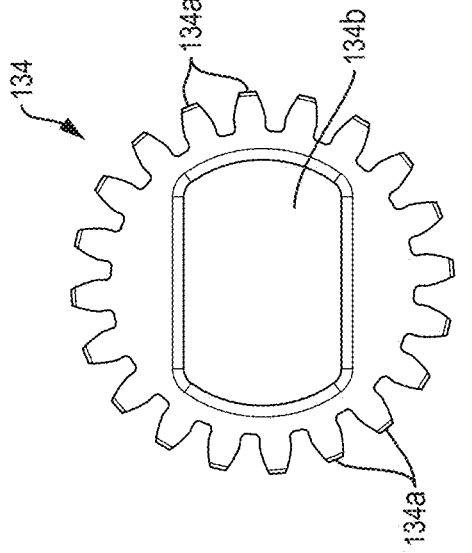
Figures 37A, 37B, 37C:
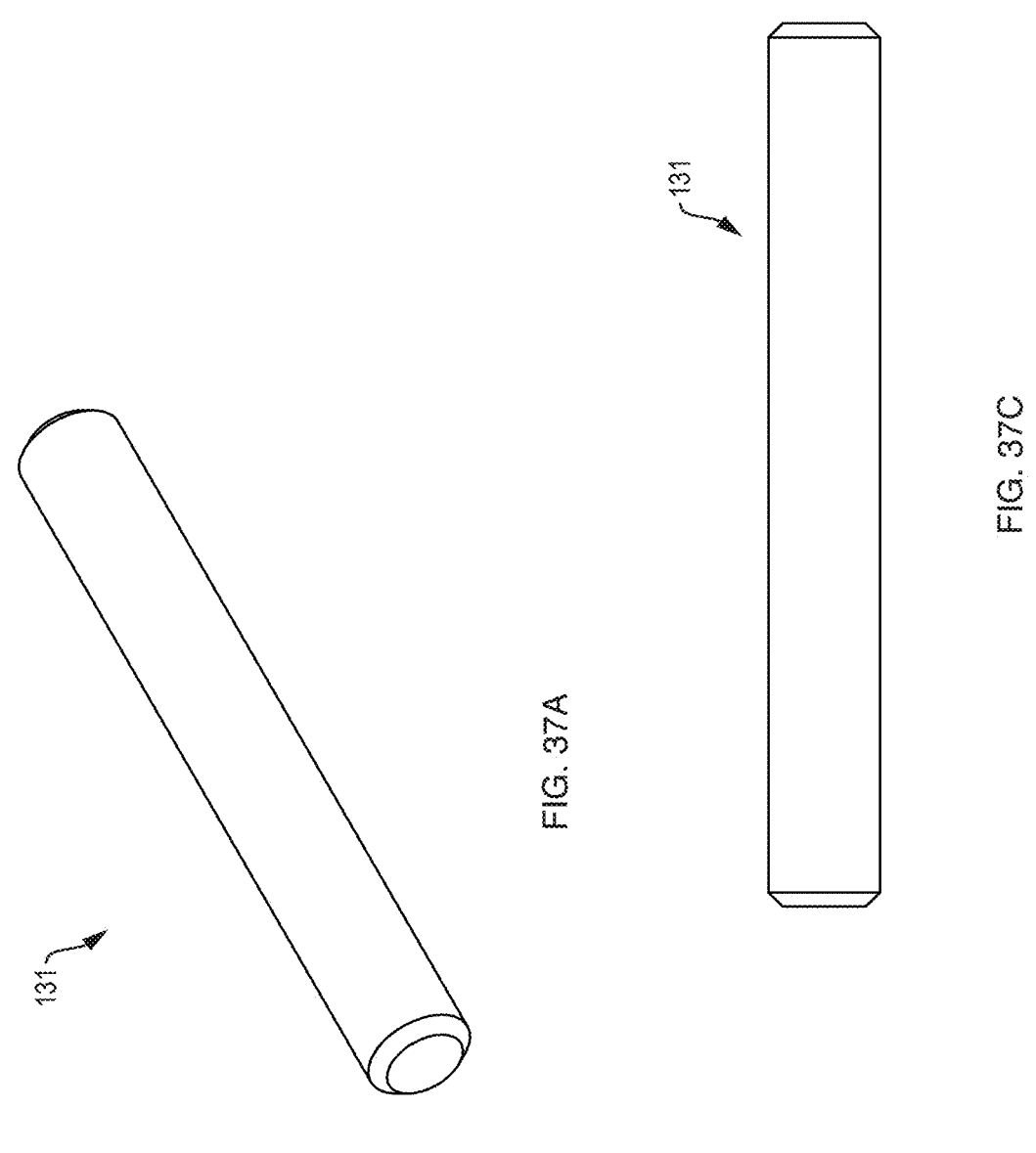

FIG. 32I shows an embodiment wherein the angle formed between adjacent ones of the ridges 126a of rack 126 is 40°. Other angles are possible in other embodiments.

FIG. 32J shows an embodiment wherein the angle between adjacent ones of the fifth plurality of teeth 203 is 90°. Other angles are possible in other embodiments.

FIG. 32K shows an embodiment wherein the angle between adjacent ones of the third plurality of teeth 245 is 90°. Other angles are possible in other embodiments.

FIGS. 33A-37C further illustrate the pinion assembly 124 and its components. As described above, the pinion assembly 124 includes the knob 132, the post 135 that engages the knob 132 (i.e., via insertion into a cavity 132a formed in the knob 132), and a gear 134 that includes ridges 134a on its surface that interdigitate with the ridges 126a on the rack 126. The gear 134 also includes a bore 134b configured to receive the post 135 therethrough. The post 135 includes a head 135a, a stem 135b descending from the head 135a and an aperture 135c formed in the stem 135b. The pinion assembly 124 further includes a pin 131 that insertably engages an aperture 132b formed in the knob 132 and the post aperture 135c. The pin 131 thereby secures the post 135 to the knob 132.

If the swivel tubes 162, 262 of the respective swivel tube subassemblies 138, 136 or the implants (e.g. intervertebral screws/rods-PLEASE CONFIRM) themselves are tracked using stereotactic navigation/fiduciaries, their position after lateral implant insertion may be compared to the relative position on initial placement, and such comparative data can be used to calculate the change in alignment achieved by lateral implant placement.

In the case of multilevel instrumentation, implants can be placed and this system can be used to distract across multiple levels without the need to reposition the distractor for lateral surgery at subsequent levels.

In general, any combination of disclosed features, components and methods described herein is possible. Steps of a method can be performed in any order that is physically possible.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed:

1. A method for performing a prone lateral spinal surgery on a patient, the method comprising the steps of:

(A) obtaining a patient in need of a spinal surgery;

(B) obtaining an internal fixation-based access system for prone lateral spinal surgery on the patient, comprising:

a lateral lumbar interbody fusion (LLIF) retractor 116 having an LLIF retractor adaptor 118 configured to connect to a surgical table;

a posterior compressor/distractor 114 operative to contact the spine at the patient's back and the back of the spine when the patient is prone for the surgery; wherein the LLIF retractor is operative to approach the spine from a lateral side approaching simultaneously from the side while the posterior compressor/distractor contacts and/or approaches the spine from the back;

an A-arm 104 configured to mount on a surgical table; and a B-arm 106 configured to engage an end of the table-mounted A-arm 104 and/or LLIF retractor and to engage the posterior compressor/distractor 114;

wherein the system is operative for performing prone lateral spine surgery on the patient without the use of a bolster, and the system enables a surgeon to access either the left or the right lateral side of the spine of the patient during the surgery; and (C) executing the surgery by approaching the spine posteriorly including with placement of a compressor/distractor which is attached to a lateral interbody fusion/lateral access retractor to approach the spine from either lateral side for implant placement and deformity correction.

2. The method of claim 1, wherein the B-arm 106 includes a lateral connector 108, wherein the A-arm 104 includes a distal clamp 110 on an end of the A-arm 104 that is configured to engage the B-arm lateral connector 108, and wherein the B-arm 106 further includes a B-arm posterior connector 112 that is configured to engage the posterior compressor/distractor 114.

3. The method of claim 1, wherein the posterior compressor/distractor 114 includes a a posterior distractor rack assembly 120;

a posterior distractor carriage assembly 122 configured to operably engage the posterior distractor rack assembly 120; and a pinion assembly 124 configured to operably engage the posterior distractor rack assembly 120 and the posterior distractor carriage assembly 122;

whereby the posterior distractor rack assembly 120 and posterior distractor carriage assembly 122 are movable relative to one another.

4. The method of claim 3, wherein the posterior distractor rack assembly 120 includes a rack 126 having a plurality of ridges 126a on at least one surface thereof, and wherein the posterior distractor carriage assembly 122 includes an opening 130 configured to receive the rack therethrough.

5. The method of claim 4, wherein the posterior distractor rack assembly 120 includes a first swivel tube subassembly 136 having a first swivel tube 262, wherein the posterior distractor carriage assembly 122 includes a second swivel tube subassembly 138 having a second swivel tube 162, and wherein the first and second swivel tubes are each configured to receive a pedicle screw and screw tower therein.

6. The method of claim 5, wherein the first and second swivel tube subassemblies 136, 138 are configured to be moved and positioned with respect to each other while maintaining a fixed sagittal, coronal, and axial orientation between tubes and their respective internal fixation devices.

7. The method of claim 6, wherein the second swivel tube subassembly 138 has a first arm 140 extending therefrom and a carriage hub 142 including a first cavity 144 configured to receive the first arm 140 therein, wherein the first cavity 144 includes a first opening 144a surrounded by a first annular end 143 having a first plurality of teeth 145 extending therefrom, and wherein the second swivel tube subassembly 138 includes a second plurality of teeth 147 proximate to and surrounding the arm 140, the second plurality of teeth 147 being configured to removably engage the first plurality of teeth 145.

8. The method of claim 7, wherein the first swivel tube subassembly 136 has a second arm 240 extending therefrom and a rack hub 242 including a second cavity 244 configured to receive the second arm 240 therein, wherein the second cavity 244 includes a second opening 244a surrounded by a second annular end 243 having a third plurality of teeth 245 extending therefrom, and wherein the first swivel tube subassembly 136 includes a fourth plurality of teeth 247 proximate to and surrounding the second arm 240, the fourth plurality of teeth 247 being configured to removably engage the third plurality of teeth 245.

9. The method of claim 8, wherein the first arm 140 includes a first annular groove 141 formed in an end thereof, wherein the posterior distractor carriage assembly 122 includes a carriage hub 142 having a first spring lever assembly 127, the first spring lever assembly 127 having a first top cam lever 148, a first bottom cam lever 150, and a first cam pin 152 configured to connect the first top and bottom cam levers 148, 150 together on opposed surfaces of the carriage hub 142 through a first cam aperture 154 formed therein.

10. The method of claim 9, wherein the first cam pin 152 is configured to engage the first groove 141 of the first arm 140 when inserted into the first cavity 144, wherein rotation of the first top and bottom cam levers 148, 150 causes rotation of the first cam pin 152 and the inward movement of the first arm 140 into the first cavity 144, in turn causing the second plurality of teeth 147 on the second swivel tube subassembly 138 to removably engage the first plurality of teeth 145 and lock the second swivel tube subassembly 138 to the carriage hub 142, whereby the angle between the first and second swivel tubes 262, 162 is adjustable to accommodate an angle of pedicle screws, and whereby the compressor/distractor 114 is rotatable for use in both right-and left-sided approaches to the patient's disc space.

11. The method of claim 10, wherein the second arm 240 includes a second annular groove 241 formed in an end thereof, wherein the posterior distractor rack assembly 120 includes a rack hub 242 having a second spring lever assembly 227, the second spring lever assembly 227 having a second top cam lever 248, a second bottom cam lever 250, and a second cam pin 252 configured to connect the second top and bottom cam levers 248, 250 together on opposed surfaces of the rack hub 242 through a second cam aperture 254 formed therein.

12. The method of claim 11, wherein the second cam pin 252 is configured to engage the second groove 241 of the second arm 240 when inserted into the second cavity 244, wherein rotation of the second top and bottom cam levers 248, 250 causes rotation of the second cam pin 252 and the inward movement of the second arm 240 into the second cavity 244, in turn causing the fourth plurality of teeth 247 on the first swivel tube subassembly 136 to removably engage the third plurality of teeth 245 and lock the first swivel tube subassembly 136 to the rack hub 242, whereby the angle between the first and second swivel tubes 262, 162 is further adjustable to accommodate an angle of pedicle screws, and whereby the compressor/distractor 114 is further rotatable for use in both right-and left-sided approaches to the patient's disc space.

13. The method of claim 4, wherein the pinion assembly includes a knob 132, a post 135 descending from the knob 132, a gear 134 circumferentially engaging the post 135 and having ridges 134a that interdigitate with the ridges 126a on the rack 126, and wherein the posterior distractor carriage assembly 122 includes an aperture 129 dimensioned to receive the post 135 and gear 134 of the pinion assembly 124 therein.

14. An method for prone lateral spinal surgery on a patient, comprising the steps of:

(A) obtaining a patient in need of a spinal surgery;

(B) obtaining an internal fixation-based access system for prone lateral spine surgery comprising a lateral lumbar interbody fusion (LLIF) retractor 116 having an LLIF retractor adaptor 118 configured to connect to a surgical table; and

a posterior compressor/distractor 114 operative to contact the spine at the patient's back and the dorsal spine when the patient is prone for the surgery;

wherein the LLIF retractor is operative to approach the spine from a lateral side approaching simultaneously from the side while the posterior compressor/distractor contacts and/or approaches the spine from the back;

including a posterior distractor rack assembly 120 including a rack 126 having a plurality of ridges 126a on at least one surface thereof;

a posterior distractor carriage assembly 122 configured to operably engage the posterior distractor rack assembly 120 and including an opening 130 configured to receive the rack 126 therethrough; and a pinion assembly 124 configured to operably engage the posterior distractor rack assembly 120 and the posterior distractor carriage assembly 122;

whereby the posterior distractor rack assembly 120 and posterior distractor carriage assembly 122 are movable relative to one another; wherein the system is operative for performing prone lateral spine surgery on the patient without the use of a bolster, and the system enables a surgeon to access either the left or the right lateral side of the spine of the patient during the surgery;

(C) executing the surgery by approaching the patient's spine posteriorly including with placement of a compressor/distractor which is attached to a lateral fusion/lateraly access retractor to approach the spine from either lateral side for implant placement and deformity correction.

15. The method of claim 14, wherein the posterior distractor rack assembly 120 includes a first swivel tube subassembly 136 having a first swivel tube 262, wherein the posterior distractor carriage assembly 122 includes a second swivel tube subassembly 138 having a second swivel tube 162, wherein the first and second swivel tubes are each configured to receive a pedicle screw and screw tower therein, and wherein the first and second swivel tube subassemblies 136, 138 are configured to be moved and positioned with respect to each other.

16. The method of claim 15, wherein the second swivel tube subassembly 138 has a first arm 140 extending therefrom and a carriage hub 142 including a first cavity 144 configured to receive the first arm 140 therein, wherein the first cavity 144 includes a first opening 144a surrounded by a first annular end 143 having a first plurality of teeth 145 extending therefrom, and wherein the second swivel tube subassembly 138 includes a second plurality of teeth 147 proximate to and surrounding the arm 140, the second plurality of teeth 147 being configured to removably engage the first plurality of teeth 145, whereby the second swivel tube subassembly 138 is removably lockable to the first carriage hub 142, whereby the angle between the first and second swivel tubes 262, 162 is adjustable to accommodate an angle of pedicle screws, and whereby the compressor/distractor 114 is rotatable for use in both right-and left-sided approaches to the patient's disc space.

17. The method of claim 16, wherein the first swivel tube subassembly 136 has a second arm 240 extending therefrom and a rack hub 242 including a second cavity 244 configured to receive the second arm 240 therein, wherein the second cavity 244 includes a second opening 244a surrounded by a second annular end 243 having a third plurality of teeth 245 extending therefrom, and wherein the first swivel tube subassembly 136 includes a fourth plurality of teeth 247 proximate to and surrounding the arm 240, the fourth plurality of teeth 247 being configured to removably engage the third plurality of teeth 245, whereby the first swivel tube subassembly 136 is removably lockable to the rack hub 242, whereby the angle between the first and second swivel tubes 262, 162 is further adjustable to accommodate an angle of pedicle screws, and whereby the compressor/distractor 114 is further rotatable for use in both right-and left-sided approaches to the patient's disc space.

18. The method of claim 14, wherein the pinion assembly includes a knob 132, a post 135 descending from the knob 132, a gear 134 circumferentially engaging the post 135 and having ridges 134a that interdigitate with the ridges 126a on the rack 126, and wherein the posterior distractor carriage assembly 122 includes an aperture 129 dimensioned to receive the post 135 and gear 134 of the pinion assembly 124 therein.

19. An method for spinal surgery on a patient, comprising:
(A) obtaining a patient in need of a spinal surgery;
(B) obtaining an internal fixation-based access system for prone lateral spinal surgery on the patient, comprising:
a lateral lumbar interbody fusion (LLIF) retractor 116 having an LLIF retractor adaptor 118 configured to connect to a surgical table;
a posterior compressor/distractor 114 operative to contact the spine at the patient's back and the back of the spine when the patient is prone for the surgery; wherein the LLIF retractor is operative to approach the spine from a lateral side approaching simultaneously from the side while the posterior compressor/distractor contacts and/or approaches the spine from the back;
an A-arm 104 configured to mount on a surgical table; and
a B-arm 106 configured to engage an end of the table-mounted A-arm 104 and/or LLIF retractor and to engage the posterior compressor/distractor 114;
one or more cannulated pedicle screws that are each insertable through respective pedicles of the patient's spine;
a distracting frame 20 configured to operably connect the one or more screws to each other;
means for mounting the internal fixation system to a surgical table;
wherein the system is operative for performing prone lateral spine surgery on the patient without the use of a bolster, and the system enables a surgeon to access either the left or the right lateral side of the spine of the patient during the surgery; and
(C) executing the surgery by approaching the patient's spine posteriorly including with placement of a compressor/distractor which is attached to a lateral fusion/lateraly access retractor to approach the spine from either lateral side for implant placement and deformity correction.

20. The method of claim 19, further including one or more screw towers or a non-tower based posterior distractor system configured to removably engage one or more cannulated pedicle screws and thereby fix the one or more screws in a monoaxial configuration.

21. The method of claim 1, wherein the method is operative for access to lower lumbar spine levels that are obstructed by the iliac wing or for thoracolumbar levels where ribs obstruct access, with the posterior distractor attached and/or holding one or more screws monoaxially and the lateral retractor provisionally positioned, the rail-based posterior distractor assembly is operative to be used to manipulate the spine relative to the iliac wing or ribs to allow access to the these levels, wherein:

the B arm hinge is unlocked and the lateral retractor is operative to be rotated and translated to move the obstructing ribs or iliac wing away; and the B arm hinge can be locked to hold this position.

22. The method of claim 1, wherein the method is operative to correct a spinal deformity in the axial, coronal, or sagittal plane; wherein the B arm is operative to be unlocked, with the posterior distractor attached holding one or more screws monoaxially, and the lateral retractor is capable to be provisionally positioned;

wherein the posterior distractor is rotated in the axial, coronal, or sagittal plane to correct segmental or regional deformities; and the B arm hinge can then be locked to hold this position.

23. The method of claim 1, wherein the method is operative for surgery in the case of multilevel prone lateral surgeries, when moving from one level to the next, the prone lateral system provides control over the movement of the lateral retractor; and when moving to an adjacent level of the spine, the B arm hinge is partially but not fully loosened, such that the lateral retractor can be slid up or down to the adjacent level; and with the proviso that this prevents the lateral retractor from moving in an uncontrolled fashion in axial, coronal, or sagittal planes as happens without the supplemental fixation of the B arm.

24. The method of claim 1, wherein with the posterior distractor fixated and the pedicle screw fixation fixed in a monoaxial orientation, the posterior distractor is operative to be used to distract or compress the operative disc space sequentially; and the distraction function can be used to minimize the force necessary for insertion of disc preparation, trials, and implants;

whereby this minimizes the trauma to the vertebral endplates and the compression function returns the distracted vertebral endplates into a position of opposition to the trial or implant placed.

25. The method of claim 1, wherein the system establishes and maintains the position of the lateral retractor against the vertebra and controls that position in a fixed angle when the A and B arms are locked;

whereby the system prevents lateral retractor motion during a discectomy, trialing, and implantation work;

wherein the system thereby prevents psoas creep or a condition wherein the psoas muscle, through which a surgeon is operating, can slip under the retractor blades and thereby come to obstruct visualization through the lateral retractor.

26. The method of claim 1, wherein the B-arm engages the LLIF retractor on one end and engages the posterior compressor/distractor on the other end.

* * * * *